United States Patent [19]

Kimura et al.

[11] Patent Number: 5,116,990
[45] Date of Patent: May 26, 1992

[54] MAGENTA DYE-FORMING COUPLER

[75] Inventors: Keizo Kimura; Tadahisa Sato, both of Minami-ashigara, Japan

[73] Assignee: Fuji Photo Film Co., Ltd., Kanagawa, Japan

[21] Appl. No.: 563,822

[22] Filed: Aug. 2, 1990

Related U.S. Application Data

[63] Continuation of Ser. No. 205,064, Jun. 10, 1988, abandoned.

[30] Foreign Application Priority Data

Jun. 10, 1987 [JP] Japan ............................... 62-144362

[51] Int. Cl.⁵ .............................................. C07D 403/00
[52] U.S. Cl. ................................... 548/262.4; 548/158; 544/333; 546/266; 546/268; 546/271; 430/558
[58] Field of Search ................. 548/262.4, 158; 544/333; 546/271, 266, 268; 430/558

[56] References Cited

U.S. PATENT DOCUMENTS

| | | | |
|---|---|---|---|
| 3,725,067 | 3/1973 | Bailey | 430/476 |
| 4,500,630 | 2/1985 | Sato et al. | 430/386 |
| 4,540,654 | 9/1985 | Sato et al. | 430/381 |
| 4,621,046 | 11/1986 | Sato et al. | 548/266 |
| 4,622,287 | 11/1986 | Umemoto et al. | 430/505 |
| 4,822,730 | 4/1989 | Furutachi et al. | 430/558 |

FOREIGN PATENT DOCUMENTS

| | | |
|---|---|---|
| 85109626 | 7/1986 | China. |
| 0119860 | 9/1984 | European Pat. Off. |
| 0173256 | 3/1986 | European Pat. Off. |
| 0226849 | 7/1987 | European Pat. Off. |
| 0270078 | 6/1988 | European Pat. Off. |
| 119860 | 9/1984 | Japan ................... 548/266 |
| 176804A | 4/1986 | Japan ................... 548/266 |
| 61-147254 | 7/1986 | Japan. |
| 3633364 | 4/1988 | Japan ................... 548/266 |

Primary Examiner—Joseph L. Schofer
Assistant Examiner—Alex H. Walker
Attorney, Agent, or Firm—Birch, Stewart, Kolasch & Birch

[57] ABSTRACT

There are provided 1H-pyrazolo[1,5-b]-1,2,4-triazole magenta couplers or 1H-pyrazolo[5,1-c]-1,2,4-triazole magenta couplers characterized by having at the 6-position a phenoxy group, on the ortho-position of which is an alkoxy group or an aryloxy group. A photographic material comprising the magenta coupler is excellent in color reproducibility and exhibits superior photographic characteristics in any of sensitivity, gradation, and color density.

14 Claims, No Drawings

MAGENTA DYE-FORMING COUPLER

This application is a continuation of application Ser. No. 07/205,064 filed on June 10, 1988, now abandoned.

BACKGROUND OF THE INVENTION

(1) Field of the Invention

The present invention relates to novel magenta dye-forming couplers (hereinafter referred to as magenta couplers), and in particular, to magenta couplers that improve the sensitivity, the color density, and the gradation ($\gamma$) of the image of silver halide color photographic materials. More particularly, the present invention relates to 1H-pyrazolo[1,5-b]-1,2,4-triazole magenta couplers or 1H-pyrazolo[5,1-c]-1,2,4-triazole magenta couplers being characterized by having at the 6-position a phenoxy group, on the ortho-position of which is an alkoxy group or an aryloxy group.

(2) Description of the Prior Art

It is well known that aromatic primary amine-type color developing agents, which have been oxidized by an exposed silver halide that acts as an oxidizing agent, and couplers react to produce indophenols, indoanilines, indamines, azomethines, phenoxazines, phenazines, or dyes similar thereto, to form images.

Of these, 5-pyrazolone, cyanoacetophenone, indazolone, pyrazolobenzimidazole, and pyrazolotriazole-type couplers are used to form magenta color images.

Hitherto, most magenta color image-forming couplers that were widely used in practice and studied were 5-pyrazolones. However, it was known that the dyes formed from 5-pyrazolone-type couplers had undesired absorption of yellow components at around 430 nm, which caused color turbidity.

As magenta color image-forming compound skeletons are suggested pyrazolobenzimidazole skeletons described in British Patent No. 1,047,612, indazolone skeletons described in U.S. Pat. No. 3,770,447, and pyrazolo [5,1-c]-1,2,4-triazole skeletons described in U.S. Pat. No. 3,725,067.

However, the magenta couplers described in these patents are still unsatisfactory in that when the magenta coupler is dispersed in a hydrophilic protective colloid, such as gelatin, and mixed with a silver halide emulsion, only an unsatisfactory color image occurs, or in that the solubility into a high-boiling organic solvent is low, or the synthesis is difficult, or the coupling activity is relatively low when a common developing solution is used, or the light-fastness of the dye is quite low.

The inventor of the present invention studied various new types of magenta color image couplers that exhibit no subsidiary absorption at around 430 nm, which is the most disadvantageous point of 5-pyrazolone-type couplers in view of the hue, and found 1H-pyrazolo[1,5-b]-1,2,4-triazole magenta couplers that exhibit no subsidiary absorption on the short wavelength side, are high in fastness of the dye image, are easy to synthesize, and are disclosed in Japanese Patent Application (OPI) No. 171956/1984 and U.S. Pat. No. 4,540,654. These couplers are excellent in color reproducibility, synthetically excellent, and they have characteristics that when a coupling split-off group is introduced to the coupling-active position they can be made two-equivalent, and the amount of silver used can be reduced. However, when the coupling split-off group designated by (X) in the coupler is halogen, alkylthio, or arylthio, which can be easily synthesized, the magenta couplers have the problem that the sensitivity and the gradation ($\gamma$) of a photographic material obtained thereof are a little inferior to those of 5-pyrazolone type magenta couplers. Therefore, couplers wherein X is an aryloxy group as disclosed in Japanese Patent Application No. 176352/1984 were found as one means of solving the problem. However, although the aryloxy coupling-split-off, type couplers could solve the above problem, they have defects including low synthesis yield, so that they are not adapted to large-scale synthesis, and the stability is low. Pyrazolotriazoles described in U.S. Pat. No. 3,725,067 mentioned above also have similar defects.

BRIEF SUMMARY OF THE INVENTION

Therefore, an object of the present invention is to provide a magenta coupler that solve these problems.

Another object of the present invention is to provide a magenta coupler that exhibits high sensitivity and improved gradation ($\gamma$) in a color image.

Other and further objects, features, and advantages of the invention will appear more evident from the following description.

DETAILED DESCRIPTION OF THE INVENTION

The above problems have been solved by a magenta coupler represented by formula (I) or (II):

Formula (I):

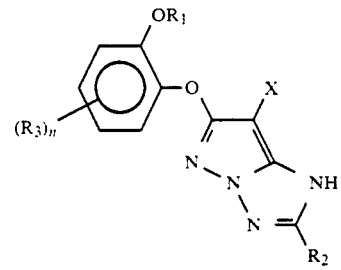

Formula (II):

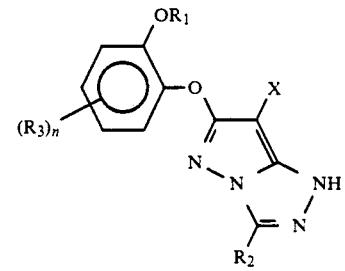

wherein $R_1$ represents a hydrogen atom, an alkyl group, or an aryl group; $R_2$ represents an alkyl group, an aryl group, a heterocyclic group, a cyano group, an alkoxy group, an aryloxy group, an alkylthio group, an arylthio group, or a heterocyclic thio group; $R_3$ represents a hydrogen atom, a halogen atom, an alkoxy group, an aryloxy group, an alkylamino group, an anilino group, an alkylthio group, or an arylthio group; X represents a hydrogen atom or a coupling split-off group; n is an integer of 0 to 4; $R_1$ and $R_3$ may bond together to form a ring, and a dimer or higher polymer coupler may be formed via any one of $R_1$, $R_2$, $R_3$, and X.

More particularly, $R_1$ represents a hydrogen atom, an alkyl group, (e.g., methyl, ethyl, isopropyl, t-butyl, phenylmethyl, methoxyethyl and 2-phenoxyethyl) or an aryl group, (e.g., phenyl, 4-methylphenyl, 4-t-butylphenyl, 4-halogenophenyl, and 4-alkoxyphenyl). Preferably the alkyl group represented by $R_1$ is one having 1 to 18 carbon atoms, more preferably 1 to 7 carbon atoms. Preferably the aryl group represented by $R_1$ is one having 6 to 20 carbon atoms, more preferably 6 to 12 carbon atoms.

$R_2$ represents an alkyl group [for example, a substituted alkyl group such as a sulfonamido-substituted alkyl group (e.g., sulfonamidomethyl, 1-sulfonamidoethyl, 2-sulfonamidoethyl, 1-methyl-2-sulfonamidoethyl, and 3-sulfonamidopropyl), an acylamino-substituted alkyl group (e.g., acylaminomethyl, 1-acylaminoethyl, 2-acylaminoethyl, 1-methyl-2-acylaminoethyl, and 3-acylaminopropyl), a sulfonamido-substituted phenylalkyl group (e.g., p-sulfonamidophenylmethyl, p-sulfonamidophenylethyl, 1-(p-sulfonamidophenyl)ethyl, and p-sulfonamidophenylpropyl), an acylamino-substituted phenylalkyl group {e.g., p-acylaminophenylmethyl, p-acylaminophenylethyl, 1-(p-acylaminophenyl)ethyl, and p-acylaminophenylpropyl)}, an alkylsulfonyl-substituted alkyl group (e.g., 2-dodecylsulfonylethyl, 1-methyl-2-pentadecylsulfonylethyl, and octadecylsulfonylpropyl), and a phenylsulfonyl-substituted alkyl group {e.g., 3-(2-butyl-5-t-octylphenylsulfonyl)propyl, and 2-(4-dodecyloxyphenylsulfonyl)ethyl}, and an unsubstituted alkyl group such as a methyl group, an ethyl group, a hexyl group, and a dodecyl group], an aryl group (for example a substituted aryl group, e.g., sulfonamidophenyl, acylaminophenyl, alkoxyphenyl, aryloxyphenyl, substituted alkylphenyl, and sulfonamidonaphthyl, acylaminonaphthyl, and an unsubstituted aryl group, e.g., phenyl, and naphthyl), a heterocyclic group (e.g., 2-furyl, 2-thienyl, 2-pyrimidinyl, and 2-benzothiazolyl), a cyano group, an alkoxy group (e.g., methoxy, ethoxy, 2-methoxyethoxy, 2-dodecylethoxy, and 2-methanesulfonylethoxy), an aryloxy group (e.g. phenoxy, 2-methylphenoxy, and 4-t-butylphenoxy), an alkylthio group (e.g., methylthio, octylthio, tetradecylthio, 2-phenoxyethylthio, 3-phenoxypropylthio, and 3-(4-t-butylphenoxy)propylthio), an arylthio group (e.g., phenylthio, 2-butoxy-5-t-octylphenylthio, 3-pentadecylphenylthio, 2-carboxyphenylthio, and 4-tetradecaneamidophenylthio), or a heterocyclic thio group (e.g., 2-benzothiazolylthio, 2,4-di-phenoxy-1,3,5-triazole-6-thio, and 2-pyridylthio).

$R_2$ is described below more detail: the alkyl group is preferably one having 5 to 60 carbon atoms, more preferably 12 to 40 carbon atoms; the aryl group is preferably one having 6 to 80 carbon atoms, more preferably 12 to 50 carbon atoms; the heterocyclic group is preferably one having 4 to 80 carbon atoms, more preferably 10 to 50 carbon atoms; the alkylthio group is preferably one having 5 to 60 carbon atoms, more preferably 12 to 40 carbon atoms; the arylthio group is preferably one having 6 to 80 carbon atoms; more preferably 12 to 50 carbon atoms; the heterocyclic thio group is preferably one having 4 to 80 carbon atoms, more preferably 10 to 50 carbon atoms.

$R_3$ represents a hydrogen atom, a halogen atom (e.g., fluorine, chlorine, and bromine), an alkoxy group (e.g., methoxy, ethoxy, 2-methoxyethoxy, 2-dodecylethoxy, and 2-methanesulfonylethoxy), an aryloxy group (e.g., phenoxy, 2-methylphenoxy, and 4-t-butylphenoxy), an alkylamino group (e.g., methylamino, ethylamino, decylamino, dimethylamino, and diethylamino), or an anilino group (e.g., phenylamino, 2-chloroanilino, N-methylanilino, and 3-alkoxyanilino), and an alkylthio group, and the arylthio group represented by $R_2$ may be the same as those represented by $R_2$.

$R_3$ is described below more detail: the alkoxy group is preferably one having 1 to 20 carbon atoms, more preferably 1 to 12 carbon atoms; the aryloxy group is preferably one having 6 to 20 carbon atoms, more preferably 6 to 14; the alkylamino group is preferably one having 1 to 20 carbon atoms, more preferably 1 to 12; the anilino group is preferably one having 6 to 20 carbon atoms, more preferably 6 to 14 carbon atoms; the alkylthio group is preferably one having 1 to 20 carbon atoms, more preferably 1 to 12 carbon atoms; the arylthio group is preferably one having 6 to 20 carbon atoms, more preferably 6 to 14 carbon atoms.

X represents a hydrogen atom, a halogen atom (e.g., chlorine, bromine, and iodine), a carboxy group, or a group that links via the oxygen atom (e.g., acetoxy, propanoyloxy, benzoyloxy, 2,4-dichlorobenzoyloxy, ethoxyoxaloyl, pyruvinyloxy, cinnamoyloxy, phenoxy, 4-cyanophenoxyl, 4-methanesulfonamidophenoxy, 4-methanesulfonylphenoxy, α-naphthoxy, 3-pentadecylphenoxy, benzyloxycarbonyloxy, ethoxy, 2-cyanoethoxy, benzyloxy, 2-phenetyloxy, 2-phenoxyethoxy, 5-phenyltetrazolyloxy, and 2-benzothiazolyloxy), a group that links via the nitrogen atom (e.g., benzenesulfonamido, N-ethyltoluenesulfonamido, heptafluorobutaneamido, 2,3,4,5,6-pentafluorobenzamido, octanesulfonamido, p-cyanophenylureido, N,N-diethylsulfamoylamino, 1-piperidyl, 5,5-dimethyl-2,4-dioxo-3-oxazolidinyl, 1-benzyl-ethoxy-3-hydantoinyl, 2N-1,1-dioxo-3(2H)-oxo-1,2-benzoisothiazolyl, 2-oxo-1,2-dihydro-1-pyridinyl, imidazolyl, pyrazolyl, 3,5-diethyl-1,2,4-triazol-1-yl, 5- or 6-bromo-benzotriazole-1-yl, 5-methyl-1,2,3,4-tetrazol-1-yl, and benzimidazolyl), or a group that links via the sulfur atom (e.g., phenylthio, 2-carboxyphenylthio, 2-methoxy-5-t-octylphenylthio, 4-methanesulfonylphenylthio, 4-octanesulfonamidophenylthio, benzylthio, 2-cyanoethylthio, 1-ethoxycarbonyltridecylthio, 5-phenyl-2,3,4,5-tetrazolylthio, and 2-benzothiazolyl).

As examples of group X in this invention, usual coupling split-off groups can be enumerated.

Of these examples of X, halogen atoms and the groups that link via the sulfur atom are preferable.

When $R_1$, $R_2$, $R_3$, or X is a divalent group to form a bis-form coupler, $R_1$, $R_2$ or $R_3$ represents a substituted or unsubstituted alkylene group (e.g., methylene, ethylene, 1,10-decylene, and $-CH_2CH_2-O-CH_2CH_2-$) or a substituted or unsubstituted phenylene group (e.g., 1,4-phenylene, 1,3-phenylene,

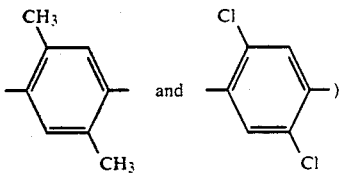

and X represents a divalent group that is formed suitably from the above-described monovalent group.

When a compound represented by formula (I) or (II) is included in a vinyl monomer, the linking group represented by any of $R_1$, $R_2$ or $R_3$ includes the group that is formed by combining those selected from substituted or unsubstituted alkylene groups (e.g., methylene, ethylene, 1,10-decylene, and $-CH_2CH_2OCH_2CH_2-$), substituted or unsubstituted phenylene groups (e.g., 1,4-phenylene, 1,3-phenylene,

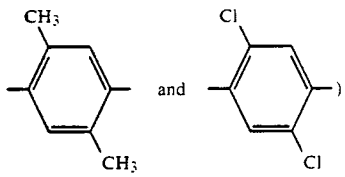

$-NHCO-$, $-CONH-$, $-O-$, and aralkylene groups (e.g.,

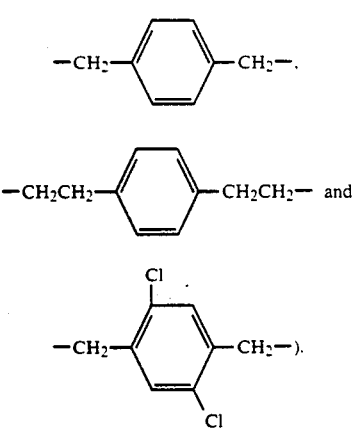

Preferable linking groups include $-CH_2CH_2-$,

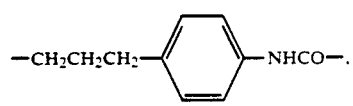

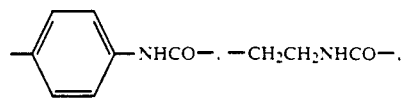

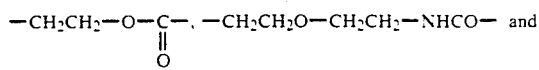

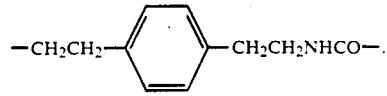

The vinyl groups may have, in addition to those represented by formula (I), substituents, and preferable substituents are a hydrogen atom, a chlorine atom, and a lower alkyl group having 1 to 4 carbon atoms (e.g., methyl and ethyl).

The monomers containing those represented by formulae (I) and (II) may form copolymerized polymers with non-color-forming ethylenically-unsaturated monomers that do not couple with the oxidation products of aromatic primary amine developing agents.

Non-color-forming ethylenically-unsaturated monomers that do not couple with the oxidized products of aromatic primary amine developing agents include acrylic acid, α-chloroacrylic acid, and α-alkylacrylic acids (e.g., methacrylic acid) and the esters and amides derived from these acrylic acids (e.g., acrylamide, n-butylacrylamide, t-butylacrylamide, diacetoneacrylamide, methacrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, and β-hydroxymethacrylate), methylenedibisacrylamide, vinyl esters (e.g., vinyl acetate, vinyl propionate, and vinyl laurate), acrylonitrile, methacrylonitrile, aromatic vinyl compounds (e.g., styrene and its derivatives, vinyltoluene, divinylbenzene, vinylacetophenone, and sulfostyrene), itaconic acid, citraconic acid, crotonic acid, vinylidene chloride, vinyl alkyl ethers (e.g., vinyl ethyl ether), maleic acid, maleic anhydride, maleates, N-vinyl-2-pyrrolidone, N-vinylpyridine, and 2- or 4-vinylpyridine. Two or more of these non-color-forming ethylenically-unsaturated monomers can be used together, for example n-butyl acrylate and methyl acrylate, styrene and methacrylic acid, methacrylic acid and acrylamide, or methyl acrylate and diacetone acrylamide may be used together.

As is well-known in the field of polymer color couplers, non-color-forming ethylenically-unsaturated monomers that are to be copolymerized with solid water-insoluble monomer couplers can be selected in such a way that the physical properties and/or chemical properties of the copolymers, such as, for example, the solubility, the compatibility with the binder of the photographic colloid composition (such as gelatin), and the flexibility and heat stability, are favorably affected.

Although the polymer couplers used in the present invention may be soluble or insoluble in water, polymer coupler latexes are preferable inter alia.

Specific examples of typical magenta couplers in the present invention are given below, but they are not intended to limit the scope of the present invention.
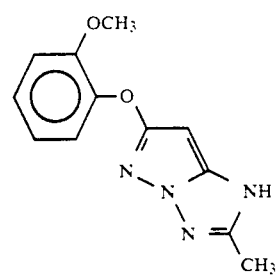
(1)
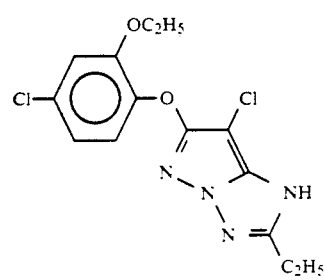
(2)
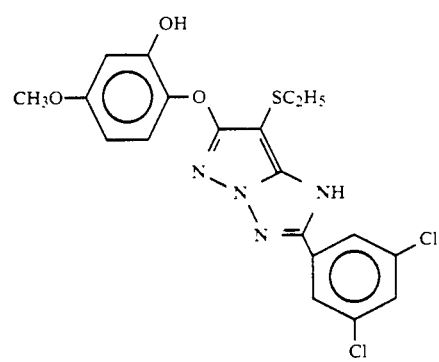
(3)
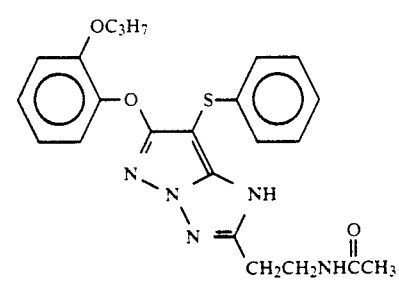
(4)
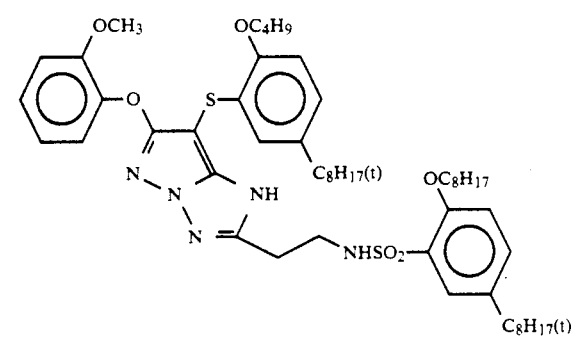
(5)

-continued
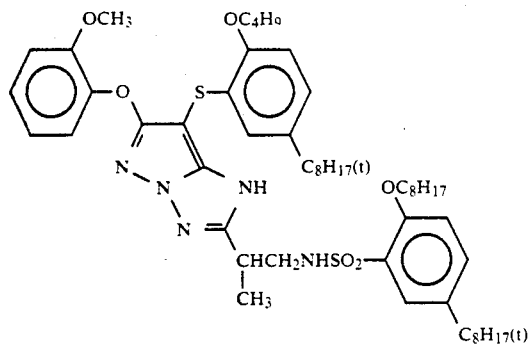
(6)
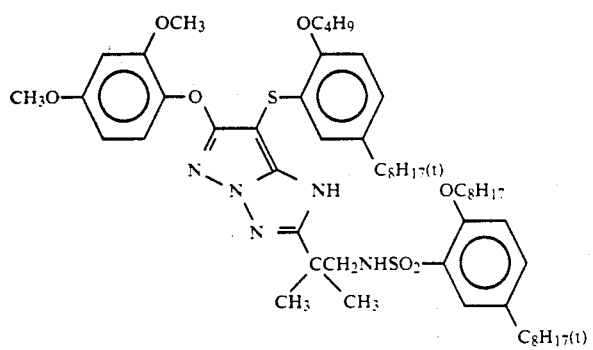
(7)
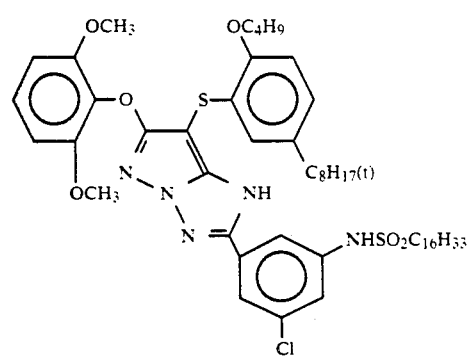
(8)
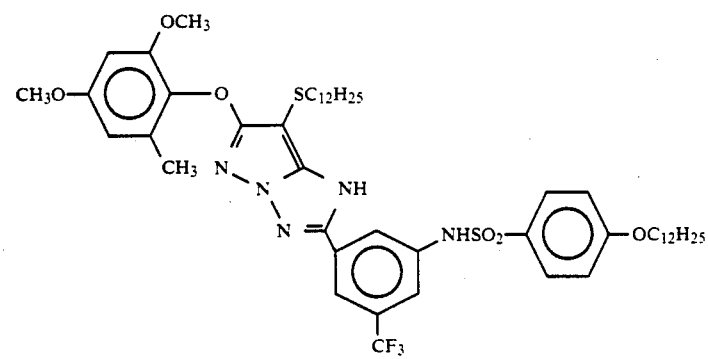
(9)

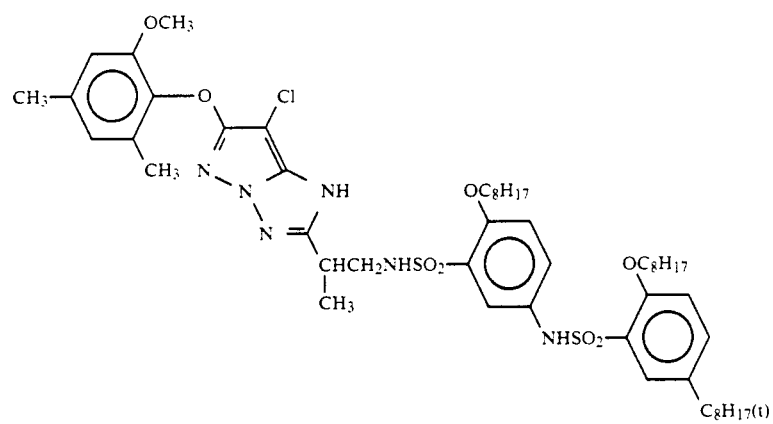
(10)
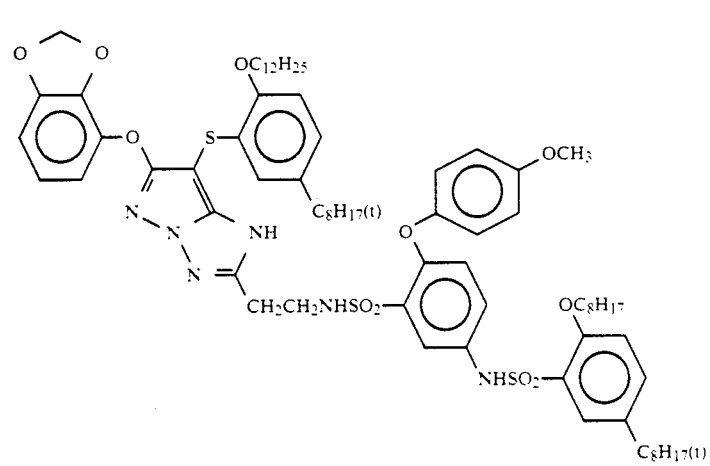
(11)
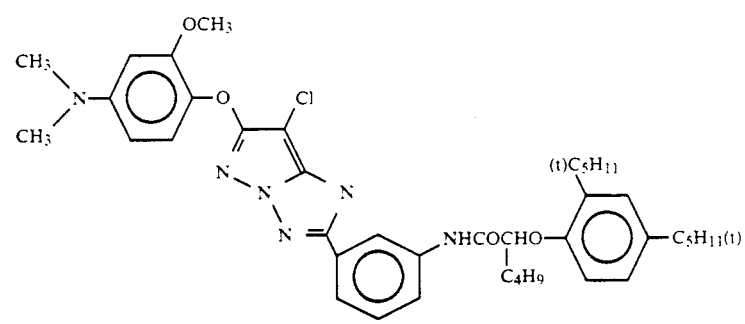
(12)
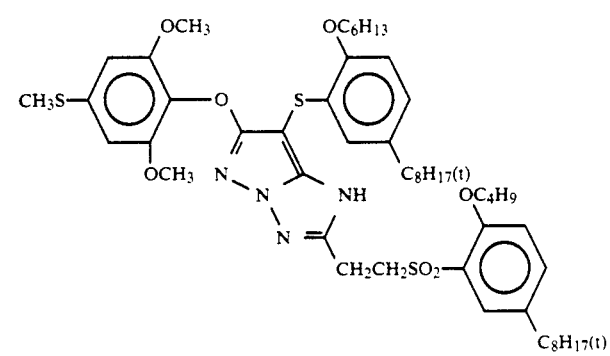
(13)

(14)
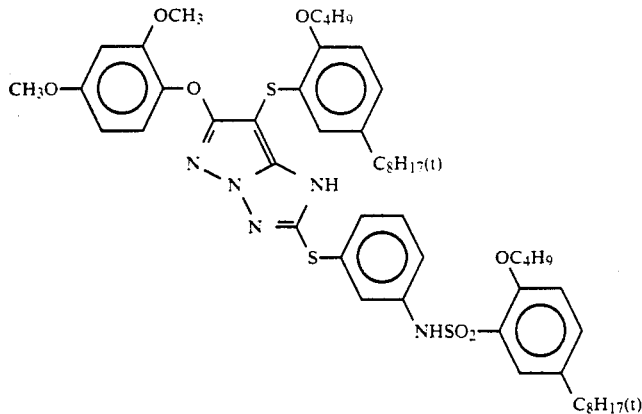
(15)
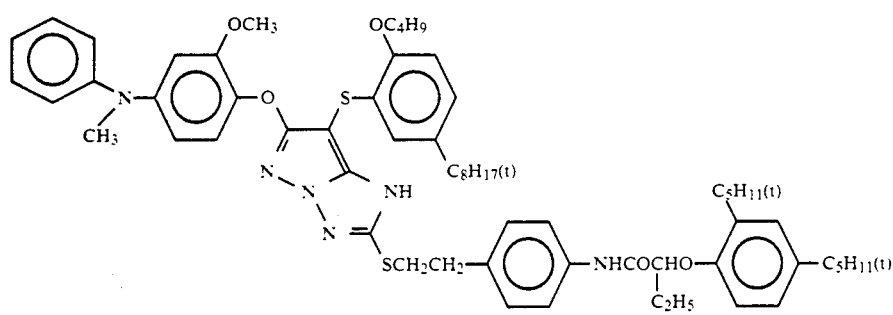
(16)
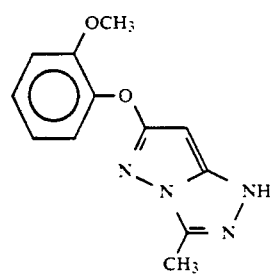
(17)
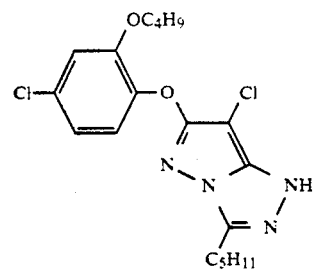
(18)
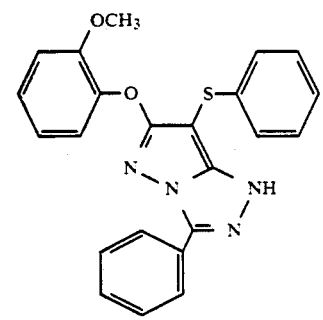

-continued
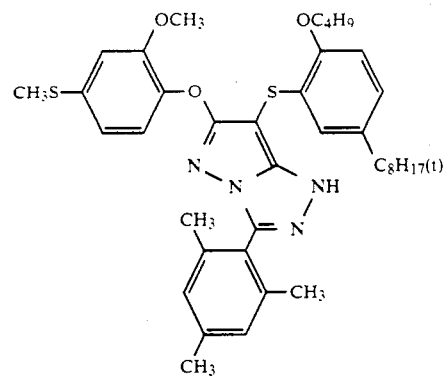
(19)
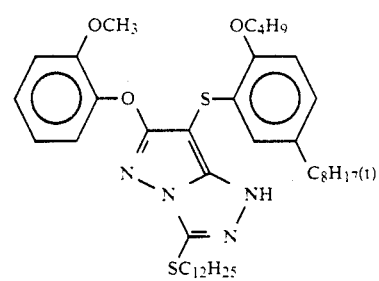
(20)
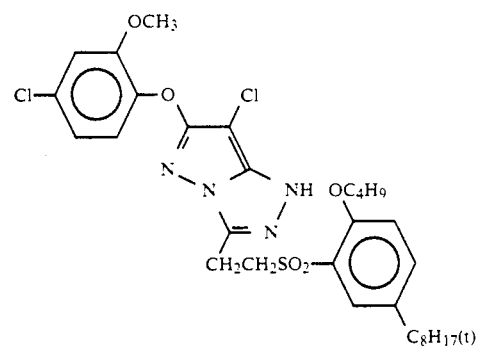
(21)
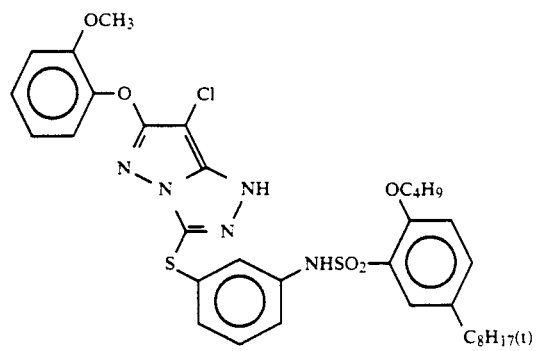
(22)

-continued
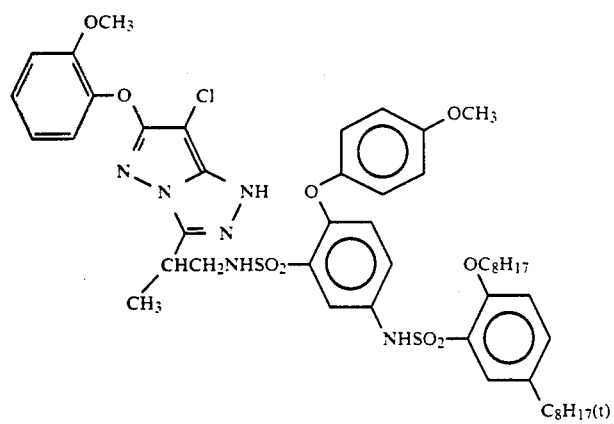
(23)
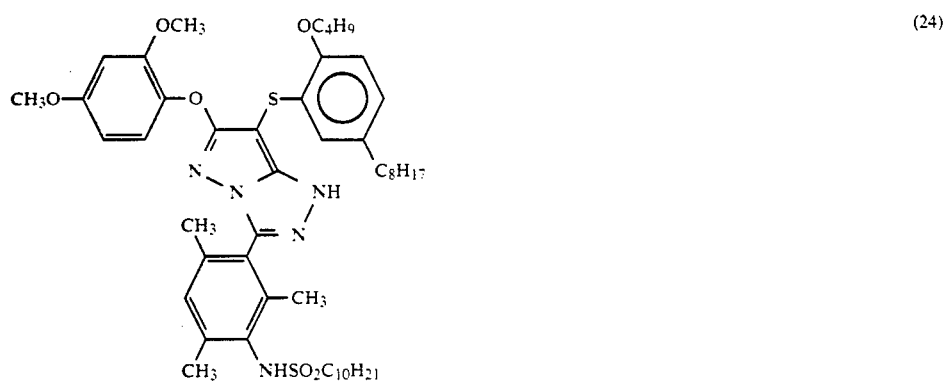
(24)
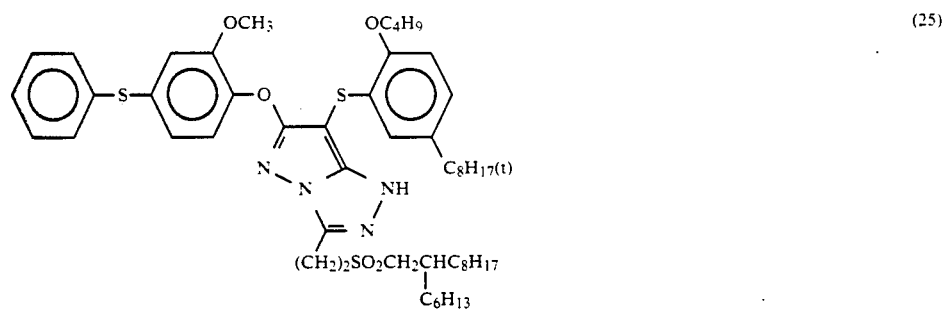
(25)
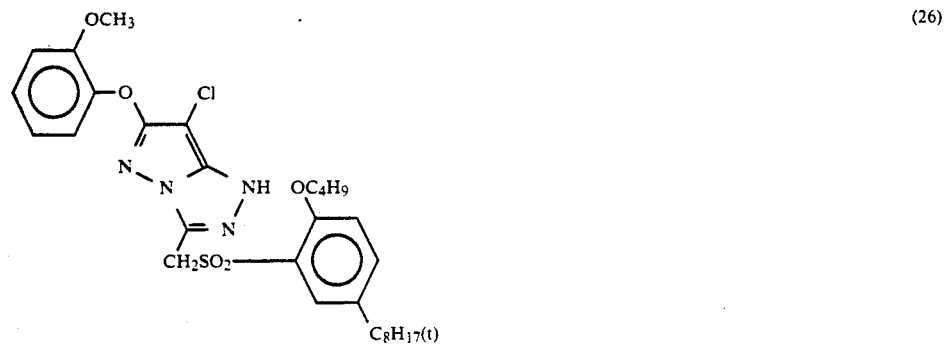
(26)

-continued
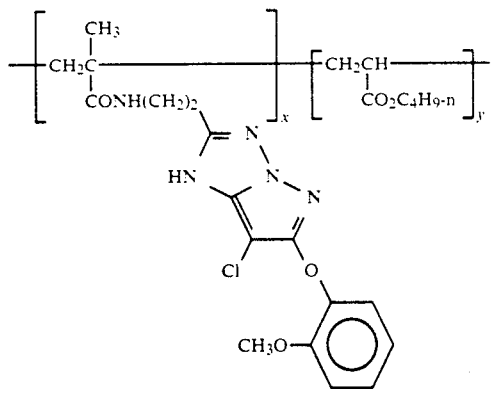
(27)
x:y = 50:50
(in weight ratio, the same rule is applied to hereinafter)
(Molecular weight: about 30,000)
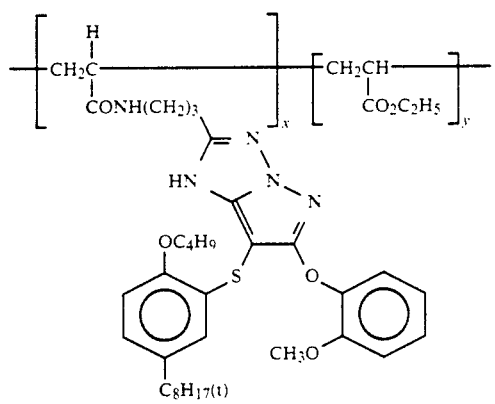
(28)
x:y = 44:55
(Molecular weight: about 30,000)
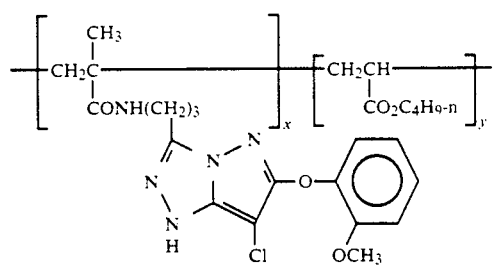
(29)
x:y = 50:50
(Molecular weight: about 30,000)
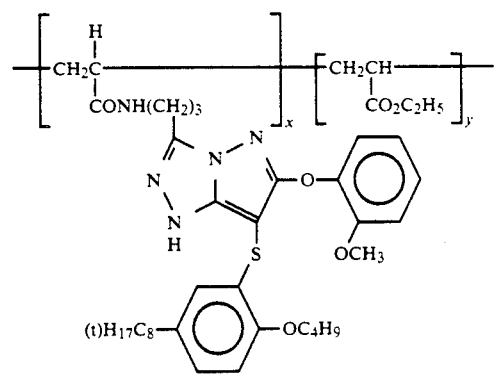
(30)
x:y = 45:55
(Molecular weight: about 30,000)
General synthesis methods of couplers of the present invention will now be described. Although the inventor In the case of 1H-pyrazolo[5,1-c]-1,2,4-triazole couplers (represented by formula (II)), they can be synthesized according to the method based on Japanese Patent Publication No. 30895/1973 and Japanese Patent Application (OPI) No. 2499087/1986 (Scheme 2).

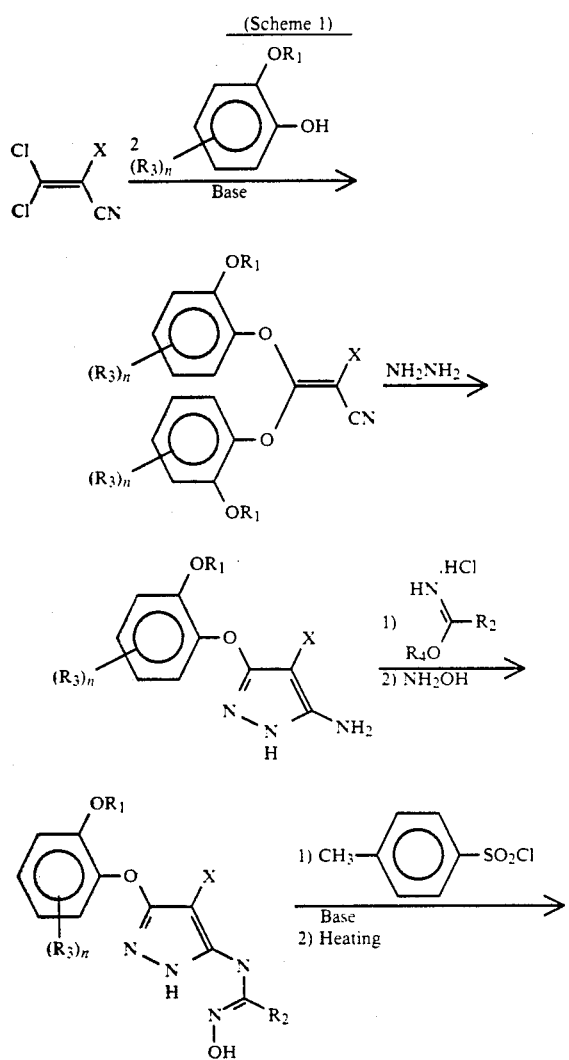

(wherein $R_1$, $R_2$, $R_3$, X and n have the same meaning as described above, and $R_4$ represents an alkyl group or an aryl group.)

(Scheme 2)
(Process A)

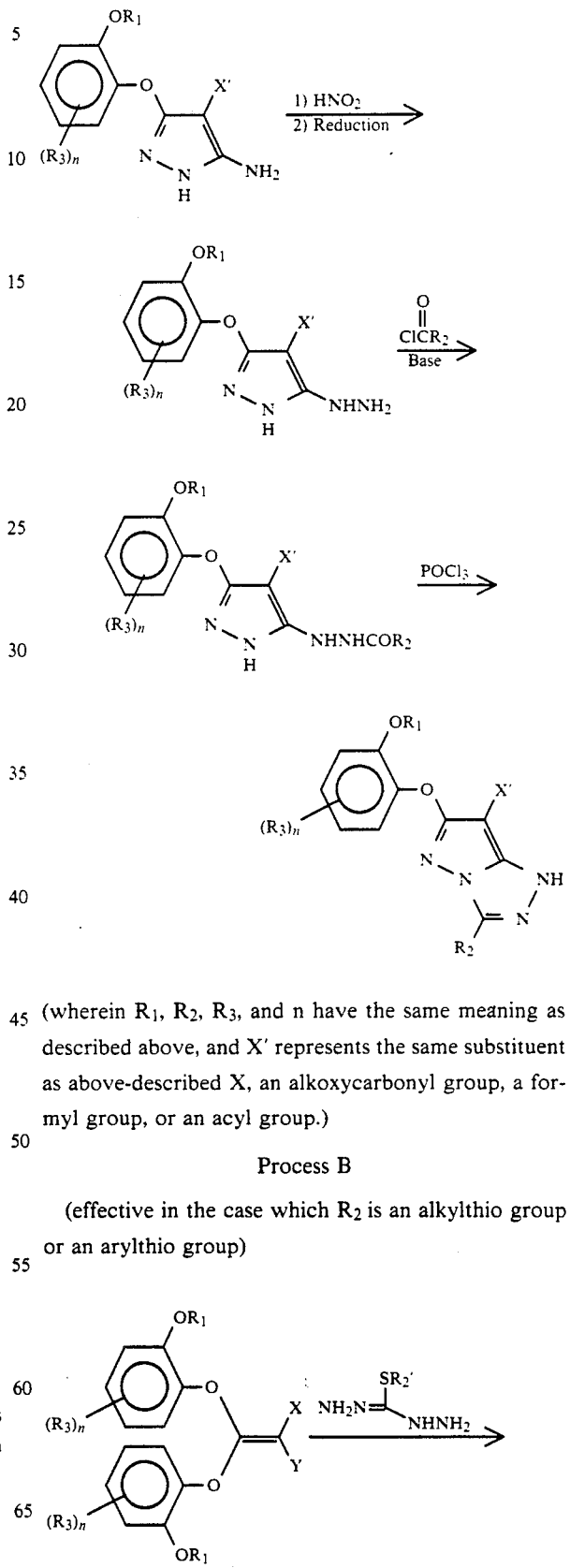

(wherein $R_1$, $R_2$, $R_3$, and n have the same meaning as described above, and X' represents the same substituent as above-described X, an alkoxycarbonyl group, a formyl group, or an acyl group.)

Process B (effective in the case which $R_2$ is an alkylthio group or an arylthio group)

-continued

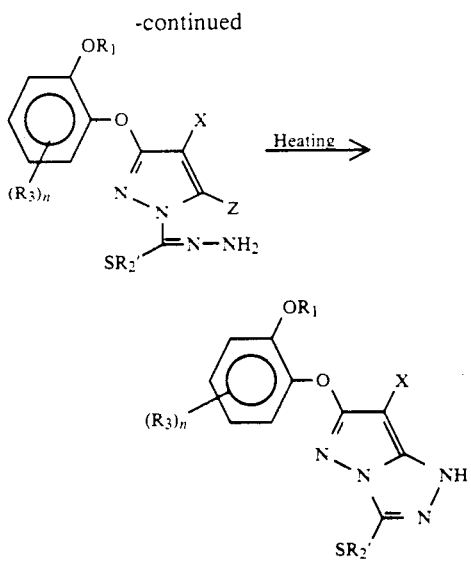

(wherein $R_1$, $R_3$, and X have the same meaning as described above; Y represent a cyano group or an alkoxycarbonyl group; Z represents OH group or $NH_2$ group; and $R_2'$ represents an alkyl group or an aryl group.)

With respect to a synthesis method of polymer couplers, solution polymerization and emulsion polymerization will be described. As solution polymerization, the methods described in U.S. Pat. No. 3,451,820 and Japanese Patent Application (OPI) No. 28745/1983 can be used. That is, a monomer coupler having a portion represented by formula (I) and a non-color-forming ethylenically-unsaturated monomer {e.g., acrylic acids such as acrylic acid, α-chloroacrylic acid, and methacrylic acid, or esters or amides derived from acrylic acids (e.g., acrylamide, n-butyl acrylamide, n-butyl methacrylate, methyl methacrylate, and ethyl methacrylate)} are, in a suitable ratio, dissolved into or mixed with a soluble organic solvent (e.g., dioxane and methyl cellosolve), and polymerization is initiated at a suitable temperature (about 30° to 100° C.) by a physical action, such as radiation by ultraviolet rays or higher energy or by a chemical action of an initiator such as persulfates, hydrogen peroxide, benzoyl peroxide, and azobisalkyronitrile, to form free radicals. After completion of the polymerization reaction, the reaction mixture is extruded into an organic solvent, or condensed, or poured into water, so that the polymer can be isolated. As emulsion polymerization, the method described in U.S. Pat. No. 3,370,952 can be used.

The coupling split-off group may be introduced in the stage of a starting material, or in the stage of an intermediate. General methods of introducing coupling split-off groups after the synthesis of skeletons will next be described.

(1) Method of Linking the Oxygen Atom

A four-equivalent mother nucleus coupler of this invention is formed into a dye as shown in Example 1, and then it is hydrolyzed in the presence of an acid catalyst into a ketone body. This ketone body can be hydrogenated using Pd-carbon as a catalyst or reduced with Zn-acetic acid or sodium boron hydride, thereby synthesizing a 7-hydroxy body. The 7-hydroxy body can be reacted with a halide to synthesize an intended coupler with an oxygen atom linked (see U.S. Pat. No. 3,926,631 and Japanese Patent Application (OPI) No. 70817/1982).

(2) Method of Linking the Nitrogen Atom

The method of linking a nitrogen atom is generally classified into three processes. The first process includes nitrosotizing the coupling-active site with a suitable nitrosotizing agent, as described in U.S. Pat. No. 3,419,391, followed by reducing in a suitable manner (e.g., using a hydrogenation process that employs Pd-carbon or the like as catalyst, or a chemical reduction process that employs stannous chloride or the like) to produce a 7-amino body, and reacting the 7-amino body with a halide, which can produce mainly amide compounds.

The second process comprises the method described in U.S. Pat. No. 3,725,067. That is, the 7-position is halogenated with a suitable halogenating agent such as sulfuryl chloride, chlorine gas, bromine, N-chlorosuccinimide, and N-bromosuccinimide, and then a nitrogen heterocyclic ring is substituted in the presence of a suitable basic catalyst, such as triethylamine, sodium hydride, diazabicyclo[2.2.2]octane, and anhydrous potassium carbonate, by the method described in Japanese Patent Publication 45135/1981, which can synthesize couplers to which the coupling-off group is linked via a nitrogen atom at the 7-position. Of compounds to which a coupling-off group is linked via an oxygen atom, compounds having a phenoxy group at the 7-position can also be synthesized by this process.

The third process is a process that is effective when a 6-π or 10-π electron-type aromatic nitrogen heterocyclic ring is introduced onto the 7-position, and it includes adding, to a 7-halogen body synthesized by the second process mentioned above, as described in Japanese Patent Publication No. 36577/1982, a 6-π or 10-π electron-type aromatic nitrogen heterocyclic ring that is used in a molar amount two or more times as much as the former, and heating the mixture at 50° to 150° C. without any solvents, or in a non-protonic polar solvent such as dimethylformamide, sulfolane, or hexamethylphosphotriamide, which can introduce an aromatic nitrogen heterocyclic group to the 7-position via the nitrogen atom.

(3) Method of Linking the Sulfur Atom

Couplers wherein an aromatic mercapto group or a heterocyclic mercapto group is substituted on the 7-position can be synthesized by the method described in U.S. Pat. No. 3,227,554. That is, by dissolving an arylmercaptan, a heterocyclic mercaptan, and the corresponding disulfide into a halogenated hydrocarbon-type solvent to be converted to a sulphenyl chloride using chlorine or sulfuryl chloride, which is then added to a four-equivalent coupler dissolved in a non-protonic solvent. As methods of introducing an alkylmercapto group to the 7-position, a process described in U.S. Pat. No. 4,264,723, wherein a mercapto group is introduced to the coupling-active position of a coupler and a halide is allowed to act on the the mercapto group, and a process wherein the synthesis is effected in one step by using an S-(alkylthio)isothiourea and a hydrochloride (or a hydrobromide), are effective.

SYNTHESIS EXAMPLE

An exemplified compound (5) having formula (XX) given below of the present invention was synthesized according to the equations given below.

With respect to the method of synthesizing 3,3-dichloroacrylonitrile used in this synthesis example, the following processes can, for example, be mentioned.

3,3-dichloroacrylonitrile can be obtained, in accordance with *Journal of Organic Chemistry*, Vol. 35, page 828 (1970), in a yield of about 50% by heating a gas mixture of carbon tetrachloride and acrylonitrile to 900° C. 3,3-dichloroacrylonitrile can also be obtained by converting chloral to cyanohydrin acetate, in accordance with *Chemische Berichte*, Vol. 10, page 1058 (1877), and then carrying out the reduction using zinc powder, as described in *Tetrahedron*, Vol. 23, page 1145 (1967).

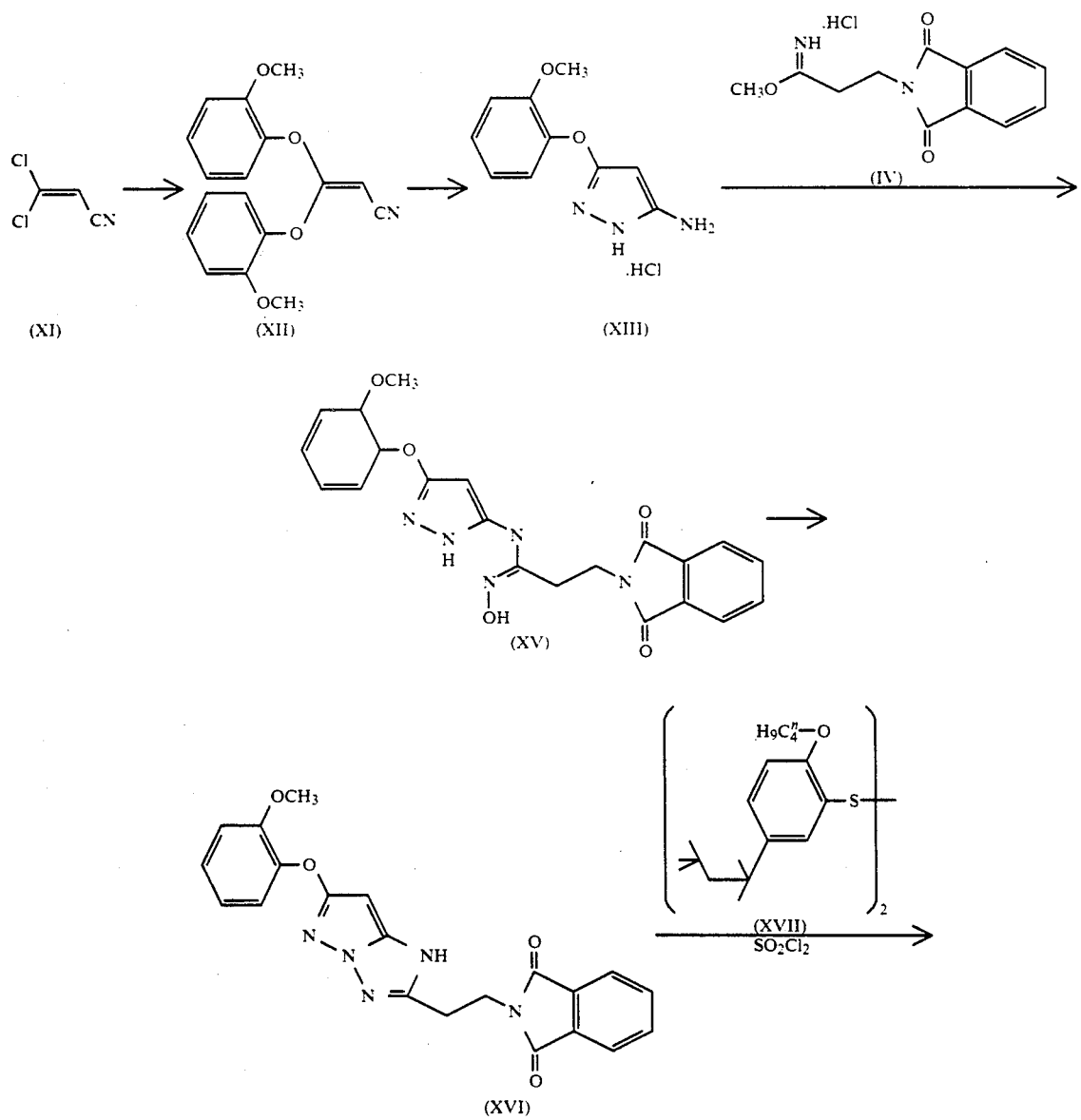

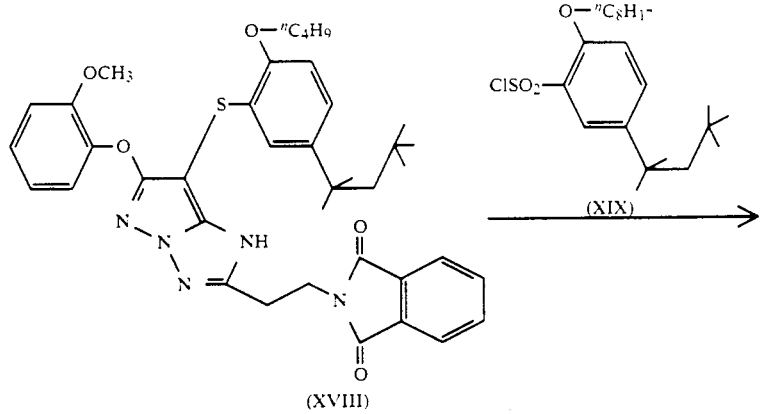

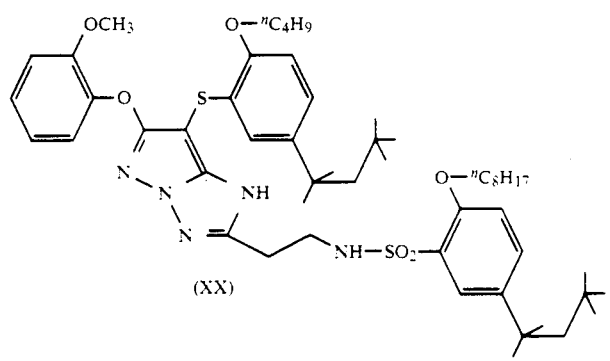

Synthesis of Compound (XII)

358 g of potassium-t-butoxide was added to 2.5 l of t-butanol and stirred at room temperature. 396 g of guaiacol (o-methoxyphenol) was added dropwise to the solution, and the reaction mixture was heated and stirred for 5 min under refluxing conditions. Then 195 g of 3,3-dichloroacrylonitrile (XI) was added dropwise over 30 min, and the reaction mixture was heated and stirred for 5 hours under refluxing conditions. Then, after cooling to 20° C. under water cooling, 1.3 l of water was added, and the resulting crystals were filtered and dried to obtain 313 g (yield: 66%) of compound (XII). Melting point: 115.0°–117.0° C.

NMR (CDCl$_3$): $\delta$ = 6.8 to 7.4 (m, 8H), 3.93 (s, 3H), 3.83 (s, 3H), 3.60 (s, 1H)

Synthesis of Compound (XIII)

90 ml of a 80% aqueous solution of hydrazine hydrate was added to 90 g of compound (XII), and the mixture was heated to 100° C. for 1 hour with stirring. After the reaction mixture was cooled to room temperature, common salt was added thereto, extraction with 540 ml of ethyl acetate was carried out, and then the obtained ethyl acetate layer was washed three times with 180 ml of aqueous saturated common salt solution. After drying over anhydrous sodium sulfate, the extract was kept at 15° C. or below by cooling with ice while blowing 2.2 g of hydrogen chloride gas thereinto, and the obtained crystals were suction-filtered to produce 50 g (yield: 69%) of the desired crystals. Melting point: 185.0°–187.0° C.

NMR (DmSO-d$_6$): $\delta$ = 9.5 (brs, 4H), 6.8 to 7.9 (m, 4H), 4.80 (s, 1H), 3.83 (s, 3H)

Synthesis of Compound (XV)

32.4 g of compound (XIII) was added to 100 ml of methanol, and while the temperature was kept at 5° C. or below, 18.6 ml of triethylamine was added dropwise thereto. Then 54 g of compound (XIV) was added and the reaction mixture was stirred at room temperature for 3 hours and 30 min. On the other hand, 14 g of hydroxylamine hydrochloride was dissolved into 140 ml of methanol, 40 ml of a 28% methanol solution of sodium methoxide was added to the solution, and the produced common salt was filtered. To the resulting solution was added the former reaction solution. Next, after the reaction mixture was stirred for 4 hours and 30 min at room temperature, 300 ml of water was added, and the resulting crystals were filtered off, washed with water, and dried to obtain 48.2 g (yield: 85%) of the desired compound (XV). Melting point: 169.5°–171.0° C.

NMR (DmSO-d$_6$): $\delta$ = 11.60 (brs, 1H), 9.87 (brs, 1H), 8.03 (brs, 1H), 7.87 (s, 4H), 6.7–7.3 (m, 4H), 5.47 (brs, 1H), 3.80 (s, 3H), 3.21 (t, J = 6.0 Hg, 2H), 2.69 (t, J = 6.0 Hg, 2H)

Synthesis of Compound (XVI)

21.1 g of compound (XV) was dissolved in 60 ml of N,N-dimethylacetamide. The internal temperature was kept to 10° C. or below, 9.5 g of p-toluenesulfonyl chloride was added thereto, and then 4.0 ml of pyridine was added dropwise. After the mixture was stirred for 1 hour at room temperature, water was added to obtain an oil. The water was removed by decantation, 10 ml of N,N-dimethylacetamide, then 200 ml of methanol and 4.0 ml of pyridine were added, followed by heating with stirring for 1 hour under refluxing conditions. After the methanol was removed under reduced pressure, water was added to obtain an oil. The water was removed by decantation, methanol was added to the oil, and the resulting crystals were filtered off, followed by drying to obtain 11.3 g (yield: 56%) of the desired compound (XVI). Melting point: 192.0°–193.0° C.

NMR (DmSO-d$_6$): δ=12.68 (brs, 1H), 7.87 (s, 4H), 6.8–7.2 (m, 4H), 5.24 (s, 1H), 3.96 (t, J=~6 Hg, 2H), 3.77 (s, 3H), 3.07 (t, J=~6 Hg, 2H)

Synthesis of Compound (XVIII)

8.0 g of compound (XVII) was added to 40 ml of 1,2-dichloroethane, and 1.0 ml of sulfuryl chloride was added dropwise thereto. After stirring for 10 min, the 1,2-dichloroethane was removed under reduced pressure. On the other hand, 11.3 g of compound (XVI) was dissolved in 30 ml of DmF, and to the resulting solution was added dropwise over 10 min at room temperature the solution of the product obtained above from compound (XVII) and sulfuryl chloride in 10 ml of DmF. After stirring for 30 min water was added to the reaction mixture, and extraction with ethyl acetate was performed. After the ethyl acetate layer was washed with saturated common salt solution, the ethyl acetate layer was condensed under reduced pressure to obtain an oil. 30 ml of acetonitrile was added to the oil, and the resulting crystals were filtered off to obtain 9.8 g (yield: 91%) of the desired compound (XVIII). Melting point: 169.0°–169.5° C.

NMR (CDCl$_3$): δ=10.93 (brs, 1H), 6.5–7.8 (m, 11H), 3.8–4.1 (m, 4H), 3.70 (s, 3H), 3.03 (t, J=6.0 Hg, 2H), 0.7–1.9 (m, 15H), 0.60 (s, 9H)

Synthesis of Compound (XX)

7.0 g of compound (XVIII) was added to 20 ml of isopropyl alcohol, and after 0.75 ml of 80% hydrazine hydrate was added dropwise thereto the mixture was heated for 3 hours under refluxing conditions with stirring. After the solvent was distilled off under reduced pressure, 30 ml of N,N-dimethylacetamide was added, and 5.0 g of compound (XIX) and then 1.66 ml of triethylamine were added dropwise at room temperature. After the mixture was stirred for 1 hour, water and ethyl acetate were added thereto, the deposited phthalhydrazine was separated by filtration, and the filtrate was extracted. After the resulting ethyl acetate layer was washed with saturated common salt solution, the ethyl acetate layer was dried over anhydrous sodium sulfate, and then condensed.

3 ml of ethyl acetate was added to the residue to dissolve it, then 300 ml of n-hexane was added to the solution followed by stirring, and the resulting crystals were filtered off. 3 ml of ethyl acetate was added to the obtained crystals to dissolve them, and then 200 ml of n-hexane was added for recrystallization, to obtain 6.6 g (yield: 69%) of the desired compound (XX). Melting point: 100.0°–101.0° C.

NMR (CDCl$_3$): δ=10.30 (brs, 1H), 6.5–7.9 (m, 10H), 5.50 (t, J=6.0 Hg, 1H), 3.8–4.2 (m, 4H), 3.73 (s, 3H), 29.34 (m, 2H), 2.6–2.9 (m, 2H), 0.7–1.9 (m, 38H), 0.70 (s, 9H), 0.60 (s, 9H)

When a silver halide photographic material is developed with a color-developing solution containing an aromatic primary amine-type developing agent in the presence of at least one of magenta couplers represented by formula (I) or (II) of the present invention, a color image can be formed.

Preferably, the color-developing solutions that can be used for magenta couplers of the present invention are alkaline aqueous solutions that contain as a major component an aromatic primary amine-type color-developing agent. As typical examples of the color-developing agents can be mentioned 4-amino-N,N-diethylaniline, 3-methyl-4-N,N-diethylaniline, 4-amino-N-ethyl-N-β-hydroxydiethylaniline, 3-methyl-4-amino-N-ethyl-β-hydroxyethylaniline, 3-methyl-4-amino-N-ethyl-N-β-methanesulfonamidoethylaniline, and 4-amino-3-methyl-N-ethyl-N-β-methoxyethylaniline.

The color-developing solution may, for example, contain pH buffers, such as zincates, carbonates, borates, and phosphates of alkali metals; and development restrainers or antifoggants, such as organic antifoggants, bromide, and iodides. If necessary, the color-developing solution may contain, for example, water softeners; preservatives such as hydroxylamine; organic solvents such as benzyl alcohol and diethylene glycol; development accelerators such as amines, quaternary ammonium salts, and polyethylene glycols; dye-forming couplers; competing couplers; fogging agents such as sodium boron hydride; auxiliary developing solutions such as 1-phenyl-3-pyrazolidone; thickening agents; polycarboxylic acid-type chelate agents described in U.S. Pat. No. 4,083,723; and antioxidants described in German Patent Application (OLS) No. 2,622,950.

When the magenta color image formed from the magenta coupler used in the present invention is used together with a color image stabilizer represented by the following formula, the fastness to light is improved.

Formula:

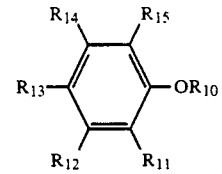

wherein $R_{10}$ represents a hydrogen atom, an alkyl group, an aryl group, or a heterocyclic group; $R_{11}$, $R_{12}$, $R_{13}$, $R_{14}$, and $R_{15}$ each represent a hydrogen atom, a hydroxyl group, an alkyl group, an aryl group, an alkoxy group, an acylamino group, an alkoxycarbonyl group, or a sulfonamido group; $R_{13}$ represents an alkyl group, a hydroxyl group, an aryl group, or an alkoxy group; $R_{10}$ and $R_{11}$ may close together to form a 5- or 6-membered ring, or they may close to form a methylenedioxy ring; and $R_{13}$ and $R_{14}$ may close to form a 5-membered hydrocarbon ring.

These compounds include compounds described in U.S. Pat. Nos. 3,935,016, 3,982,944, and 4,254,216, Japanese Patent Application (OPI) Nos. 21004/1980, and 145530/1979, British Patent Application (OPI) Nos. 2,077,455, and 2,062,888, U.S. Pat. Nos. 3,764,337, 3,432,300, 3,574,627, and 3,573,050, Japanese Patent Application (OPI) Nos. 152225/1977, 20327/1978, 17729/1978, and 6321/1980, British Patent No. 1,347,556, British Patent Application (OPI) No. 2,066,975, Japanese Patent Publication Nos. 12337/1979, and 31625/1973, U.S. Pat. No. 3,700,455, and Japanese Patent Application (OPI) No. 90155/1986.

The preferred embodiments of this invention include a silver halide color photographic material that contains the couplers of this invention.

The couplers of this invention may be added to either a photographic material or a color-developing bath solution.

The couplers of this invention is added at least on a photographic emulsion layer of the photographic material, and may be added to an arbitrary layer such as a highly sensitive layer or an intermediate sensitive layer, or the adjacent layer to such layers. The amount of coupler to be added to a photographic material may be $2 \times 10^{-3}$ to $5 \times 10^{-1}$ mol, preferably $1 \times 10^{-2}$ to $5 \times 10^{-1}$ mol, per mol of silver halide. In the case of polymer couplers, the amount to be added may be adjusted so that the coloring moiety of the polymer coupler corresponds to the above-mentioned amount. When adding to a color-developing bath solution, a suitable amount is 0.001 to 0.1 mol, preferably 0.01 to 0.05 mol, per 1000 ml of the bath solution.

The pyrazoloazole system couplers of this invention can be introduced into a photographic material by any one of various known dispersing methods, typically, for example, by the solid dispersing method, the alkali dispersing method, or preferably the latex dispersing method, or most preferably the oil-in-water dispersing method. According to the oil-in-water dispersing method, dispersants are first dissolved in a single or mixed solvent of a high-boiling (having a boiling point of 175° C. or higher) organic solvent, or a low-boiling (auxiliary) organic solvent, and then dispersed as fine particles in an aqueous medium, e.g., water or an aqueous gelatine solution, in the presence of surface-active agents. Examples of high-boiling organic solvents are described in U.S. Pat. No. 2,322,027. For dispersing, phase reversal of the emulsion can be utilized. If necessary, prior to coating the auxiliary solvent may be removed or reduced by distillation, "noodle" washing, or ultrafiltration.

Examples of high-boiling organic solvents include phthalic esters (e.g., dibutyl phthalate, dicyclohexyl phthalate, di-2-ethylhexyl phthalate, and decyl phthalate), phosphoric or phosphonic esters (e.g., triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, and di-2-ethylhexylphenyl phosphonate), benzoic esters (e.g., 2-ethylhexylbenzoate, dodecyl benzoate, and 2-ethylhexyl-p-hydroxy benzoate), amides (e.g., diethyldodecanamide and N-tetradecylpyrrolidone), alcohols or phenols (e.g., isostearyl alcohol and 2,4-di-tert-amylphenol), aliphatic carboxylic esters (e.g., dioctylazelate, glycerol tributyrate, isostearyl lactate, and trioctyl citrate), aniline derivatives (e.g., N,N-dibutyl-2-butoxy-5-tert-octyl-aniline), and hydrocarbons (e.g., paraffin, dodecylbenzene, and diisopropylnaphthalene). The auxiliary solvents are organic solvents having a boiling point higher than about 30° C., preferably from about 50° C. to below about 160° C. Examples of these solvents include ethyl acetate, butyl acetate, ethyl propionate, methylethyl ketone, cyclohexanone, 2-ethoxyethyl acetate, and dimethylformamide.

The steps and effect of the latex dispersion method and the examples of latex for impregnation are disclosed in U.S. Pat. No. 4,199,363 and West German Patent Application (OLS) Nos. 2,541,274 and 2,541,230.

Representative examples of the silver halide emulsion for use in this invention include, in addition to silver chloride and silver bromide, mixed silver halide, such as silver chlorobromide, silver chloroiodobromide, and silver iodobromide. The silver halide preferably used in this invention is silver chloroiodobromide, silver chlorobromide, or silver iodobromide, each containing silver iodide of 3 mol % or less, silver chloride, silver bromide, or silver chlorobromide. The silver halide grains may be of such a structure that the internal phase differs from the surface phase, the entire grains may have a uniform phase, they may be polyphase with a joining structure, or a mixture thereof.

The average size of the silver halide grains, expressed in terms of the grain diameter for spherical or semi-spherical grains and the edge length for cubic grains, can be determined as the average of the projected area diameter, and it is preferably smaller than 2 μm and larger than 0.1 μm, most preferably smaller than 1 μm and larger than 0.15 μm. The so-called "monodisperse emulsion" of silver halide that has a narrow distribution range of grain size, wherein at least 90%, in particular at least 95%, of the number or weight of the silver halide grains are within ±40% of the average grain diameter, may be employed in the present invention. In order to realize the gradation desired for the photographic material, two or more monodisperse silver halide emulsions different in grain size may be mixed in a single layer or coated as different layers that have substantially the same color sensitivity. Further, two or more polydisperse silver halide emulsions or a combination of monodisperse and polydisperse emulsions can be employed as a mixture in one layer, or coated as different layers.

Silver halide grains for use in this invention may have a regular crystal structure, such as cubic, hexahedral, rohmbic dodecahedral, or tetradecahedral; an irregular crystal structure, such as spherical; or a thereof composite crystal structure. Tabular grains may be employed wherein at least 50% of the total projected area of silver halide grains is tabular grains with a diameter-to-thickness ratio (of 5 or more, particularly of 8 or more). Silver halide emulsions may be a mixture of various crystal structures. Silver halide grains may be used that form a latent image primarily on the grain surface or in the interior of the grains.

The photographic emulsion for use in this invention can be prepared by processes described in P. Glafkides, "Chimie et Physique Photographique" (Paul Montel, 1967), G. F. Duffin, "Photographic Emulsion Chemistry" (The Focal Press, 1966), V. L. Zelikman et al. "Making and Coating photographic Emulsions" (The Focal Press, 1964), etc. Any one of an acidic process, a neutral process, and an ammoniacal process can be used. As a means of reacting a soluble silver salt with a soluble halide salt, any of the single jet method, double jet method, or a combination thereof may be employed.

A process of forming grains in the presence of excess silver ion (the so-called reversal mixing process) can be employed as well. As one type of double jet method, the "controlled double jet" process can be employed, wherein the pAg in the liquid phase of the silver halide formation is kept constant. This process provides a silver halide emulsion containing regular silver halide grains having an approximately monodisperse particle size.

During formation or physical ripening of the silver halide grains, cadmium salts, zinc salts, lead salts, thallium salts, iridium salts or complex salts thereof, rhodium salts or complex salts thereof, iron salts or complex salts thereof, etc., may also be present.

The silver halide emulsion may generally be physically ripened, chemically ripened, and spectrally sensitized. Additives that will be used in these steps are described in *Research Disclosure* No. 17643 and ibid. No. 18716, and the involved sections are listed in the Table below.

Known photographic additives that can be used in this invention are also described in the above-mentioned two Research Disclosures, and the involved sections are listed in the same Table below.

| Additive | RD 17643 | RD 18716 |
| --- | --- | --- |
| 1 Chemical sensitizer | p. 23 | p. 648 (right column) |
| 2 Sensitivity-enhancing agents | — | " |
| 3 Spectral sensitizers and Supersensitizers | pp. 23-24 | pp. 648 (right column)-649 (right column) |
| 4 Brightening agents | p. 24 | — |
| 5 Antifogging agents and Stabilizers | pp. 24-25 | p. 649 (right column) |
| 6 Light absorbers, Filter dyes, and UV Absorbers | pp. 25-26 | pp. 649 (right column)-650 (left column) |
| 7 Stain-preventing agents | p. 25 (right column) | p. 650 (left to right column) |
| 8 Image-dye stabilizers | p. 25 | — |
| 9 Hardeners | p. 26 | p. 651 (left column) |
| 10 Binders | p. 26 | " |
| 11 Plasticizers and Lubricants | p. 27 | p. 650 (right column) |
| 12 Coating aids and Surface-active agents | pp. 26-27 | " |
| 13 Antistatic agents | p. 27 | " |

Various color couplers can be used in the present invention, and examples thereof are described in patents cited in *Research Disclosure* No. 17643, VII-C to VII-G. As dye-forming couplers, couplers capable of developing three primary colors of the substractive color process (i.e., yellow, magenta, and cyan) by color development are important, and specific examples of nondiffusible 4-equivalent or 2-equivalent couplers are couplers disclosed in patents cited in the above-mentioned *Research Disclosure* No. 17643, VII-C and VII-D. In addition, the following couplers can be employed favorably in the present invention.

Representative examples of yellow couplers useful in the present invention include couplers of the hydrophobic acylacetoamide type that have a ballast group, as described in U.S. Pat. Nos. 2,407,210, 2,875,057, and 3,265,506. Typical examples of two-equivalent yellow couplers preferable in this invention include yellow couplers having an oxygen-linked coupling split-off group, as illustrated in U.S. Pat. Nos. 3,408,194, 3,447,928, 3,933,501, and 4,022,620, and yellow couplers having a nitrogen-linked coupling split-off group, as illustrated in Japanese Patent Publication No. 10739/1983, U.S. Pat. Nos. 4,401,752 and 4,326,024, *Research Disclosure* No. 18053 (April 1979), British Patent No. 1,425,020 and German Patent (OLS) Nos. 2,219,917, 2,261,361, and 2,433,812. Couplers of the α-pivaloyl-acetoanilide type are superior in the fastness of formed dye, particularly on exposure to light, while couplers of the α-benzoylacetoanilide type are capable of forming high maximum density.

Magenta couplers useful in combination with pyrazoloazole coupler for this invention include hydrophobic couplers having a ballasted group of the indazolone or cyanoacetyl type, preferable of the 5-pyrazolone type. 5-Pyrazolones substituted by an arylamino or acylamino group at the 3-position are preferable in view of the hue and maximum densities of formed dyes, and they are described in U.S. Pat. Nos. 2,311,082, 2,343,703, 2,600,788, 2,908,573, 3,062,653, 3,152,896, and 3,936,015. Preferable coupling split-off groups in the two-equivalent 5-pyrazolone couplers are nitrogen-linked coupling split-off groups described in U.S. Pat. No. 4,310,619, and an arylthio group described in U.S. Pat. No. 4,351,897. The 5-pyrazolone-type couplers that contain a ballast group described in European Patent No. 73,636 have effects to enhance developed density.

The cyan couplers that can be used in this invention include naphthol couplers and phenol couplers of the hydrophobic and nondiffusible type. An example of a naphthol coupler is that disclosed in U.S. Pat. No. 2,474,293, and preferred examples of naphthol couplers are such two-equivalent naphthol couplers as the oxygen atom splitting-off type disclosed in U.S. Pat. Nos. 4,052,212, 4,146,396, 4,228,233, and 4,296,200. Examples of phenol couplers are those disclosed in U.S. Pat. Nos. 2,369,929, 2,801,171, 2,772,162, and 2,895,826.

Examples of cyan couplers stable to moisture and heat that can be advantageously employed in this invention include phenol cyan couplers having a higher alkyl group than ethyl group at the meta position of the phenol nucleus, as disclosed in U.S. Pat. No. 3,772,002; 2,5-diacylamino-substituted phenol cyan couplers, as disclosed in U.S. Pat. Nos. 2,772,162, 3,758,308, 4,126,396, 4,334,011, and 4,327,173, German Patent (OLS) 3,329,729 and European Patent No. 121,365; and phenol cyan couplers having a phenylureido group at the 2-position and an acylamino group at the 5-position, as disclosed in U.S. Pat. Nos. 3,446,622, 4,333,999, 4,451,559, and 4,427,767.

It is possible to improve the graininess by using color couplers in combination with a coupler that forms a dye having a proper degree of diffusion. A magenta coupler of such dye-diffusing type is disclosed in U.S. Pat. No. 4,366,237 and British Patent No. 2,125,570; and a similar type of yellow, magenta, or cyan coupler is disclosed in European Patent No. 96,570 and German Patent (OLS) No. 3,234,533.

The dye-forming couplers and the special couplers described above may be dimeric, oligomeric, or polymeric. Examples of polymerized dye-forming couplers are disclosed in U.S. Pat. Nos. 3,451,820 and 4,080,211. Examples of polymerized magenta couplers are disclosed in British Patent No. 2,102,173 and U.S. Pat. No. 4,367,282.

Couplers that will release a photographically useful residue along with the coupling reaction can also be used preferably in the present invention. As DIR couplers that will release a development restrainer, couplers described in patents described in *Research Disclosure* No. 17643, VII-F are useful.

The color photographic materials according to the present invention may be subjected to the usual development processing, such as described in the above-mentioned *Research Disclosure* No. 17643, pp. 28 to 29, and ibid. No. 18716, the left column to the right column on p. 651.

The color photographic materials of the present invention are normally subjected to a washing process or stabilizing process after the development and bleach-fixing or fixing process.

The washing is usually performed in the countercurrent manner using two or more vessels to save water. The washing step may be replaced by the multistage countercurrent stabilizing step, as disclosed in Japanese Patent Application (OPI) No. 8543/1982. This step requires 2 to 9 countercurrent baths incorporated with a variety of compounds for the stabilization of photographic images. Examples of the additives are buffers to adjust the pH of the gelatin emulsion to pH 3-9. (The buffers are prepared by combining boric acid, metaboric acid, borax, phosphate, carbonate, potassium hydroxide, aqueous ammonia, monocarboxylic acid, dicarboxylic acid, polycarboxylic acid, etc. with one another.) Other additives are chelating agents (e.g., inorganic phosphoric acid, aminopolycarboxylic acid, organic phosphoric acid, organic phosphonic acid, aminopolysulfonic acid, and phosphonocarboxylic acid), antiseptic agents (e.g., benzoisothiazolinone, isothiazolone, 4-thiazolinebenzimidazole, halogenated phenol sulfonyl amide and benzotriazole), surface-active agents, fluorescent brighteners, and hardening agents. Two or more additives for the same purpose may be used together.

In order to adjust the pH of the emulsion after processing, it is preferable to add an ammonium salt such as ammonium chloride, ammonium nitrate, ammonium sulfate, ammonium phosphate, ammonium sulfite, and ammonium thiosulfate.

The present invention may be applied to a variety of photographic materials. Typical examples of the silver halide color photographic materials of the present invention include general color negative film or movie color negative film, color reversal film for slides or television, color printing paper, colorpositive film and color reversal printing paper. The photographic material can be prepared in the same manner as the usual photographic materials except the use of the magenta couplers as described above.

The photographic materials comprising the magenta coupler of the present invention exhibit superior photographic characteristics in any of sensitivity, gradation, and color density when compared with that containing the pyrazolotriazole couplers which have an alkyl group at 6-position. Further the photographic material can be prepared at a low cost since the employed magenta coupler is stable and synthesized easily by large-scaled production.

The present invention will now be further described in detail with reference to the following Examples. The structural formulae of the comparative compounds ① and ② used in preparing comparative samples in the Examples are given below (they are described in European Patent Application (OPI) No. 76,804).

Comparative compound ①:

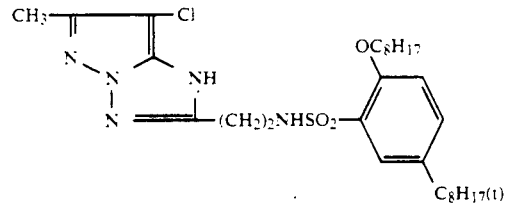

Comparative compound ②:

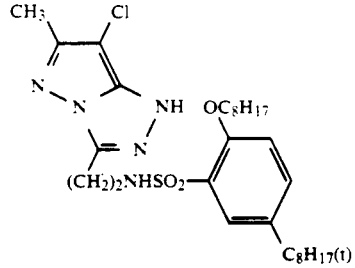

EXAMPLE 1

20 ml of tri(2-ethylhexyl)phosphate, and 25 ml of ethyl acetate were added to 15.9 g (16.8 mmol) of exemplified compound (5) as a magenta coupler, and the resultant mixture was warmed to dissolve the exemplified compound (5). Then the mixture was added to 100 ml of an aqueous solution containing 10 g of gelatin and 1.0 g of sodium dodecylbenzene sulfonate, followed by stirring at a high temperature to obtain a finely emulsified dispersion. All of the emulsified dispersion was added to 100 g (containing 6.5 of Ag) of a silver chlorobromide emulsion containing 30 mol % of Br, then 10 ml of 2% 2,4-dihydroxy-6-chloro-s-triazine sodium salt was added as a hardening agent and the resulting mixture was applied to a double-sided polyethylene-laminated paper base, so that the coating amount of silver might be 200 mg/m², and then a gelatin layer was applied onto the top of the coated layer to prepare photographic material Sample I-A.

Then the above procedure was repeated, except that exemplfied compound (5) as the magenta coupler was replaced with an equal mol of exemplified compound (6), (7), (8), (10), (11), (12), (13), (14), (19), (20), (22), (23), (24), or (25), to prepare Samples I-B to I-O.

Further, a coating sample was prepared by dissolving 8.9 g (16.8 mmol) of comparative compound ① mentioned above in 18 ml of tri(2-ethylhexyl)phosphate and 25 ml of ethyl acetate using the same procedure as described above, thereby preparing a coated sample named comparative sample ①.

Similarly, comparative sample ② was prepared using 8.9 g of comparative compound ② mentioned above.

Samples I-A to I-O as well as comparative samples ① and ② were subjected to exposure through an optical wedge at 1000 C.M.S., and then processed with the following processing solutions.

| Developing Solution | |
| --- | --- |
| Benzyl alcohol | 15 ml |
| Diethylenetriaminepentaacetic acid | 5 g |
| KBr | 0.4 g |
| Na₂SO₃ | 3 g |
| Na₂CO₃ | 30 g |
| Hydroxylamine sulfate | 2 g |
| 4-Amino-3-methyl-N-β-(methanesulfonamido)-ethylaniline.3/2H₂SO₄.H₂O | 4.5 g |
| Water to make | 1000 ml |
| pH: 10.1 | |
| Bleach-Fixing Solution | |
| Ammonium thiosulfate (70 wt. %) | 150 ml |
| Na₂SO₃ | 5 g |
| Na[Fe(EDTA)] | 40 g |
| EDTA.2Na | 5 g |
| Water to make | 1000 ml |
| pH: 6.8 | |

| Processing Steps | Temperature | Time |
| --- | --- | --- |
| Developing | 33° C. | 3 min 30 sec |
| Bleach-fixing | 33° C. | 1 min 30 sec |
| Washing | 28 to 35° C. | 3 min |

The thus-processed samples afforded magenta color images that were sharp and high in saturation. The photographic characteristics of these color images were determined, and the results are shown in Table 1.

TABLE 1

| | Characteristic values | | |
| --- | --- | --- | --- |
| Sample | Sensitivity (S)* | Gradation (γ)** | Maximum density (Dm) |
| Comparative sample ① | 100 | 2.92 | 2.75 |
| Comparative sample ② | 98 | 2.88 | 2.74 |
| I-A | 117 | 3.20 | 2.82 |
| I-B | 116 | 3.19 | 2.85 |
| I-C | 117 | 3.20 | 2.80 |
| I-D | 118 | 3.21 | 2.80 |
| I-E | 111 | 3.14 | 2.82 |
| I-F | 113 | 3.05 | 2.83 |

TABLE 1-continued

| | Characteristic values | | |
| --- | --- | --- | --- |
| Sample | Sensitivity (S)* | Gradation (γ)** | Maximum density (Dm) |
| I-G | 114 | 3.11 | 2.81 |
| I-H | 113 | 3.08 | 2.91 |
| I-I | 112 | 3.20 | 2.82 |
| I-J | 105 | 3.11 | 2.77 |
| I-K | 107 | 3.21 | 2.76 |
| I-L | 111 | 3.08 | 2.78 |
| I-M | 109 | 3.11 | 2.77 |
| I-N | 110 | 3.06 | 2.81 |
| I-O | 111 | 3.09 | 2.80 |

*The relative sensitivity is a relative value, assuming the sensitivity of comparative sample ① with a color-developing time of 3 min. 30 sec. to be 100.
**The gradation (γ) shows the gradient of the sensitometry from a density of 0.6 to a density of 2.5.

As is apparent from the results in Table 1, the photographic material samples of the present invention exhibited superior characteristics in any of sensitivity, gradation, and color density compared to that for couplers that have an alkyl group at the 6-position. Further, when, instead of exemplified compound (5), exemplified compound (27) was used with the coupler unit being in the same amount, excellent results were similarly obtained.

EXAMPLE 2

Sample II-A was prepared according to the following process.

Emulsions for the red-sensitive emulsion layer were prepared as follows:

30 g of lime-treated gelatin was added to 1000 ml of distilled water, and, after the gelatin was dissolved at 40° C., the pH was adjusted to 3.8 with sulfuric acid and 6.5 g of sodium chloride and 0.02 g of N,N'-dimethylethylenethiourea were added, after which the temperature was raised to 75° C. To the resulting solution were added a solution of 62.5 g of silver nitrate in 750 ml of distilled water and a solution of 35.0 g of potassium bromide and 4.3 g of sodium chloride in 500 ml of distilled water, over a period of 40 min with the temperature kept at 75° C. When the obtained emulsion was observed with an electron microscope, it was found that cubic grains having an average side length of about 0.43 μm were formed. Further, a solution of 62.5 g of silver nitrate in 500 ml of distilled water and a solution of 26.3 g of potassium bromide and 8.6 g of sodium chloride in 300 ml of distilled water were added to the emulsion over a period of 20 min at 65° C. When the thus-prepared emulsion was observed with an electron microscope, it was found that cubic grains having an average side length of about 0.55 μm were formed. When the grain size distribution of the emulsion was measured, it was found that the emulsion was a monodisperse emulsion, wherein about 87% (this numerical value is hereinafter referred to as monodisperse degree) of the grains were within ±20% of the average grain size. After this emulsion was desalted and washed with water, it was chemically sensitized in an optimal manner with sodium thiosulfate in the presence of a nucleic acid decomposition product. The thus-obtained emulsion was named emulsion A.

Further, the above procedure was repeated, with the exception that the reaction temperature at which the grains were formed was changed. Thus there was prepared a similar emulsion that was sulfur-sensitized in an optimal manner, the grains of which ranged from cubes whose corners were chamfered a little (the shape of the cubes was changed to a somewhat tetradecahedral shape) to tetradecahedrons that had an average side length of about 0.35 μm. The monodisperse degree was 92%. The emulsion was named emulsion B.

Emulsions A and B were used after adding compounds ①, ②, ③, and ④, described later.

Emulsions for the green-sensitive emulsion layer were prepared as follows:

30 g of lime-treated gelatin was added to 1000 ml of distilled water, and, after the gelatin was dissolved at 40° C., the pH was adjusted to 3.8 with sulfuric acid and 6.5 g of sodium chloride and 0.02 g of N,N'-dimethylethylenethiourea were added, after which the temperature was raised to 60° C. To the resulting solution were added a solution of 62.5 g of silver nitrate in 750 ml of distilled water and a solution of 26.3 g of potassium bromide and 8.6 g of sodium chloride in 500 ml of distilled water, over a period of 40 min with the temperature kept at 60° C. When the obtained emulsion was observed with an electron microscope, it was found that cubic grains having an average side length of about 0.36 μm were formed. Further, a solution of 62.5 g of silver nitrate in 500 ml of distilled water and a solution of 35.0 g of potassium bromide and 4.3 g of sodium chloride in 300 ml of distilled water were added to the emulsion over a period of 20 min at 70° C. When the thus-prepared emulsion was observed with an electron microscope, it was found that cubic grains having an average side length of about 0.45 μm were formed. When the grain size distribution of the emulsion was measured it was found that the emulsion was a monodisperse emulsion whose monodisperse degree was about 89%. After this emulsion was desalted and washed with water, it was chemically sensitized in an optimal manner with sodium thiosulfate in the presence of a nucleic acid decomposition product. The thus-obtained emulsion was named emulsion C.

Further, the above procedure was repeated, with the exception that the reaction temperature at which the grains were formed was changed. Thus there was prepared a similar emulsion that was sulfur-sensitized in an optimal manner, the grains of which ranged from cubes whose corners were chamfered a little (the shape of the cubes was changed to a somewhat tetradecahedral shape) to tetradecahedrons that had an average side length of about 0.30 μm. The monodisperse degree was 93%. The emulsion was named emulsion D.

Emulsions C and D were used after adding compounds ①, ⑤, ⑥, and ⑦, described later.

Emulsions for the blue-sensitive emulsion layer were prepared as follows:

30 g of lime-processed gelatin was added to 700 ml of distilled water, and, after the gelatin was dissolved at 40° C., the pH was adjusted to 4.2 with sulfuric acid and 8.5 g of sodium chloride and 0.03 g of N,N'-dimethylethylenethiourea were added, after which the temperature was raised to 78° C. To the resulting solution were added a solution of 31.25 g of silver nitrate in 750 ml of distilled water and a solution of 20.8 g of potassium bromide and 0.5 g of sodium chloride in 500 ml of distilled water, over a period of 40 min with the temperature kept at 78° C. When the obtained emulsion was observed with an electron microscope, it was found that tetradecahedral grains that were almost cubic and had an average side length of about 0.50 μm were formed. Further, a solution of 93.75 g of silver nitrate in 500 ml of distilled water and a solution of 49.2 g of potassium bromide and 8.1 g of sodium chloride in 300 ml of distilled water were added to the emulsion over a period of 20 min at 72° C. When the thus-prepared emulsion was observed with an electron microscope, it was found that cubic grains having an average side length of about 0.80 μm were formed. The emulsion was a monodisperse emulsion whose monodisperse degree was about 90%. After this emulsion was desalted and washed with water, it was chemically sensitized in an optimal manner with sodium thiosulfate in the presence of a nucleic acid decomposition product. The thus-obtained emulsion was named emulsion E.

Further, the above procedure was repeated, with the exception that the reaction temperature at which the grains were formed was changed. Thus there was prepared a similar emulsion that was sulfur-sensitized in an optimal manner, the grains of which include cubic grains having an average side length of about 0.55 μm, and the monodisperse degree was about 90%. The thus-obtained emulsion was named emulsion F.

Emulsions E and F were used after adding compounds ①, ⑧, and ⑦, described later.

An emulsified dispersion for the red-sensitive emulsion layer was prepared as follows:

15 g of compound ⑨ of the present invention that had an average molecular weight of about 60,000, which is described later, 10 g of compound ㉒, described later, 1.0 g of compound ㉓, 1.5 g of compound ㉔, 1.5 g of compound ㉕, 2 g of compound ㉘, described later, 4 g of compound ㉙, 0.2 g of compound ⑩, and 30 ml of ethyl acetate were mixed and dissolved at 50° C., and the solution was added to a mixture of 12 ml of 10% sodium dodecylbenzenesulfonate and 190 ml of a 10% aqueous gelatin solution, to obtain an emulsified dispersion, using a homogenizer. The resultant emulsified dispersion was named emulsified dispersion (a).

An emulsified dispersion for the green-sensitive emulsion layer was prepared as follows:

10 g of compound ⑨ of the present invention that had an average molecular weight of about 80,000, which is described later, 11.5 g of exemplified compound (5), 1.5 g of compound ⑪, described later, 1.2 g of compound ⑫, 10 g of compound ㉙, described later, 5 g of compound ⑬, 4.4 g of compound ⑭, and 40 ml of ethyl acetate were mixed and dissolved at 50° C., and the solution was added to a mixture of 13 ml of 10% sodium dodecylbenzenesulfonate and 210 ml of 10% aqueous gelatin solution, to obtain an emulsified dispersion, using a homogenizer. The thus-emulsified dispersion was named emulsified dispersion (b).

An emulsified dispersion for the blue-sensitive emulsion layer was prepared as follows:

19 g of compound ⑨ of the present invention that had an average molecular weight of about 50,000, which is described later, 19 g of compound ㉖, described later, 6.0 g of compound ㉚, described later, 4.3 g of compound ㉗, and 27 ml of ethyl acetate were mixed and dissolved at 50° C., and the solution was added to a mixture of 8 ml of 10% sodium dodecylbenzenesulfonate and 180 ml of 10% aqueous gelatin solution, to obtain an emulsified dispersion, using a homogenizer. The thus-emulsified dispersion was named emulsified dispersion (c).

mediate layers, such as a color-mix preventing layer and an ultraviolet-absorbing layer, were provided, thereby preparing a coated sample having the layer constitution and the composition as shown in Table A.

Emulsified dispersions in the ultraviolet-absorbing layer and the color-mix-preventing layer were prepared in the same way as the above emulsified dispersions for the emulsion layers.

In this coated sample, for the purpose of preventing irradiation, to make, for example, the sharpness of the image favorable, compounds ⑮, ⑯, ⑰, and ⑱, described later, were used in amounts of 0.002 to 0.04 g/m².

As a hardening agent for the gelatin, compounds ⑲, and ⑳, described later, were used.

TABLE A

| Layer | Main Component | Amount used |
|---|---|---|
| Seventh Layer (Protective Layer) | Gelatin | 1.30 |
| | Acryl-modified Copolymer of Poly(vinyl alcohol) (modification degree: 17%) | 0.15 |
| | Liquid Paraffin | 0.05 |
| Sixth Layer (UV Absorbing Layer) | Gelatin | 0.65 |
| | UV Absorbent 23 | 0.02 |
| | UV Absorvent 24 | 0.09 |
| | UV Absorvent 31 | 0.10 |
| | Color-Mix Inhibitor 21 | 0.02 |
| | Solvent 28 | 0.10 |
| Fifth Layer (Red-sensitive Layer) | Emulsion A | 0.05 |
| | Emulsion B | 0.19 |
| | Gelatin | 1.76 |
| | Polymer ⑨ | 0.54 |
| | Cyan Coupler 22 | 0.36 |
| | Image-Dye Stabilizer 23 | 0.04 |
| | Image-Dye Stabilizer 24 | 0.05 |
| | Image-Dye Stabilizer 25 | 0.05 |
| | Image-Dye Conditioner 10 | 0.01 |
| | Solvent 28 | 0.07 |
| | Solvent 13 | 0.14 |
| Fourth Layer (UV Absorbing Layer) | Gelatin | 1.60 |
| | UV Absorvent 23 | 0.06 |
| | UV Absorvent 24 | 0.27 |
| | UV Absorvent 31 | 0.29 |
| | Color-Mix Inhibitor 21 | 0.05 |
| | Solvent 28 | 0.24 |
| Third Layer (Green-sensitive Layer) | Emulsion C | 0.08 |
| | Emulsion D | 0.08 |
| | Gelatin | 2.20 |
| | Polymer ⑨ | 0.45 |
| | Magenta Coupler Exemplified Compound (5) | 0.52 |
| | Image-Dye Stabilizer 11 | 0.07 |
| | Image-Dye Stabilizer 12 | 0.05 |
| | Image-Dye Stabilizer 14 | 0.20 |
| | Solvent 29 | 0.45 |
| | Solvent 13 | 0.23 |
| Second Layer (Color Mix Inhibiting Layer) | Gelatin | 0.99 |
| | Color-Mix Inhibitor 21 | 0.09 |
| | Solvent 30 | 0.08 |
| First Layer (Blue-sensitive Layer) | Emulsion E | 0.16 |
| | Emulsion F | 0.11 |
| | Gelatin | 2.68 |
| | Polymer ⑨ | 0.74 |
| | Yellow Coupler 26 | 0.74 |
| | Image-Dye Stabilizer 27 | 0.17 |
| | Solvent 30 | 0.23 |
| Supporting Base | Polyethylene-laminated Paper (TiO₂ and ultramarine dye were included in the polyethylene film of the first layer side) | |

"Amount used" is indicated in g/m².
Emulsion is indicated as g/m² in terms of silver.

Emulsions A to F, and emulsified dispersions (a) to (c) were used to make a red-sensitive emulsion layer, a green-sensitive emulsion layer, and a blue-sensitive emulsion layer; and further, a protective layer and inter- The same procedure was repeated, with the exception that exemplified compound (5) was replaced with compound (6), (11), (14), (20), (23), or (26), in an equimolar amount, thereby preparing respective samples II-B to II-G.

Further, exemplified compound (5) was replaced with comparative compound ① or ②, in an equimolar amount to the comparative samples, thereby preparing comparative samples ① and ②.

Samples II-A to II-G, as well as comparative samples ① and ②, were exposed to white light for 0.1 sec. through an optical wedge and blue, green, and red filters, and they were subjected to the following processing (A), (B), and (C).

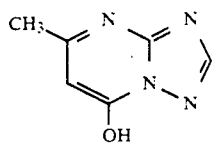

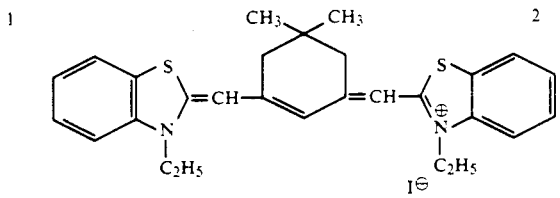

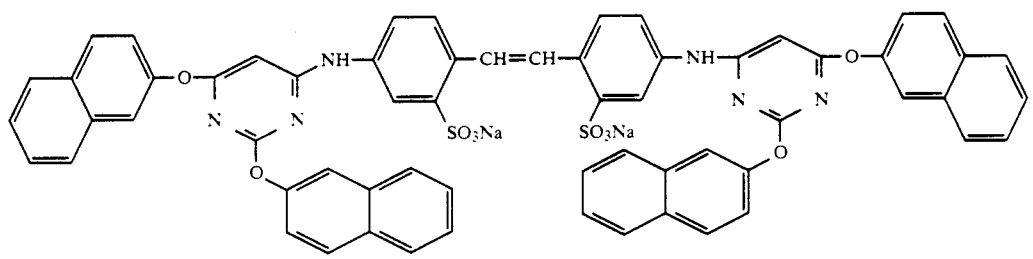

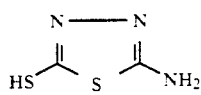

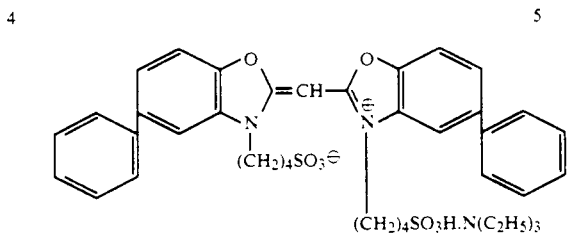

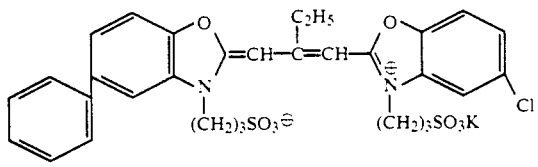

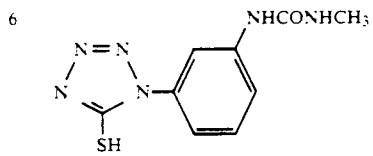

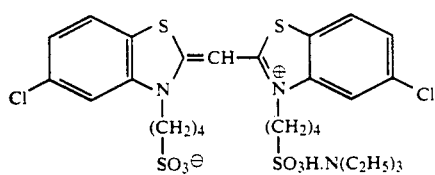

8  Poly(N-tert-butylacrylamide)

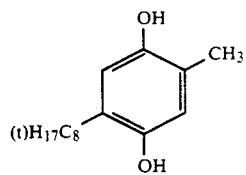

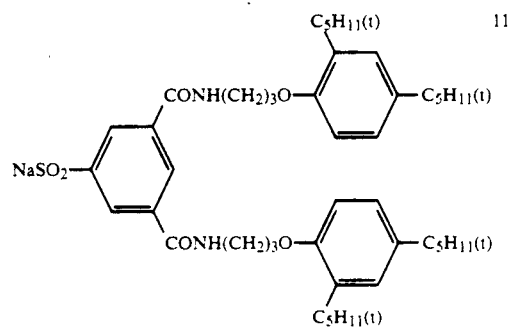

-continued
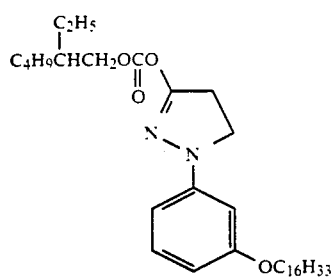
12  Tricresyl phosphate   13
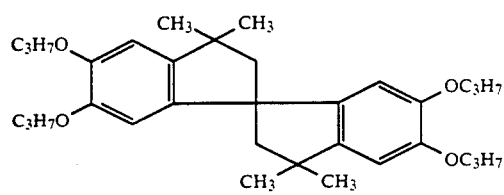  14   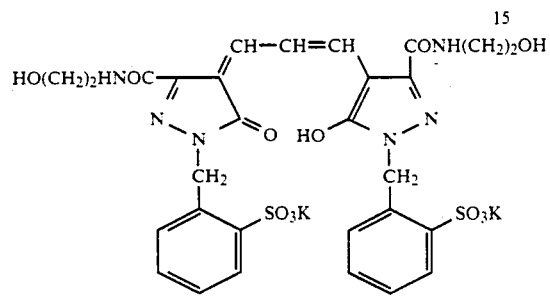   15
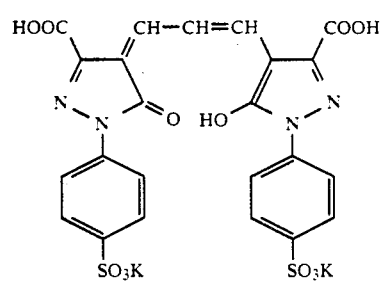  16   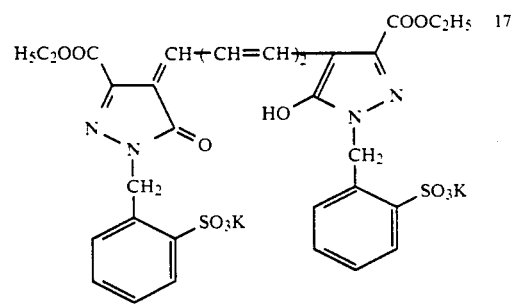   17
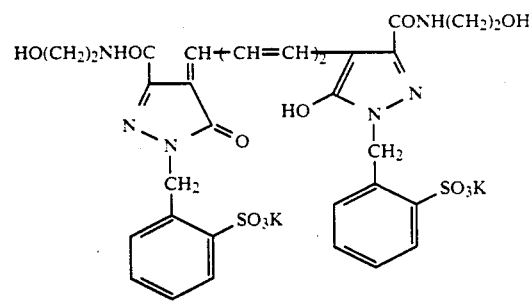  18   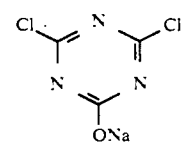   19
3:1 Mixture of   20
CH₂NHCOCH₂SO₂CH=CH₂   (CH₂)₂NHCOCH₂SO₂CH=CH₂
CH₂NHCOCH₂SO₂CH=CH₂ and CH₂NHCOCH₂SO₂CH=CH₂
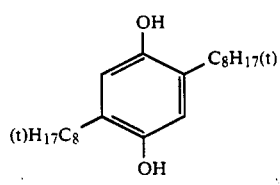   21
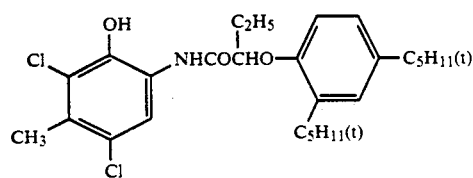   22   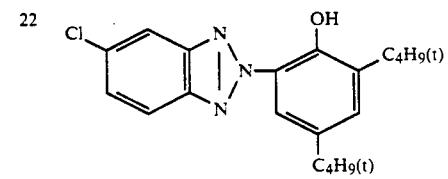   23

-continued

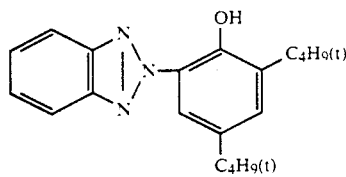 24

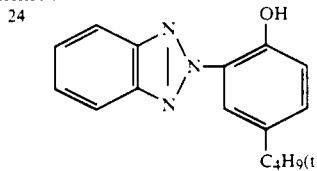 25

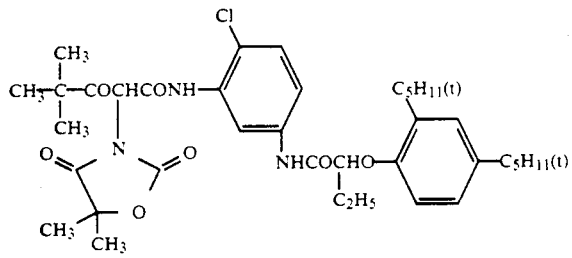 26

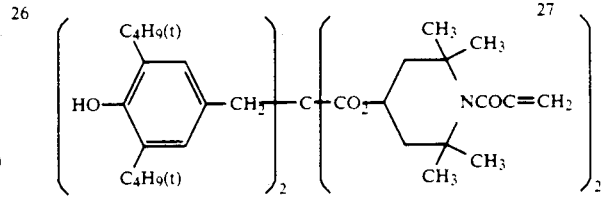 27

Trinonyl phosphate 28   Trioctyl phosphate 29
Dibutyl phthalate 30

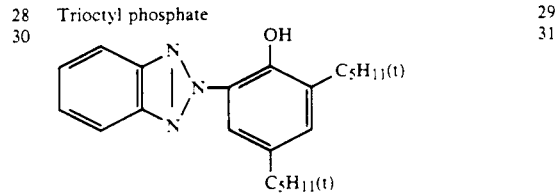 31

| Processing step | Processing (A) Temperature | Time |
|---|---|---|
| Color developing | 33° C. | 3 min 30 sec |
| Bleach-fixing | 33° C. | 1 min 30 sec |
| Washing | 24 to 34° C. | 3 min |
| Drying | 70 to 80° C. | 1 min |

The compositions of the processing solutions were as follows:

| Color-developing solution | |
|---|---|
| Water | 800 ml |
| Diethylenetriaminepentaacetic acid | 1.0 g |
| Nitrilotriacetic acid | 1.5 g |
| Benzyl alcohol | 15.0 ml |
| Diethylene glycol | 10.0 ml |
| Sodium sulfite | 2.0 g |
| Potassium bromide | 0.5 g |
| Potassium carbonate | 30.0 g |
| N-ethyl-N-(β-methanesulfonamidoethyl)-3-methyl-4-aminoaniline sulfate | 5.0 g |
| Hydroxylamine sulfate | 4.0 g |
| Whitening agent (Whitex 4B, manufactured by Sumitomo Chemical Co., Ltd.) | 1.0 g |
| Water to make | 1000 ml |
| pH (25° C.) | 10.20 |

| Bleach-fixing Solution | |
|---|---|
| Water | 400 ml |
| Ammonium thiosulfate (70%) | 150 ml |
| Ethylenediaminetetraacetic acid iron (III) ammonium salt | 55.0 g |
| Ethylenediaminetetraacetic acid disodium salt | 5.0 g |
| Water to make | 1000 ml |
| pH (25° C.) | 6.70 |

| Processing step | Processing (B) Temperature | Time |
|---|---|---|
| Color developing | 38° C. | 1 min 40 sec |
| Bleach-fixing | 30 to 34° C. | 1 min 00 sec |
| Rinsing ① | 30 to 34° C. | 20 sec |
| Rinsing ② | 30 to 34° C. | 20 sec |
| Rinsing ③ | 30 to 34° C. | 20 sec |
| Drying | 70 to 90° C. | 50 sec |

(A counter-current tank system, from the tank of rinsing ③ toward the tank of rinsing ①, was adopted)

The compositions of the processing solutions were as follows:

| Color-developing solution | |
|---|---|
| Water | 800 ml |
| Diethylenetriaminepentaacetic acid | 1.0 g |
| 1-Hydroxyethylidene-1,1-diphosphonic acid (60%) | 2.0 g |
| Nitrilotriacetic acid | 2.0 g |
| Benzyl alcohol | 16.0 ml |
| Diethylene glycol | 10.0 ml |
| Sodium sulfite | 2.0 g |
| Potassium bromide | 0.5 g |
| Potassium carbonate | 30.0 g |
| N-ethyl-N-(β-methanesulfonamidoethyl)-3-methyl-4-aminoaniline sulfate | 5.5 g |
| Hydroxylamine sulfate | 3.0 g |
| Whitening agent (Whitex 4B, manufactured by Sumitomo Chemical Co., Ltd.) | 1.5 g |
| Water to make | 1000 ml |
| pH (25° C.) | 10.25 |

| Bleach-fixing Solution | |
|---|---|
| Water | 400 ml |
| Ammonium thiosulfate (70%) | 200 ml |
| Sodium sulfite | 20.0 g |
| Ethylenediaminetetraacetic acid iron (III) ammonium salt | 60.0 g |
| Ethylenediaminetetraacetic acid disodium | 10.0 g |

| Bleach-fixing Solution | |
|---|---|
| salt | |
| Water to make | 1000 ml |
| pH (25° C.) | 6.70 |

| Rinsing Solution | |
|---|---|
| Benzotriazole | 1.0 g |
| Ethylenediamine-N,N,N',N'-tetramethylene-phosphonic acid | 0.3 g |
| Water to make | 1000 ml |
| pH (25° C.) | 7.50 |

| Processing step | Processing (C) Temperature | Time |
|---|---|---|
| Color developing | 38° C. | 1 min 40 sec |
| Bleach-fixing | 30 to 34° C. | 1 min 00 sec |
| Rinsing ① | 30 to 34° C. | 20 sec |
| Rinsing ② | 30 to 34° C. | 20 sec |
| Rinsing ③ | 30 to 34° C. | 20 sec |
| Drying | 70 to 80° C. | 50 sec |

(A counter-current tank system, from the-tank of rinsing ③ toward the tank of rinsing ① was adopted)

The compositions of the processing solutions were as follows:

| Color-developing solution | |
|---|---|
| Water | 800 ml |
| Diethylenetriaminepentaacetic acid | 1.0 g |
| 1-Hydroxyethylidene-1,1-diphosphonic acid (60%) | 2.0 g |
| Nitrilotriacetic acid | 2.0 g |
| 1,4-diazabicyclo(2,2,2)octane | 7.5 g |
| Potassium bromide | 0.5 g |
| Potassium carbonate | 30.0 g |
| N-ethyl-N-(β-methanesulfonamidoethyl)-3-methyl-4-aminoaniline sulfate | 5.5 g |
| Hydroxylamine sulfate | 4.0 g |
| Whitening agent (UVITEX-CK, manufactured by Ciba-Geigy) | 1.5 g |
| Water to make | 1000 ml |
| pH (25° C.) | 10.25 |

| Bleach-fixing Solution | |
|---|---|
| Water | 400 ml |
| Ammonium thiosulfate (70%) | 200 ml |
| Sodium sulfite | 20.0 g |
| Ethylenediaminetetraacetic acid iron (III) ammonium salt | 60.0 g |
| Ethylenediaminetetraacetic acid disodium salt | 10.0 g |
| Water to make | 1000 ml |
| pH (25° C.) | 7.00 |

Rinsing Solution

Deionized water (calcium and magnesium were up to 3 ppm respectively)

The samples of the present invention obtained through these processing steps gave magenta color images that were sharp and high in saturation. The magenta density of each of these processed samples was measured, and the sensitivity, the gradation ($\gamma$), and the maximum density were determined. The results are given in Table 2.

TABLE 2

| Sample | Processing (A) | | | Processing (B) | | | Processing (C) | | |
|---|---|---|---|---|---|---|---|---|---|
| | Sensi-tivity* | Gra-dation** | Maximum Density | Sensi-tivity* | Gra-dation** | Maximum Density | Sensi-tivity* | Gra-dation** | Maximum Density |
| Comparative sample ① | 100 | 2.93 | 2.25 | 100 | 2.87 | 2.30 | 100 | 2.90 | 2.29 |
| Comparative sample ② | 97 | 2.87 | 2.21 | 96 | 2.86 | 2.25 | 98 | 2.88 | 2.26 |
| II-A | 118 | 3.12 | 2.35 | 117 | 3.10 | 2.38 | 110 | 3.12 | 2.37 |
| II-B | 117 | 3.11 | 2.31 | 116 | 3.08 | 2.37 | 109 | 3.10 | 2.36 |
| II-C | 112 | 3.10 | 2.33 | 116 | 3.11 | 2.38 | 108 | 3.11 | 2.35 |
| II-D | 109 | 3.12 | 2.32 | 114 | 3.09 | 2.39 | 109 | 3.09 | 2.38 |
| II-E | 110 | 3.09 | 2.30 | 112 | 3.08 | 2.38 | 112 | 3.08 | 2.37 |
| II-F | 108 | 3.11 | 2.29 | 116 | 3.07 | 2.37 | 111 | 3.07 | 2.36 |
| II-G | 109 | 3.10 | 2.28 | 115 | 3.09 | 2.36 | 110 | 3.08 | 2.31 |

*The sensitivity shows the relative value of the sensitivity designated by a reciprocal of the amount of light exposure that gives a density of 0.8 with comparative sample ① assumed as 100.
**The gradation ($\gamma$) shows the gradient of the sensitometry from a density of 0.6 to a density of 2.5.

As is apparent from the results of Table 2, the photographic material of the present invention showed superior characteristics in any of sensitivity, gradation, and color density in comparison to one containing a magenta coupler having at the 6-position an alkyl group.

EXAMPLE 3

Each of comparative samples ① and ② of the color photographic material was prepared by multi-coatings composed of the first to the twelfth layers as hereinbelow defined on a double-sided polyethylene-laminated paper base. A white pigment (TiO$_2$) and a small amount of bluish dye (ultramarine blue) were included in the first layer side polyethylene film laminated.

Composition of the Photosensitive Layers

In the following compositions, each ingredient is indicated in g/m$^2$ of a coating amount, but the coating amount of the silver halide is shown in g/m$^2$ in terms of silver.

| First layer: Gelatin layer | 1.30 |
|---|---|
| Gelatin | |
| Second layer: Antihalation layer | |
| Black colloidal silver | 0.10 |
| Gelatin | 0.70 |
| Third layer: Red-sensitive emulsion (low sensitivity) layer | |

| | |
|---|---|
| Silver iodobromide emulsion spectral-sensitized by red-sensitizing dye (*1 and *2) (silver iodide: 5.0 mol %, average grain size: 0.4 μm) | 0.15 |
| Gelatin | 1.00 |
| Cyan coupler (*3) | 0.14 |
| Cyan coupler (*4) | 0.07 |
| Discoloration inhibitor (*5, *6 and *7) | 0.10 |
| Solvent for coupler (*8 and *9) | 0.06 |
| Fourth layer: Red-sensitive emulsion (highly sensitive) layer | |
| Silver iodobromide emulsion spectral-sensitized by red-sensitizing dye (*1 and *2) (silver iodide: 6.0 mol %, average grain size: 0.7 μm) | 0.15 |
| Gelatin | 1.00 |
| Cyan coupler (*3) | 0.20 |
| Cyan coupler (*4) | 0.10 |
| Discoloration inhibitor (*5, *6 and *7) | 0.15 |
| Solvent for coupler (*8 and *9) | 0.10 |
| Fifth layer: Intermediate layer | |
| Magenta colloidal silver | 0.02 |
| Gelatin | 1.00 |
| Color-mix inhibitor (*10) | 0.08 |
| Solvent for color-mix inhibitor (*11 and *12) | 0.16 |
| Polymer latex (*13) | 0.10 |
| Sixth layer: Green-sensitive emulsion (low sensitivity) layer | |
| Silver iodobromide emulsion spectral-sensitized by green-sensitizing dye (*14) (silver iodide: 2.5 mol %, average grain size: 0.4 μm) | 0.10 |
| Gelatin | 0.80 |
| Magenta coupler (*15) | 0.10 |
| Discoloration inhibitor (*16) | 0.10 |
| Stain inhibitor (*17) | 0.01 |
| Stain inhibitor (*18) | 0.001 |
| Solvent for coupler (*11 and *19) | 0.15 |
| Seventh layer: Green-sensitive emulsion (highly sensitive) layer | |
| Silver iodobromide emulsion spectral-sensitized by green-sensitizing dye (*14) (silver iodide: 3.5 mol %, average grain size: 0.9 μm) | 0.10 |
| Gelatin | 0.80 |
| Magenta coupler (*15) | 0.10 |
| Discoloration inhibitor (*16) | 0.10 |
| Stain inhibitor (*17) | 0.01 |
| Stain inhibitor (*18) | 0.001 |
| Solvent for coupler (*11 and *19) | 0.15 |
| Eighth layer: Yellow filter layer | |
| Yellow colloidal silver | 0.20 |
| Gelatin | 1.00 |
| Color-mix inhibitor (*10) | 0.06 |
| Solvent for color-mix inhibitor (*11 and *12) | 0.15 |
| Polymer latex (*13) | 0.10 |
| Ninth layer: Blue-sensitive emulsion (low sensitivity) layer | |
| Silver iodobromide emulsion spectral-sensitized by blue-sensitizing dye (*20) (silver iodide: 2.5 mol %, average grain size: 0.5 μm) | 0.15 |
| Yellow coupler (*21) | 0.20 |
| Stain inhibitor (*18) | 0.001 |
| Solvent for coupler (*9) | 0.05 |
| Tenth layer: Blue-sensitive emulsion (highly sensitive) layer | |
| Silver iodobromide emulsion spectral-sensitized by blue-sensitizing dye (*20) (silver iodide: 2.5 mol %, average grain size: 1.2 μm) | 0.25 |
| Gelatin | 1.00 |
| Yellow coupler (*21) | 0.40 |
| Stain inhibitor (*18) | 0.002 |
| Solvent for coupler (*9) | 0.10 |
| Eleventh layer: UV-absorbing layer | |
| Gelatin | 1.50 |
| UV absorbent (*22, *6 and *7) | 1.00 |
| Color-mix inhibitor (*23) | 0.06 |
| Solvent for color-mix inhibitor (*9) | 0.15 |
| Irradiation-preventing dye (*24) | 0.02 |
| Irradiation-preventing dye (*25) | 0.02 |
| Twelfth layer: Protective layer | |
| Fine grain size silver chlorobromide emulsion (silver chloride: 97 mol %, average grain size: 0.2 μm) | 0.07 |
| Gelatin | 1.50 |
| Gelatin hardener (*26) | 0.17 |

In this example the following compounds were used:

*1: 5,5'-dichloro-3,3'-di(3-sulfobutyl)-9-ethylthiacarbonylcyanine sodium salt

*2: Triethylammonium-3-[2-{2-[3-(3-sulfopropyl)naphtho-(1,2-d)thiazoline-2-indenemethyl]-1-butenyl}-3-naphtho(1,2-d)thiazolyno]propane sulfonate

*3: 2-[α-(2,4-Di-t-amylphenoxy)hexaneamido]-4,6-dichloro-5-ethylphenol

*4: 2-(2-Chlorobenzoylamido)-4-chloro-5-[α-(2-chloro-4-t-amylphenoxy)octaneamido]-phenol

*5: 2-(2-Hydroxy-3-sec-5-t-butylphenyl)benzotriazole

*6: 2-(2-Hydroxy-5-t-butylphenyl)benzotriazole

*7: 2-(2-Hydroxy-3,5-di-t-butylphenyl)-6-chlorobenzotriazole

*8: Dioctyl phthalate

*9: Trinonyl phosphate

*10: 2,5-Di-t-octylhydroquinone

*11: Tricresyl phosphate

*12: Dibutyl phthalate

*13: Poly(ethyl acrylate)

*14: 5,5'-diphenyl-9-ethyl-3,3'-disulfopropyloxycarbocyanin sodium salt

*15: Coupler ① or ② for comparison (comparative compound ① or ②)

*16: 3,3,3',3'-Tetramethyl-5,6,5',6'-tetraproxy-1,1'-bis-spiroindan

*17: 3-(2-Ethylhexyloxycarbonyloxy)-1-(3-hexadecyloxyphenyl)-2-pyrazolin

*18: 2-Methyl-5-t-octylhydroquinone

*19: Trioctyl phosphate

*20: Triethylammonium-3-[2-(3-benzylrohdanin-5-yliden)-3-benzoxazolynyl]propane sulphonate

*21: α-Pivaloyl-α-[(2,4-dioxo-1-benzyl-5-ethoxyhydantoin-3-yl)-2-chloro-5-(α-2,4-di-t-amylphenoxy)-butanamido]acetoanilido

*22: 5-Chloro-2-(hydroxy-3-t-butyl-5-t-octyl)phenylbenztriazole

*23: 2,5-Di-sec-octylhydroquinone

*24: 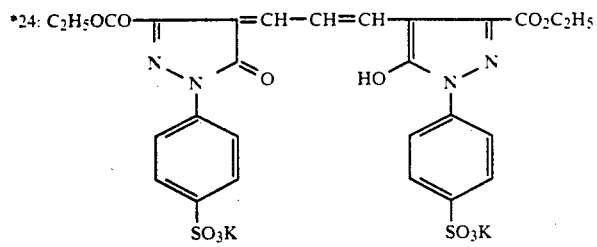

*25: 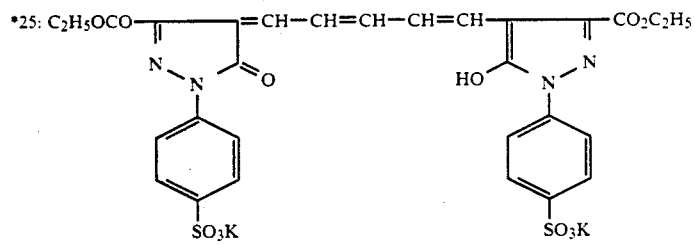

*26: 1,4-Bis(vinylsulfonylacetoanilido)ethane

Next, Samples III-A to III-M were prepared by repeating the preparation procedure of comparative sample ① or ②, except that magenta coupler for comparison (*15) was changed to an equal mol of exemplified compound (5), (6), (7), (8), (10), (12), (14), (19), (20), (21), (23), (24), or (26), respectively. Then, comparative samples ① and ② and Samples III-A to III-M were subjected to the usual exposure through an optical wedge and then to a color development process according to the following procedure and solution compositions.

The thus-processed samples were evaluated with respect to sensitometry. The results are shown in Table 3.

| Processing Procedure | | |
|---|---|---|
| Step | Temperature | Time |
| First developing (Black and white developing) | 38° C. | 75 sec. |
| Water-washing | 38° C. | 90 sec. |
| Reversal exposure | over 100 Lux | over 60 sec. |
| Color developing | 38° C. | 135 sec. |
| Water washing | 38° C. | 45 sec. |
| Bleach-fixing | 38° C. | 120 sec. |
| Water washing | 38° C. | 135 sec. |
| Drying | | |

| Compositions of processing solutions First Developing Solution | |
|---|---|
| Pentasodium nitrilo-N,N,N-trimethylene-phosphonate | 0.6 g |
| Pentasodium diethylenetriaminepentaacetate | 4.0 g |
| Potassium sulfite | 30.0 g |
| Potassium thiocyanate | 1.2 g |
| Potassium carbonate | 35.0 g |
| Potassium hydroquinonemonosulfonate | 25.0 g |
| Diethyleneglycol | 15.0 ml |
| 1-Phenyl-4-hydroxymethyl-4-methyl-3-pyrazolidone | 2.0 g |
| Potassium bromide | 0.5 g |
| Potassium iodide | 5.0 mg |
| Water to make | 1000 ml |
| | (pH 9.70) |

| Color-Developing Solution | |
|---|---|
| Benzyl alcohol | 15.0 ml |
| Diethylene glycol | 12.0 ml |
| 3,6-Dithia-1,8-octanediol | 0.2 g |
| Pentasodium nitrilo-N,N,N-trimethylene-phosphonate | 0.5 g |
| Pentasodium diethylenetriaminepentaacetate | 2.0 g |
| Sodium sulfite | 2.0 g |
| Sodium carbonate | 25.0 g |
| Hydroxylamine sulfonate | 3.0 g |
| N-Ethyl-N-($\beta$-methanesulfonamidoethyl)-3-methyl-4-aminoaniline sulfonate | 5.0 g |
| Potassium bromide | 0.5 g |
| Potassium iodide | 1.0 mg |
| Water to make | 1000 ml |
| | (pH 10.40) |

| Bleach-fixing Solution | |
|---|---|
| 2-Mercapto-1,3,4-triazole | 1.0 g |
| Disodium ethylenediaminetetraacetate dihydrate | 5.0 g |
| Ammonium iron (III) ethylenediamine-tetraacetate monohydrate | 80.0 g |
| Sodium sulfite | 15.0 g |
| Sodium thiosulfate (700 g/l solution) | 160.0 ml |
| Glacial acetic acid | 5.0 ml |
| Water to make | 1000 ml |
| | (pH 6.50) |

TABLE 3

| Sample | Coupler | Gradation* ($\gamma$) | Max. Density** (Dm) |
|---|---|---|---|
| Comparative Sample ① | Comparative Compound ① | 2.27 | 2.50 |
| Comparative Sample ② | Comparative Compound ② | 2.26 | 2.48 |
| III-A | Exemplified Compound (5) | 2.60 | 2.65 |
| III-B | Exemplified Compound (6) | 2.54 | 2.63 |
| III-C | Exemplified Compound (7) | 2.55 | 2.61 |
| III-D | Exemplified Compound (8) | 2.49 | 2.60 |
| III-E | Exemplified Compound (10) | 2.44 | 2.60 |
| III-F | Exemplified Compound (12) | 2.46 | 2.59 |

TABLE 3-continued

| Sample | Coupler | Gradation* (γ) | Max. Density** (Dm) |
|---|---|---|---|
| III-G | Exemplified Compound (14) | 2.51 | 2.61 |
| III-H | Exemplified Compound (19) | 2.50 | 2.58 |
| III-I | Exemplified Compound (20) | 2.48 | 2.60 |
| III-J | Exemplified Compound (21) | 2.45 | 2.54 |
| III-K | Exemplified Compound (23) | 2.40 | 2.53 |
| III-L | Exemplified Compound (24) | 2.49 | 2.60 |
| III-M | Exemplified Compound (26) | 2.44 | 2.55 |

*The gradation (γ) shows the gradient of the sensitometry from a density of 0.6 to a density of 2.5.
**The max. density shows the magenta density.

As is apparent from the results in Table 3, the gradation (γ) of each of Samples III-A to III-M are improved. Each of these Samples, III-A to III-M, showed high color density.

EXAMPLE 4

Comparative samples ① and ② as color photographic materials were prepared by multi-layer coatings composed of the first to the twelfth layers on a triacetate cellulose film base.

First Layer: Antihalation Layer

The ultraviolet absorbent, consisting of 15 g of 5-chloro-2-(2-hydroxy-3,5-di-t-butylphenyl)-2H-benzotriazole, 30 g of 2-(2-hydroxy-5-t-butylphenyl)-2H-benzotriazole, and 35 g of 2-(2-hydroxy-3-secbutyl-5-t-butylphenyl)-2H-benzotriazole; 100 g of dodecyl-5-(N,N-diethylamino)-2-benzenesulfonyl-2,4-pentadienoate; 200 ml of tricresyl phosphate; 200 ml of ethyl acetate; 20 g of sodium dodecylbenzenesulfonate; and a 10% aqueous solution of gelatin were mixed and emulsified by high-speed agitation. The thus-prepared emulsion (hereinafter referred to as Emulsion (a)) was mixed with a 10% aqueous solution of gelatin, black colloidal silver, water, and coating aids. The resulting mixture was coated so as to form a 2 μm layer (as a dry thickness).

Second Layer: Intermediate Layer of Gelatin

A solution of 50 g of 2,5-di-t-octylhydroquinone in a mixture of 100 ml of dibutyl phthalate and 100 ml of ethyl acetate was emulsified with 1 kg of a 10% aqueous solution of gelatin by high-speed agitation. 2 kg of the thus-obtained emulsion (hereinafter referred to as Emulsion (b)) was mixed with 1.5 kg of a 10% aqueous solution of gelatin, and the resulting mixture was coated so as to form a 1 μm layer (as a dry thickness).

Third Layer: Red-Sensitive Emulsion (Low Sensitivity) Layer

A solution of 100 g of cyan coupler, 2-(heptafluorobutylamido)-5-{2'-(2'',4''-di-t-aminophenoxy)-butyramido-phenol, in a mixture of 100 ml of tricresyl phosphate and 100 ml of ethyl acetate was emulsified with 1 kg of a 10% aqueous solution of gelatin by high-speed agitation. 500 g of the thus-obtained emulsion (hereinafter referred to as Emulsion (c)) was mixed with 1 kg of red-sensitive silver iodobromide emulsion (content of silver: 70 g, gelatin: 60 g, and iodine: 4 mol %), and the resulting mixture was coated so as to form a 1 μm (as a dry thickness) layer. (coating amount in terms of silver: 0.5 g/m²)

Fourth Layer: Red-Sensitive Emulsion (Highly Sensitive) Layer 500 g of Emulsion (c) was mixed with 1 kg of red-sensitive silver iodobromide emulsion (content of silver: 70 g, gelatin: 60 g, and iodine: 2.5 mol %), and the resulting mixture was coated so as to form a 2.5 μm layer (as a dry thickness). (coating amount of silver: 0.8 g/m²)

Fifth Layer: Intermediate Layer

A mixture of 1 kg of Emulsion (b) and 1 kg of a 10% aqueous solution of gelatin was coated so as to form a 1 μm layer (as a dry thickness).

Sixth Layer: Green-Sensitive Emulsion (Low Sensitivity) Layer

The preparation procedure of Emulsion (c) of the third layer was repeated, except that the cyan coupler was changed to comparative compound ① and comparative compound ②. 300 g of the thus-prepared emulsion (hereinafter referred to as Emulsion (d)) was mixed with 1 kg of green-sensitive silver iodobromide emulsion (content of silver: 70 g, gelatin: 60 g, and iodine: 3 mol %), and the resulting mixture was coated so as to form a 2.0 μm layer (as a dry thickness). (coating amount of silver: 0.7 g/m²)

Seventh Layer: Green-Sensitive Emulsion (Highly Sensitive) Layer

A mixture of 1 kg of Emulsion (d) and 1 kg of green-sensitive silver iodobromide emulsion (content of silver: 70 g, gelatin: 60 g, and iodine: 2.5 mol %) was coated so as to form a 2.0 μm layer (as a dry thickness). (coating amount of silver: 0.7 g/m²)

Eighth Layer: Intermediate Layer of Gelatin

A mixture of 1 kg of Emulsion (b) and 1 kg of a 10% aqueous solution of gelatin was coated so as to form a 0.5 μm layer (as a dry thickness).

Ninth Layer: Yellow Filter Layer

An emulsion containing yellow colloidal silver was coated so as to form a 1 μm layer (as a dry thickness).

Tenth Layer: Blue-Sensitive Emulsion (Low Sensitivity) Layer

The preparation procedure of Emulsion (c) of the third layer was repeated, except that the cyan coupler was changed to yellow coupler α-(pivaloyl)-α-(1-benzyl-5-ethoxy-3-hidantoinyl)-2-chloro-5-dodecyloxycarbonylacetanilide. 1 kg of the thus-prepared emulsion (hereinafter referred to as Emulsion (e)) was mixed with 1 kg of blue-sensitive silver iodobromide emulsion (content of silver: 70 g, gelatin: 60 g, and iodine: 2.5 mol %), and the resulting mixture was coated so as to form a 1.5 μm layer (as a dry thickness). (coating amount of silver: 0.6 g/m²)

Eleventh Layer: Blue-Sensitive Emulsion (Highly Sensitive) Layer

A mixture of 1 kg of Emulsion (e) and 1 kg of blue-sensitive silver iodobromide emulsion (content of silver: 70 g, gelatin: 60 g, and iodine: 2.5 mol %) was coated so as to form a 3 μm layer (as a dry thickness). (coating amount of silver: 1.1 g/m²)

Twelfth Layer: Second Protective Layer

Emulsion (a) was mixed with a 10% aqueous solution of gelatin, water and a coating aid, and the resulting mixture was coated so as to form a 2 μm layer (as a dry thickness).

Thirteenth Layer: First Protective Layer

A 10% aqueous solution of gelatin containing a surface-fogged fine grain emulsion (average grain size: 0.06 μm, 1 mol % silver iodobromide emulsion) was coated so as to form a layer having a coating amount of 0.1 g/m² of silver and 0.8 μm in dry thickness.

To each layer the gelatin hardener 1,4-bis(vinylsulfonylacetoamido)ethane and a surface-active agent were added.

Then, Samples IV-A to IV-O were prepared by repeating the preparation procedure of comparative sample (1) or (2), except that the comparative compound was changed to exemplified compound (5), (6), (7), (8), (9), (10), (11), (19), (20), (21), (22), (23), (24), (25) or (26), respectively.

Then, comparative samples (1) and (2) and Samples IV-A to IV-O were subjected to an exposure through an optical wedge for neutral-grey sensitometry and then to a reversal processing hereinbelow described.

| Processing Procedure | | |
|---|---|---|
| Step | Time | Temperature |
| First developing | 6 min. | 38° C. |
| Water washing | 2 min. | " |
| Reversal | 2 min. | " |
| Color developing | 6 min. | " |
| Conditioning | 2 min. | " |
| Bleaching | 6 min. | " |
| Fixing | 4 min. | " |
| Water washing | 4 min. | " |
| Stabilizing | 1 min. | Normal temperature |
| Drying | | |

The compositions of the processing solutions are as follows:

| First developing solution | |
|---|---|
| Water | 700 ml |
| Pentasodium nitrilo-N,N,N-trimethylene phosphonate | 2 g |
| Sodium sulfite | 20 g |
| Hydroquinone monosulfonate | 30 g |
| Sodium carbonate (monohydrate) | 30 g |
| 1-Phenyl-4-methyl-4-hydroxymethyl-3-pyrazolidone | 2 g |
| Potassium bromide | 2.5 g |
| Potassium thiocyanate | 1.2 g |
| Potassium iodide (0.1% solution) | 2 ml |
| Water to make | 1000 ml |

| Reversal solution | |
|---|---|
| Water | 700 ml |
| Pentasodium nitrilo-N,N,N-trimethylene phosphonate | 3 g |
| Stannous chloride (dihydrate) | 1 g |
| p-Aminophenol | 0.1 g |
| Sodium hydroxide | 8 g |
| Glacial acetic acid | 15 ml |
| Water to make | 1000 ml |

| Color-developing solution | |
|---|---|
| Water | 700 ml |
| Pentasodium nitrilo-N,N,N-trimethylene phosphonate | 3 g |
| Sodium sulfite | 7 g |
| Sodium phosphate (dodecahydrate) | 36 g |
| Potassium bromide | 1 g |
| Potassium iodide (0.1% solution) | 90 ml |
| Sodium hydroxide | 3 g |
| Citrazic acid | 1.5 g |
| N-Ethyl-N-(β-methanesulfonamidoethyl)-3-methyl-4-aminoaniline sulfonate | 11 g |
| 3,6-Ditioctane-1,8-diol | 1 g |
| Water to make | 1000 ml |

| Conditioning solution | |
|---|---|
| Water | 700 ml |
| Sodium sulfite | 12 g |
| Sodium ethylenediaminetetraacetate dihydrate | 8 g |
| Thioglycerine | 0.4 ml |
| Glacial acetic acid | 3 ml |
| Water to make | 1000 ml |

| Bleaching solution | |
|---|---|
| Water | 800 ml |
| Sodium ethylenediaminetetraacetate dihydrate | 2 g |
| Ammonium iron (III) ethylenediaminetetraacetate dihydrate | 120 g |
| Potassium bromide | 100 g |
| Water to make | 1000 ml |

| Fixing solution | |
|---|---|
| Water | 800 ml |
| Sodium thiosulfate | 80.0 g |
| Sodium sulfite | 5.0 g |
| Sodium bisulfite | 5.0 g |
| Water to make | 1000 ml |

| Stabilizing solution | |
|---|---|
| Water | 800 ml |
| Formalin (37 wt. %) | 5.0 ml |
| Fuji Driwel (surface-active agent, made by Fuji Photo Film Co., Ltd.) | 5.0 ml |
| Water to make | 1000 ml |

TABLE 4

| Sample | Coupler | Gradation* ($\gamma$) | Max. Density** (Dm) |
|---|---|---|---|
| Comparative Sample (1) | Comparative Compound (1) | 2.34 | 2.60 |
| Comparative Sample (2) | Comparative Compound (2) | 2.32 | 2.58 |

TABLE 4-continued

| Sample | Coupler | Gradation* ($\gamma$) | Max. Density** (Dm) |
|---|---|---|---|
| IV-A | Exemplified Compound (5) | 2.53 | 2.78 |
| IV-B | Exemplified Compound (6) | 2.51 | 2.76 |
| IV-C | Exemplified Compound (7) | 2.58 | 2.71 |
| IV-D | Exemplified Compound (8) | 2.53 | 2.70 |
| IV-E | Exemplified Compound (9) | 2.48 | 2.65 |
| IV-F | Exemplified Compound (10) | 2.44 | 2.67 |
| IV-G | Exemplified Compound (11) | 2.45 | 2.64 |
| IV-H | Exemplified Compound (19) | 2.43 | 2.66 |
| IV-I | Exemplified Compound (20) | 2.50 | 2.60 |
| IV-J | Exemplified Compound (21) | 2.51 | 2.62 |
| IV-K | Exemplified Compound (22) | 2.48 | 2.63 |
| IV-L | Exemplified Compound (23) | 2.49 | 2.64 |
| IV-M | Exemplified Compound (24) | 2.44 | 2.70 |
| IV-N | Exemplified Compound (25) | 2.45 | 2.65 |
| IV-O | Exemplified Compound (26) | 2.44 | 2.60 |

*The gradation ($\gamma$) shows the gradient of the sensitometry from a density of 0.6 to a density of 2.0.
**Max. density shows the magenta density.

As is apparent from the results in Table 4, Samples IV-A to IV-O of this invention are improved in gradations, and these Samples afford high densities.

EXAMPLE 5

Each of comparative samples ① and ② as a multi-layered color photographic material was prepared by multi-coatings having the following compositions on an under-coated triacetate cellulose film base.

Compositions of the Photosensitive Layers

In the following compositions, the coating amount of silver halide and colloidal silver are indicated by $g/m^2$ in terms of silver, the coating amount of the coupler, additive, and gelatin are each indicated by $g/m^2$, and the coating amount of the sensitizing dye is indicated by mol per mol of silver halide in the same layer.

| First layer: Antihalation layer | |
|---|---|
| Black colloidal silver | 0.2 |
| Gelatin | 1.3 |
| ExM-9 | 0.06 |
| UV-1 | 0.03 |
| UV-2 | 0.06 |
| UV-3 | 0.06 |
| Solv-1 | 0.15 |
| Solv-2 | 0.15 |
| Solv-3 | 0.05 |

| Second layer: Intermediate layer | |
|---|---|
| Gelatin | 1.0 |
| UV-1 | 0.03 |
| ExC-4 | 0.02 |
| ExF-1 | 0.004 |
| Solv-1 | 0.1 |
| Solv-2 | 0.1 |

| Third layer: Red-sensitive emulsion (low sensitivity) layer | | |
|---|---|---|
| Silver iodobromide emulsion (AgI: 4 mol %, uniform AgI-type, equivalent circle-diameter: 0.5 µm, deviation coefficient: 20%, tabular, ratio of diameter/thickness: 3.0) | silver | 0.6 |
| Gelatin | | 1.0 |
| ExS-1 | | $4 \times 10^{-4}$ |
| ExS-2 | | $5 \times 10^{-5}$ |
| ExC-1 | | 0.05 |
| ExC-2 | | 0.50 |
| ExC-3 | | 0.03 |
| ExC-4 | | 0.12 |
| ExC-5 | | 0.01 |

| Fourth layer: Red-sensitive emulsion (highly sensitive) layer | | |
|---|---|---|
| Silver iodobromide emulsion (AgI: 6 mol %, inside-higher AgI-type of core/shell ratio 1:1, equivalent circle-diameter: 0.7 µm, deviation coefficient: 15%, tabular, ratio of diameter/thickness: 5.0) | silver | 0.7 |
| Gelatin | | 1.0 |
| ExS-1 | | $3 \times 10^{-4}$ |
| ExS-2 | | $2.3 \times 10^{-5}$ |
| ExC-6 | | 0.11 |
| ExC-7 | | 0.05 |
| ExC-4 | | 0.05 |
| Solv-1 | | 0.05 |
| Solv-3 | | 0.05 |

| Fifth layer: intermediate layer | |
|---|---|
| Gelatin | 0.5 |
| Cpd-1 | 0.1 |
| Solv-1 | 0.05 |

| Sixth layer: Green-sensitive emulsion (low sensitivity) layer | | |
|---|---|---|
| Silver iodobromide emulsion (AgI: 4 mol %, surface-higher AgI-type of core/shell ratio 1:1, equivalent circle-diameter: 0.5 µm, deviation coefficient: 15%, tabular, ratio of diameter/thickness: 4.0) | silver | 0.35 |
| Silver iodobromide emulsion (AgI: 3 mol %, uniform AgI-type, equivalent circle-diameter: 0.3 µm, deviation coefficient: 15%, circular, ratio of diameter/thickness: 1.0) | silver | 0.20 |
| Gelatin | | 1.0 |
| ExS-3 | | $5 \times 10^{-4}$ |
| ExS-4 | | $3 \times 10^{-4}$ |
| ExS-5 | | $1 \times 10^{-4}$ |
| Comparative compound ① or ② | | 0.28 |
| ExY-11 | | 0.03 |
| Solv-1 | | 0.3 |
| Solv-4 | | 0.05 |

| Seventh layer: Green-sensitive emulsion (highly sensitive) layer | | |
|---|---|---|
| Silver iodobromide emulsion (AgI: 4 mol %, inside-higher AgI-type of core/shell ratio 1:3, equivalent circle-diameter: 0.7 µm, deviation coefficient: 20%, tabular, ratio of diameter/thickness: 5.0) | silver | 0.8 |

Seventh layer: Green-sensitive emulsion (highly sensitive) layer

| | |
|---|---|
| Gelatin | 0.5 |
| ExS-3 | $5 \times 10^{-4}$ |
| ExS-4 | $3 \times 10^{-4}$ |
| ExS-5 | $1 \times 10^{-4}$ |
| ExM-8 | 0.1 |
| Comparative compound ① or ② | 0.07 |
| ExY-11 | 0.03 |
| ExC-2 | 0.03 |
| Solv-1 | 0.1 |
| Solv-4 | 0.01 |

Eighth layer: Intermediate layer

| | |
|---|---|
| Gelatin | 0.5 |
| Cpd-1 | 0.05 |
| Solv-1 | 0.02 |

Ninth layer: Donor layer for double layers effect to red-sensitive emulsion layer

| | | |
|---|---|---|
| Silver iodobromide emulsion (AgI: 2 mol %, inside-higher AgI-type of core/shell ratio 2:1, equivalent circle diameter: 1.0 μm, deviation coefficient: 15%, tabular, ratio of diameter/thickness: 6.0) | silver | 0.35 |
| Silver iodobromide emulsion (AgI: 2 mol %, inside-higher AgI-type of core/shell ratio 1:1, equivalent circle diameter: 0.4 μm, deviation coefficient: 20%, tabular, ratio of diameter/thickness: 6.0) | silver | 0.20 |
| Gelatin | | 0.5 |
| ExS-3 | | $8 \times 10^{-4}$ |
| ExY-13 | | 0.11 |
| ExM-12 | | 0.03 |
| ExM-14 | | 0.10 |
| Solv-1 | | 0.20 |

Tenth layer: Yellow filter layer

| | |
|---|---|
| Yellow colloidal silver | 0.05 |
| Gelatin | 0.5 |
| Cpd-2 | 0.13 |
| Solv-1 | 0.13 |
| Cpd-1 | 0.10 |

Eleventh layer: Blue-sensitive emulsion (low sensitivity) layer

| | | |
|---|---|---|
| Silver iodobromide emulsion (AgI: 4.5 mol %, uniform AgI-type, equivalent circle-diameter: 0.7 μm, deviation coefficient: 15%, tabular, ratio of diameter/thickness: 7.0) | silver | 0.3 |
| Silver iodobromide emulsion (AgI: 3 mol %, uniform AgI-type, equivalent circle diameter: 0.3 μm, deviation coefficient: 25%, tabular, ratio of diameter/thickness: 7.0) | silver | 0.15 |
| Gelatin | | 1.6 |
| ExS-6 | | $2 \times 10^{-4}$ |
| ExC-16 | | 0.05 |
| ExC-2 | | 0.10 |
| ExC-3 | | 0.02 |
| ExY-13 | | 0.07 |
| ExY-15 | | 1.0 |
| Solv-1 | | 0.20 |

Twelfth layer: Blue-sensitive emulsion (highly sensitive) layer

| | | |
|---|---|---|
| Silver iodobromide emulsion (AgI: 10 mol %, inside-higher AgI-type, equivalent circle diameter: 1.0 μm, deviation coefficient: 25%, polyphase twin tabular, ratio of diameter/thickness: 2.0) | silver | 0.5 |
| Gelatin | | 0.5 |
| ExS-6 | | $1 \times 10^{-4}$ |
| ExY-15 | | 0.20 |
| ExY-13 | | 0.01 |
| Solv-1 | | 0.10 |

Thirteenth layer: First protective layer

| | |
|---|---|
| Gelatin | 0.8 |
| UV-4 | 0.1 |
| UV-5 | 0.15 |
| Solv-1 | 0.01 |
| Solv-2 | 0.01 |

Fourteenth layer: Second protective layer

| | |
|---|---|
| Fine particle silver iodobromide emulsion (AgI: 2 mol %, uniform AgI-type, equivalent circle-diameter: 0.07 μm) | 0.5 |
| Gelatin | 0.45 |
| Poly(methyl methacrylate) particle (diameter: 1.5 μm) | 0.2 |
| H-1 | 0.4 |
| Cpd-5 | 0.5 |
| Cpd-6 | 0.5 |

To each layer, the emulsion stabilizer Cpd-3 (0.04 g/m²) and the surface-active agent Cpd-4 (0.02 g/m²) were added as coating aids.

Next, Samples V-A to V-O were prepared in the same manner as comparative sample ① or ②, except that comparative compound ① or ② was changed to an equal mol exemplified compound (5), (6), (7), (8), (9), (10), (11), (19), (20), (21), (22), (23), (24), (25) or (26), respectively. Then, samples ① and ② and Samples V-A to V-O were subjected to the usual exposure through an optical wedge and then to a color development processing according to the following procedure and processing solutions.

Processing procedure

| Step | Time | Temperature (°C.) |
|---|---|---|
| Color developing | 3 min. 15 sec. | 38 |
| Bleaching | 6 min. 30 sec. | 38 |
| Water washing | 2 min. 10 sec. | 24 |
| Fixing | 4 min. 20 sec. | 38 |
| Water washing (1) | 1 min. 05 sec. | 24 |
| Water washing (2) | 1 min. 00 sec. | 24 |
| Stabilizing | 1 min. 05 sec. | 38 |
| Drying | 4 min. 20 sec. | 55 |

UV-1

UV-2

-continued
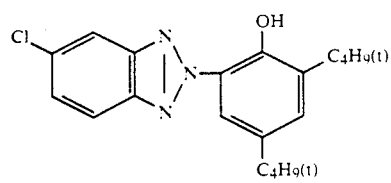
UV-3
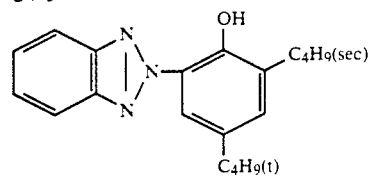
UV-5
$(C_2H_5)_2N-CH=CH-CH=C(COOC_8H_{17})(SO_2C_6H_5)$
Solv-2
Dibutyl phthalate
Solv-4
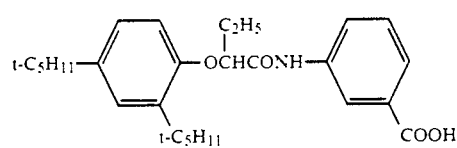
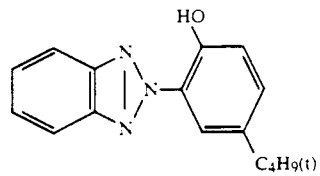
UV-4
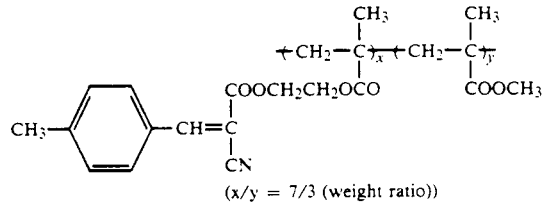
(x/y = 7/3 (weight ratio))
Solv-1
Tricresyl phosphate
Solv-3
Dioctyl phthalate
Cpd-1
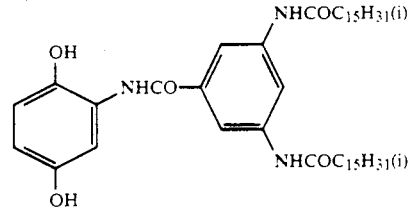
Cpd-2
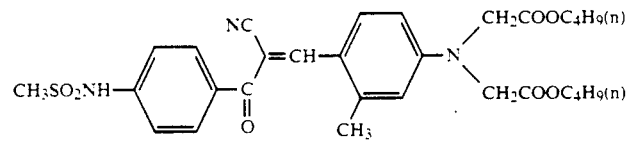
Cpd-3
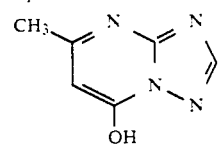
Cpd-5
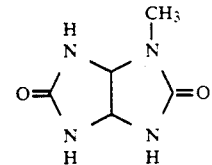
ExC-1
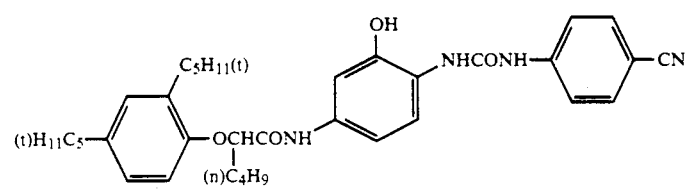
ExC-2
Cpd-4
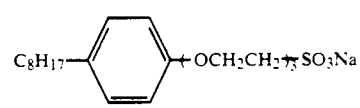
$C_8H_{17}$—⌬—$(OCH_2CH_2)_3SO_3Na$
Cpd-6
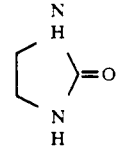
ExC-3

-continued
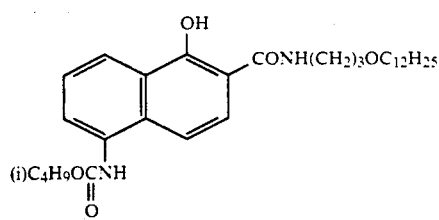
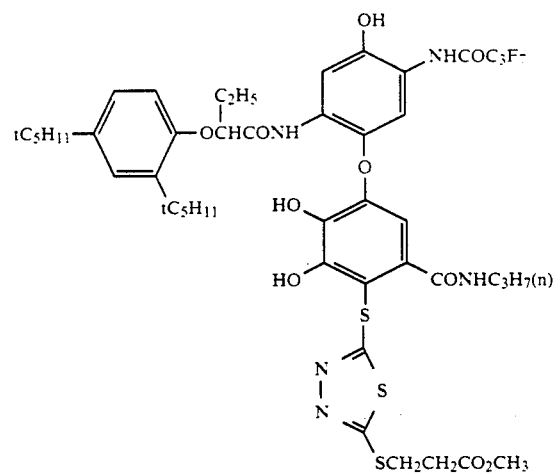
ExC-4
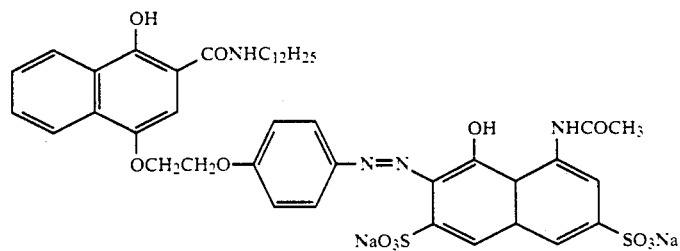
ExC-5
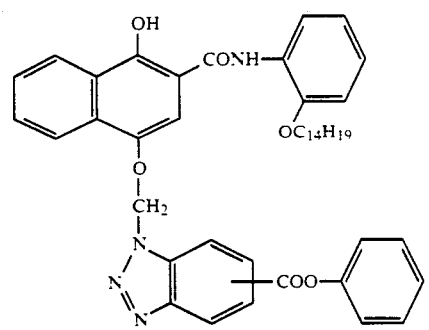
ExC-6
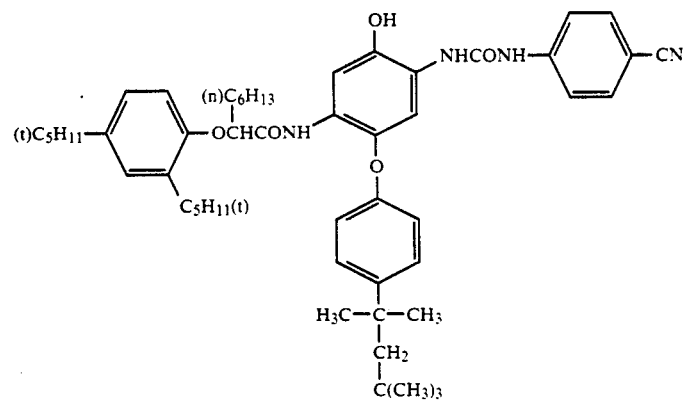
ExC-7

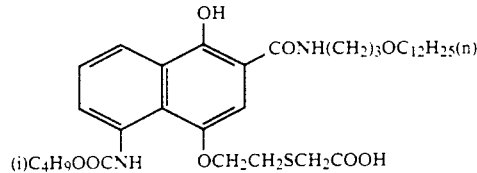
ExY-11
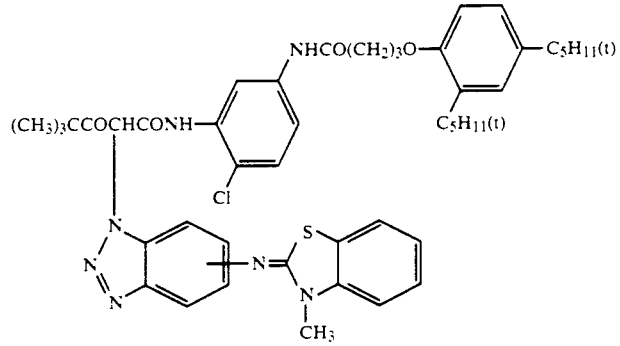
ExM-12
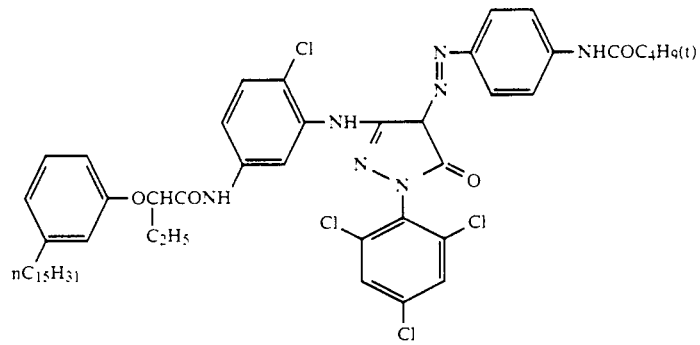
ExY-13
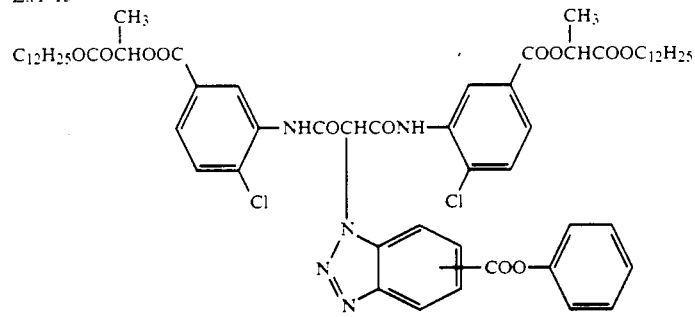
ExM-14
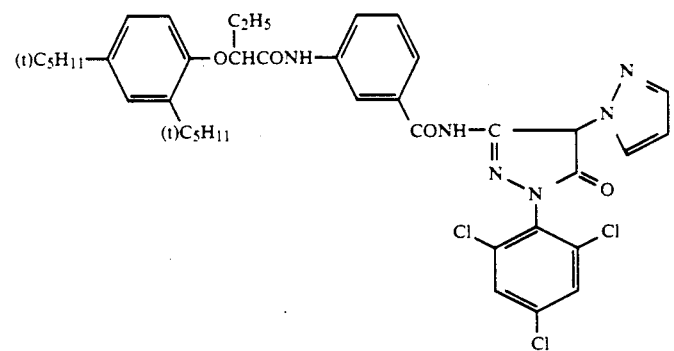
ExY-15                                    ExC-3

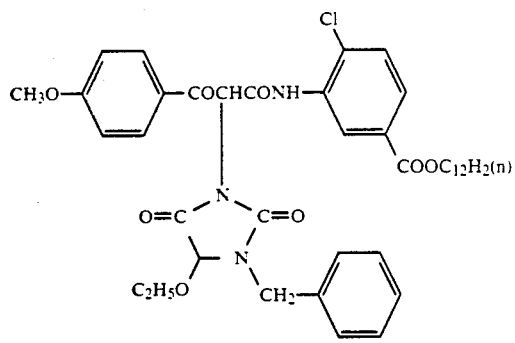
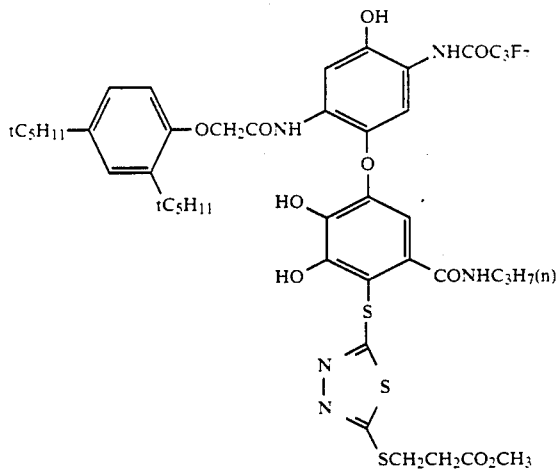
ExS-1
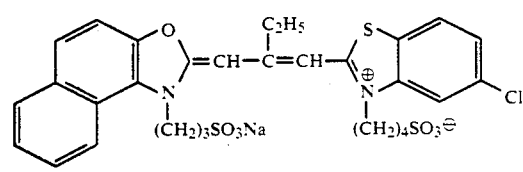
ExS-2
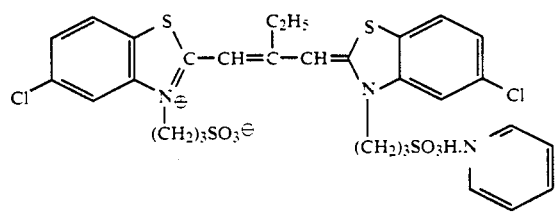
ExS-3
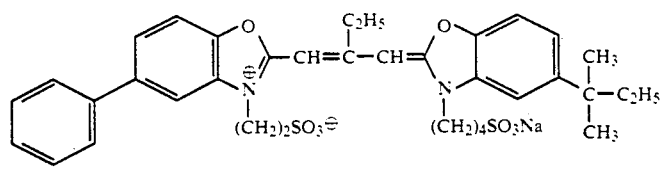
ExS-4
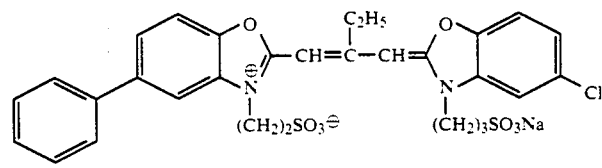
ExS-5
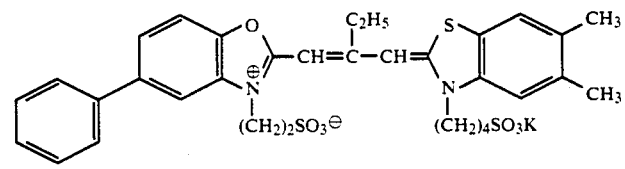
ExS-6
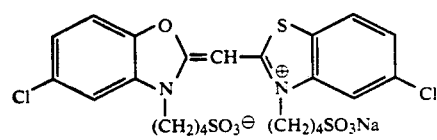
H-1
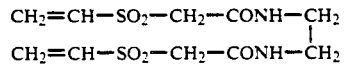
ExF-1

-continued

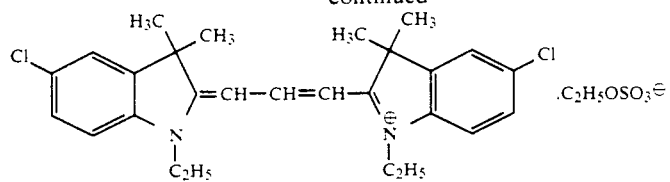

| Compositions of processing solutions | |
|---|---|
| | (gram) |
| Color-developing solution | |
| Pentasodium diethylenetriaminepentaacetate | 1.0 |
| 1-Hydroxyethylidene-1,1-diphosphonate | 3.0 |
| Sodium sulfite | 4.0 |
| Potassium carbonate | 30.0 |
| Potassium bromide | 1.4 |
| Potassium iodide | 1.5 mg |
| Hydroxylaminesulfate | 2.4 |
| 4-(N-Ethyl-N-β-hydroxyethylamino)-2-methyl-anilinesulfate | 4.5 |
| Water to make | 1.0 l |
| pH | 10.05 |
| Bleaching solution | |
| Sodium iron (III) ethylenediaminetetra-acetate trihydrate | 100.0 |
| Disodium ethylenediaminetetraacetate dihydrate | 10.0 |
| Ammonium bromide | 140.0 |
| Ammonium nitrate | 30.0 |
| Aqueous ammonia | 6.5 ml |
| Water to make | 1.0 l |
| pH | 6.0 |
| Fixing solution | |
| Disodium ethylenediaminetetraacetate | 0.5 |
| Sodium sulfite | 7.0 |
| Sodium hydrogensulfite | 5.0 |
| Aqueous solution of ammonium thiosulfate (70%) | 170.0 ml |
| Water to make | 1.0 l |
| pH | 6.7 |
| Stabilizing solution | |
| Formalin (37%) | 2.0 ml |
| Polyoxyethylene-p-monononylphenylether (average molecular weight: 10) | 0.3 |
| Disodium ethylenediaminetetraacetate | 0.05 |
| Water to make | 1.0 l |

Each of the thus-prepared samples was evaluated by sensitometry. The results are shown in Table 5.

TABLE 5

| Sample | Sensitivity* (S) | Gradation (γ) | Color Density** (Dm) |
|---|---|---|---|
| Comparative sample ① | 100 | 0.60 | 2.00 |
| Comparative sample ② | 101 | 0.61 | 2.01 |
| V-A | 110 | 0.78 | 2.31 |
| V-B | 109 | 0.75 | 2.28 |
| V-C | 107 | 0.70 | 2.25 |
| V-D | 105 | 0.69 | 2.2 |
| V-E | 108 | 0.68 | 2.30 |
| V-F | 107 | 0.70 | 2.28 |
| V-G | 105 | 0.72 | 2.24 |
| V-H | 104 | 0.73 | 2.23 |
| V-I | 103 | 0.70 | 2.28 |
| V-J | 103 | 0.64 | 2.25 |
| V-K | 105 | 0.65 | 2.27 |
| V-L | 106 | 0.67 | 2.27 |
| V-M | 106 | 0.68 | 2.28 |
| V-N | 107 | 0.67 | 2.28 |
| V-O | 105 | 0.66 | 2.24 |

*The sensitivity shows the relative value of the sensitivity designated by a reciprocal of the amount of light exposure that gives a density of 0.8 with comparative sample ① assumed as 100.
**The density shows the value at an exposure amount (log E) equal to that giving the magenta density D = 2.0 to comparative sample ①.

As is apparent from the results in Table 5, Samples V-A to V-O of this invention are improved in the sensitivity and the gradation, and these Samples show high color densities.

EXAMPLE 6

A multi-layered color photographic paper designated Sample VI-A was prepared by multi-coatings, composed of the following compositions on a double-sided polyethylene-laminated paper base.

The coating solutions were prepared by mixing and dissolving respective emulsions, chemicals and dispersed emulsions of a coupler. The emulsions and dispersions were prepared as follows.

| Preparation of emulsion Blue-sensitive emulsion | |
|---|---|
| (First solution) | |
| H₂O | 1000 ml |
| NaCl | 5.5 g |
| Gelatin | 32 g |
| (Second solution) | |
| Sulfuric acid (1 N) | 24 ml |
| (Third solution) | |
| Compound A shown below | 3 ml |

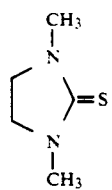

| (Fourth solution) | |
|---|---|
| NaCl | 1.7 g |
| H₂O to make | 200 ml |
| (Fifth solution) | |
| AgNO₃ | 5 g |
| H₂O to make | 200 ml |
| (Sixth solution) | |
| NaCl | 41.3 g |
| K₂IrCl₆ (0.001%) | 0.5 ml |
| H₂O to make | 600 ml |
| (Seventh solution) | |
| AgNO₃ | 120 g |
| H₂O to make | 600 ml |

The first solution was heated to 75° C., and the second and third solutions were added thereto. Then the fourth and fifth solutions were simultaneously added thereto over 10 minutes. After a further 10 minutes had passed, the sixth and seventh solutions were simultaneously added thereto over 35 minutes. Five minutes later the temperature was lowered and desalting was effected. Then water and dispersed gelatin were added and the pH was adjusted to 6.3, thereby giving a monodisperse cube-pure silver chloride emulsion having an average grain size of 1.1 μm and a deviation coefficient (a value obtained by dividing the standard deviation of grain size by the average grain size: s/d) of 0.10.

To the thus-prepared emulsion, 25.2 ml of 0.6% blue spectral-sensitizing dye (CR-7) as a CR compound was added. Then, a 10% KBr aqueous solution was added in a ratio of 0.5 mol % to the host AgCl emulsion, after which the optimally chemically-sensitized stabilizer (XXI-7) by sodium thiosulfite was added in an amount of $10^{-4}$ mol per mol of silver.

| Green-sensitive emulsion | |
|---|---|
| (Eighth solution) | |
| $H_2O$ | 1000 ml |
| NaCl | 3.3 g |
| Gelatin | 32 g |
| (Ninth solution) | |
| Sulfuric acid (1 N) | 24 ml |
| (Tenth solution) | |
| Compound A of the third solution | 3 ml |
| (Eleventh solution) | |
| NaCl | 11.00 g |
| $H_2O$ to make | 200 ml |
| (Twelfth solution) | |
| $AgNO_3$ | 32.00 g |
| $H_2O$ to make | 200 ml |
| (Thirteenth solution) | |
| NaCl | 44.00 g |
| $K_2IrCl_6$ (0.001%) | 2.3 ml |
| $H_2O$ to make | 560 ml |
| (Fourteenth solution) | |
| $AgNO_3$ | 128 g |
| $H_2O$ to make | 560 ml |

The eighth solution was heated to 52° C., and the ninth and tenth solutions were added thereto. Then, the eleventh and twelfth solutions were simultaneously added thereto over 14 minutes. After a further 10 minutes had passed, the thirteenth and fourteenth solutions were simultaneously added thereto over 15 minutes. Five minutes later the temperature was lowered and desalting was effected.

Water and dispersed gelatin were added thereto and the pH was adjusted to 6.2, thereby giving a monodisperse cube-pure silver chloride emulsion having an average grain size of 0.48 μm and a deviation coefficient (s/d) of 0.10. To the thus-prepared emulsion, CR-24 was added at 58° C. in an amount of $4 \times 10^{-4}$ mol per mol of silver halide, after which the fifteenth solution described below was added thereto over 10 minutes, and the resulting emulsion was optimally chemically-sensitized by adding sodium thiosulfite.

| (Fifteenth solution) | |
|---|---|
| KBr | 5.60 g |
| $H_2O$ to make | 280 ml |

As a stabilizer, (XXI-7) was added in an amount of $5 \times 10^{-4}$ mol per mol of silver halide.

Red-Sensitive Emulsion

A red-sensitive emulsion was prepared by repeating the same procedure for the green-sensitive emulsion, except that the sensitizing dye used as the CR-compound was changed to CR-32 in an additive amount of $1.5 \times 10^{-4}$ mol per mol of silver halide, and compound (S-1) was added in an amount of $2.6 \times 10^{-3}$ mol per mol of silver halide.

Preparation of the Coupler Emulsion

To 19.1 g of a yellow coupler (ExY) and 4.4 g of a color image stabilizer (Cpd-1) were added 27.2 ml of ethyl acetate and 7.7 ml of a solvent (Solv-1), and they were mixed until dissolved. The resulting solution was dispersed and emulsified in 185 ml of 10% aqueous gelatin solution containing 8 ml of 10% sodium dodecylbenzenesulfate.

In like manner, emulsions for magenta, cyan, and the intermediate layer were prepared.

Layer Structure

The compositions of the layers in Sample VI-A were as follows. The values represent the coating amount in $g/m^2$. The amount of each silver halide emulsion is represented by the coating amount in terms of silver.
Base: Polyethylene-laminated paper (a white pigment, $TiO_2$, and a bluish dye, ultramarine, were included in the polyethylene film of the first layer side)

| First layer: Blue-sensitive emulsion layer | |
|---|---|
| Silver halide emulsion | 0.30 |
| Gelatin | 1.86 |
| Yellow coupler (ExY) | 0.82 |
| Image-dye stabilizer (Cpd-1) | 0.19 |
| Solvent (Solv-1) | 0.35 |
| Second layer: Color-mix-preventing layer | |
| Gelatin | 0.99 |
| Color-mix inhibitor (Cpd-2) | 0.08 |
| Third layer: Green-sensitive emulsion layer | |
| Silver halide emulsion | 0.36 |
| Gelatin | 1.24 |
| Magenta coupler (Exemplified compound (5)) | 0.65 |
| Image-dye stabilizer (Cpd-3) | 0.25 |
| Image-dye stabilizer (Cpd-4) | 0.12 |
| Solvent (Solv-2) | 0.42 |
| Fourth layer: Ultraviolet-absorbing layer | |
| Gelatin | 1.58 |
| Ultraviolet absorbent (UV-1) | 0.62 |
| Color-mix inhibitor (Cpd-5) | 0.05 |
| Solvent (Solv-3) | 0.24 |
| Fifth layer: Red-sensitive emulsion layer | |
| Silver halide emulsion | 0.23 |
| Gelatin | 1.34 |
| Cyan coupler (a blend of ExC1 and ExC2 in a ratio of 1:1) | 0.34 |
| Image-dye stabilizer (Cpd-6) | 0.17 |
| Polymer (Cpd-7) | 0.40 |
| Solvent (Solv-4) | 0.23 |
| Sixth layer: Ultraviolet-absorbing layer | |
| Gelatin | 0.53 |
| Ultraviolet absorbent (UV-1) | 0.21 |

| -continued | |
|---|---|
| Solvent (Solv-3) | 0.08 |
| Seventh layer: Protective layer | |
| Gelatin | 1.33 |
| Acrylic-modified (modification degree: 17%) copolymer of poly(vinyl alcohol) | 0.17 |
| Liquid paraffin | 0.03 |

The sodium salt of 1-oxy-3,5-dichloro-s-triazine was used as a hardening agent for each layer. Dyes (R-1) and (R-2) were used in each emulsion layer to prevent irradiation.

Next, Samples VI-B to VI-G were prepared in the same manner as Sample VI-A. except that the exemplified compound (5) of the magenta coupler was changed to an equal mol of exemplified compound (6), (11), (14), (20), (23), or (26), respectively.

Further, comparative samples ① and ② were prepared by changing the exemplified compound (5) of Sample VI-A to an equal mol of comparative compound ① or ②, respectively.

(ExY) Yellow Coupler

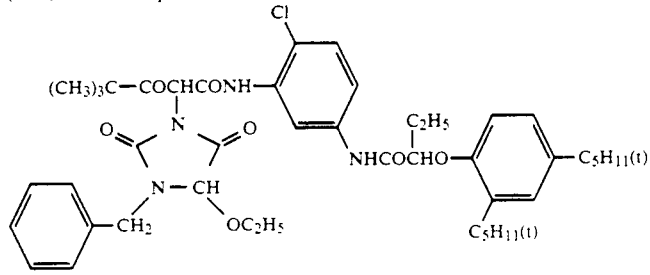

(ExC-1)

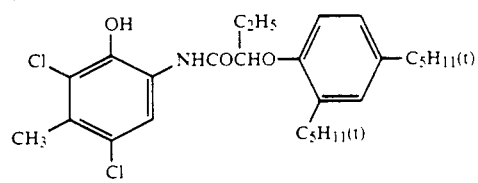

(ExC-2)

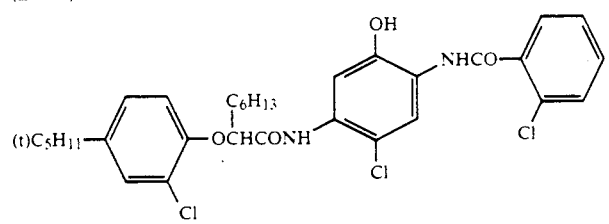

(XXI-7)

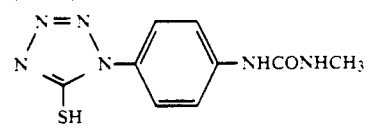

(CR-7)

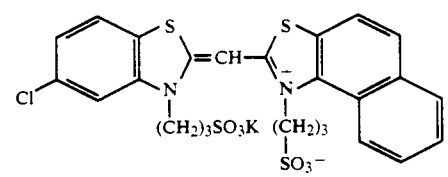

(CR-24)

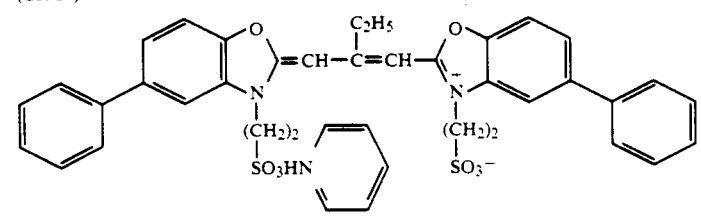

-continued
(CR-32)
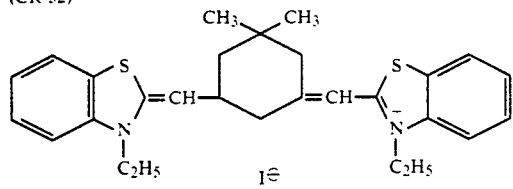
(Cpd-1) Image-dye stabilizer
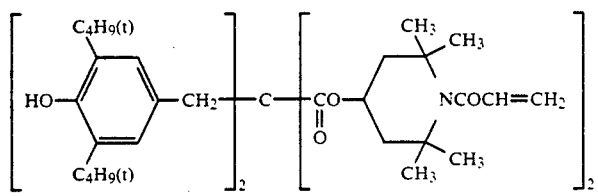
(Cpd-2) Color-mix inhibitor
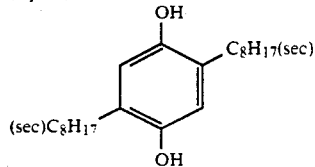
(Cpd-3) Image-dye stabilizer
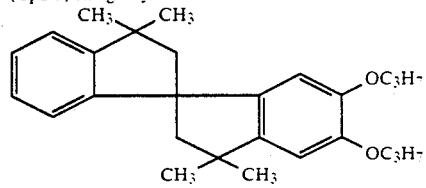
(Cpd-4) Image-dye stabilizer
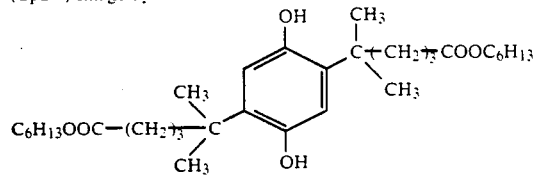
(Cpd-5) Color-mix inhibitor
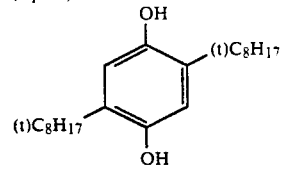
(Cpd-6) Image-dye stabilizer
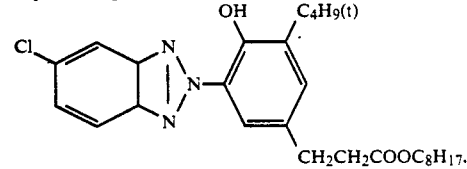
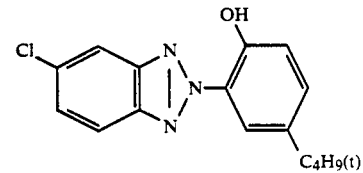
and

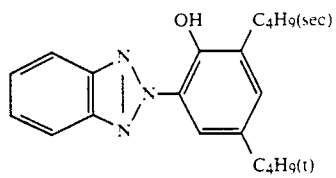
(Mixture of 5:8:9 in weight ratio)
(Cpd-7) Poylmer
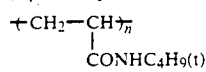
(av. molecular weight: 80,000)
(UV-1) UV Absorbent
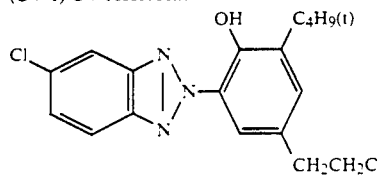
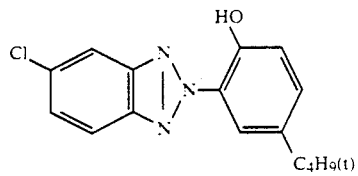
and
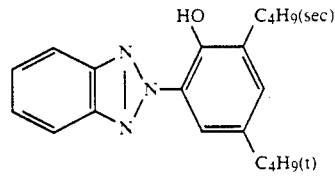
(Mixture of 2:9:8 in weight ratio)
(Solv-1) Solvent
Dibutyl phthalate
(Solv-3) Solvent
Trinonyl phosphate
(Solv-4) Solvent
Tricresyl phosphate
(R-1)
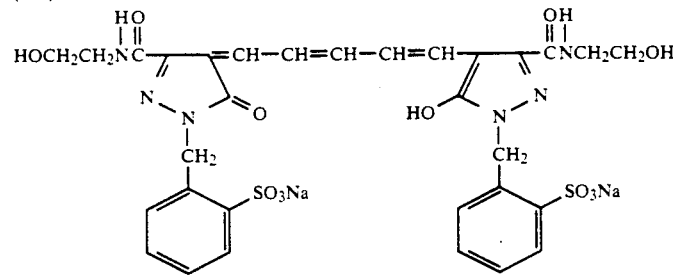
(R-2)

-continued

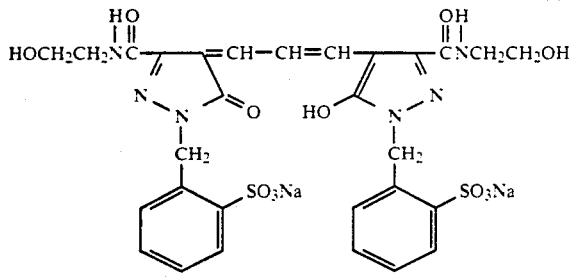

(S-1)

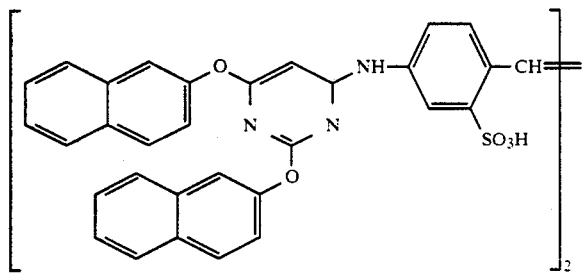

These coated samples were subjected to the following experiments to test photographic characteristics.

First, each of coated samples was subjected to sensitometry (FWH-type, made by Fuji Photo Film Co., Ltd., color temperature at light source: 3200K) using a gradational exposure of light through a green filter. The exposure was conducted to give an exposure time of one-tenth second and an exposure amount of 250 CMS.

Thereafter they were subjected to the following development processing.

| Step | Temperature (°C.) | Time (sec.) |
| --- | --- | --- |
| Color developing | 35 | 45 |
| Bleach-fixing | 35 | 45 |
| Water washing | 28-35 | 90 |

| Color-developing solution | |
| --- | --- |
| Triethanolamine | 8.12 g |
| N,N-diethylhydroxylamine | 4.93 g |
| Fluorescent whitening agent (UVITEX CK. made by Ciba-Geigy) | 2.80 g |
| 4-Amino-3-methyl-N-ethyl-N-[β-methanesulfonamido)ethyl]-p-phenyleneamine sulfate | 4.96 g |
| Sodium sulfite | 0.13 g |
| Potassium carbonate | 18.40 g |
| Potassium hydrogencarbonate | 4.85 g |
| EDTA.2Na.2H$_2$O | 2.20 g |
| Sodium chloride | 1.36 g |
| Water to make | 1000 ml |
| pH | 10.05 |
| Bleach-fixing solution | |
| Ammonium thiosulfate (54 wt. %) | 103.0 ml |
| NH$_3$[EDTA.Fe] | 54.10 ml |
| EDTA.2Na.2H$_2$O | 3.41 g |
| Sodium sulfite | 16.71 g |
| Glacial acetic acid | 8.61 g |
| Water to make | 1000 ml |
| pH | 5.44 |

After processing, measurements were made to obtain the sensitivity and gradation of each sample. The thus-obtained results are shown in Table 6.

TABLE 6

| Sample | Sensitivity* | Gradation** | Max. Density |
| --- | --- | --- | --- |
| Comparative sample ① | 100 | 2.93 | 2.25 |
| Comparative sample ② | 96 | 2.86 | 2.20 |
| VI-A | 119 | 3.13 | 2.36 |
| VI-B | 115 | 3.09 | 2.29 |
| VI-C | 113 | 3.11 | 2.34 |
| VI-D | 108 | 3.11 | 2.31 |
| VI-E | 112 | 3.11 | 2.32 |
| VI-F | 105 | 3.08 | 2.26 |
| VI-G | 108 | 3.09 | 2.27 |

*The sensitivity shows the relative value of the sensitivity designated by a reciprocal of the amount of the light exposure that gives a density of 0.8 with comparative sample ① assumed as 100.
**The gradation shows the gradient of the sensitometry from a density of 0.6 to a density of 2.5.

As is apparent from the results in Table 6, the samples of this invention are much better in each of sensitivity, gradation, and color density in relation to the comparative samples.

EXAMPLE 7

A multi-layered color photographic material that has the following compositions of layers on a double-sided polyethylene-laminated paper base was prepared to obtain Sample VII-A.

| | |
| --- | --- |
| E-ninth layer | Protective layer |
| E-eighth layer | UV-absorbing layer |
| E-seventh layer | Blue-sensitive emulsion layer |
| E-sixth layer | Intermediate layer |
| E-fifth layer | Yellow filter layer |
| E-fourth layer | Intermediate layer |
| E-third layer | Green-sensitive emulsion layer |
| E-second layer | Intermediate layer |
| E-first layer | Red-sensitive emulsion layer |
| | Base |
| B-first layer | Backing layer |

-continued

| B-second layer | Protective layer |
|---|---|

Composition of Layers

The composition of each layer is shown below. The values represent the coating amount in $g/m^2$. The amount of silver halide emulsion and colloidal silver represent the coating amounts in terms of silver, and the amount of the sensitizing dye represents mol per mol of silver halide.

Base: Polyethylene-laminated paper (a white pigment, $TiO_2$, and a bluish dye, ultramarine, were included in the polyethylene film of the E-first layer side.

| E-first layer: | |
|---|---|
| Silver halide emulsion | 0.26 |
| Spectral sensitizing dye (ExSS-1) | $1.0 \times 10^{-4}$ |
| Spectral sensitizing dye (ExSS-2) | $6.1 \times 10^{-5}$ |
| Gelatin | 1.11 |
| Cyan coupler (ExCC-1) | 0.21 |
| Cyan coupler (ExCC-2) | 0.26 |
| UV absorbent (ExUV-1) | 0.17 |
| Solvent (ExS-1) | 0.23 |
| Development conditioner (ExGC-1) | 0.02 |
| Stabilizer (ExA-1) | 0.006 |
| Nucleation accelerator (ExZS-1) | $3.0 \times 10^{-4}$ |
| Nucleating agent (ExZK-1) | $8.0 \times 10^{-6}$ |
| E-second layer: | |
| Gelatin | 1.41 |
| Color-mix inhibitor (ExKB-1) | 0.09 |
| Solvent (ExS-1) | 0.10 |
| Solvent (ExS-2) | 0.10 |
| E-third layer: | |
| Silver halide emulsion | 0.23 |
| Spectral sensitizing dye (ExSS-3) | $3.0 \times 10^{-4}$ |
| Gelatin | 1.05 |
| Magenta coupler, exemplified compound (5) | 0.16 |
| Image-dye stabilizer (ExSA-1) | 0.20 |
| Solvent (ExS-3) | 0.25 |
| Development conditioner (ExGC-1) | 0.02 |
| Stabilizer (ExA-1) | 0.006 |
| Nucleation accelerator (ExZS-1) | $2.7 \times 10^{-4}$ |
| Nucleating agent (ExZK-1) | $1.4 \times 10^{-5}$ |
| E-fourth layer: | |
| Gelatin | 0.47 |
| Color-mix inhibitor (ExKB-1) | 0.03 |
| Solvent (ExS-1) | 0.03 |
| Solvent (ExS-2) | 0.03 |
| E-fifth layer: | |
| Colloidal silver | 0.09 |
| Gelatin | 0.49 |
| Color-mix inhibitor (ExKB-1) | 0.03 |
| Solvent (ExS-1) | 0.03 |
| Solvent (ExS-2) | 0.03 |
| E-sixth layer: | |
| Same as the E-fourth layer | |
| E-seventh layer: | |
| Silver halide emulsion | 0.40 |
| Spectral sensitizing dye (ExSS-3) | $4.2 \times 10^{-4}$ |
| Gelatin | 2.17 |
| Yellow coupler (ExYC-1) | 0.51 |
| Solvent (ExS-2) | 0.20 |
| Solvent (ExS-4) | 0.20 |
| Development conditioner (ExGC-1) | 0.06 |
| Stabilizer (ExA-1) | 0.001 |
| Nucleation accelerator (ExZS-1) | $5.0 \times 10^{-4}$ |
| Nucleating agent | $1.2 \times 10^{-6}$ |
| E-eighth layer: | |
| Gelatin | 0.54 |
| UV absorbent (ExUV-2) | 0.21 |
| Solvent (ExS-4) | 0.08 |
| E-ninth layer: | |
| Gelatin | 1.28 |
| Acryl-modified (modification degree: 17%) copolymer of poly(vinyl alcohol) | 0.17 |
| Liquid paraffin | 0.03 |
| Poly(methyl methacrylate) latex particle (av. diameter of particle: 2.8 μm) | 0.05 |
| B-first layer: | |
| Gelatin | 8.70 |
| B-second layer: | |
| Same as the E-ninth layer | |

In addition to the above-described components, a gelatin hardener, ExGK-1, and a surface-active agent were added to each layer.

Samples VII-B to VII-G were prepared in the same manner as Sample VII-A, except that the exemplified compound (5) of the magenta coupler was changed to an equal mol of exemplified compound (6), (11), (14), (20), (23), or (26), respectively.

Further, comparative samples ① and ② were prepared by changing the exemplified compound (5) of Sample VII-A to an equal mol of the above-described comparative compound ① or ②, respectively.

Samples VII-A to VII-G and comparative samples ① and ② were subjected to a white-light exposure for 0.1 sec. through an optical wedge and a filter of blue, green, or red, respectively, and then the processing described hereinbelow.

Compounds used in this example are as follows:

(ExCC-1) Cyan coupler

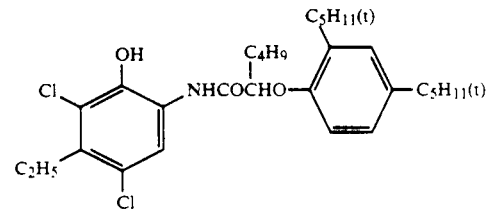

-continued
(ExCC-2) Cyan coupler
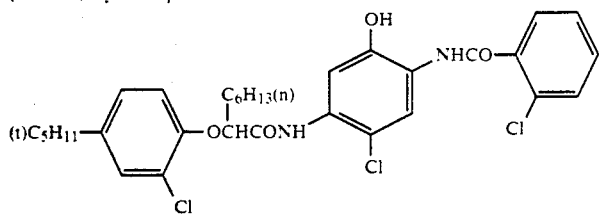
(ExYC-1) Yellow coupler
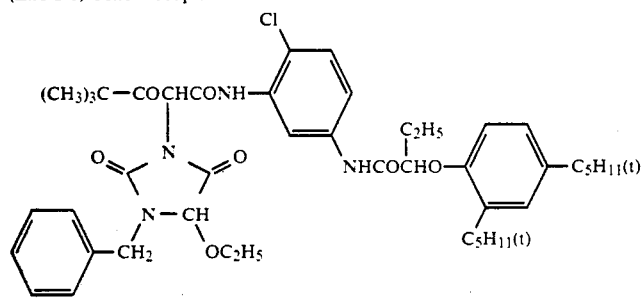
(ExSS-1) Spectral sensitizing dye
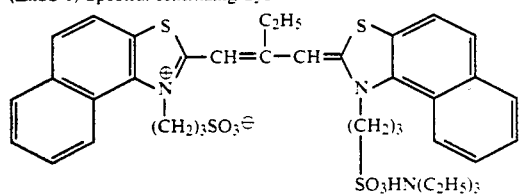
(ExSS-2) Spectral sensitizing dye
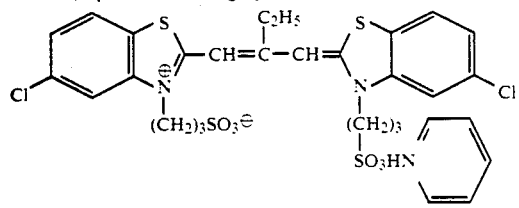
(ExSS-3) Spectral sensitizing dye
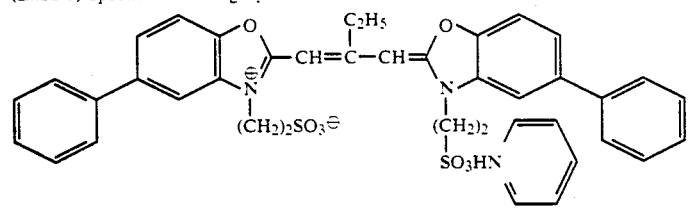
(ExSS-4) Spectral sensitizing dye
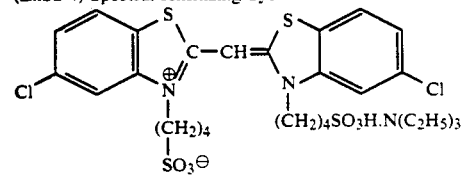
(ExS-1) Solvent
Tricresyl phosphate
(ExS-2) Solvent
Dibutyl phthalate
(ExS-3) Solvent
Mixture of trioctyl phosphate and tricresyl phosphate in volumn ratio of 1:1

(ExS-4) Solvent
Trinonyl phosphate (ExUV-1) UV absorbent
Mixture of the following compounds (1), (2), and (3) in weight ratio of 5:8:9

(1) 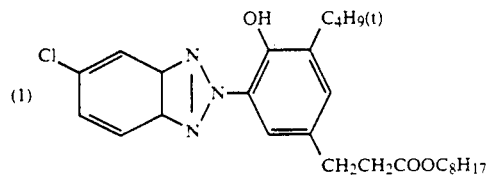

(2) 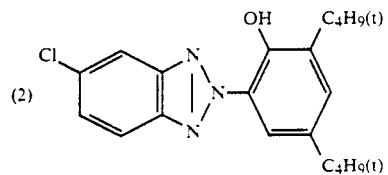

(3) 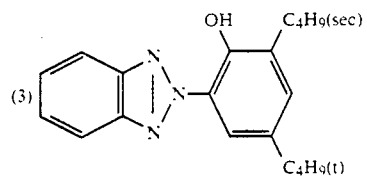

(ExUV-2) UV absorbent
Mixture of the above shown compounds (1), (2), and (3) in weight ratio of 2:9:8

(ExSA-1) Image-dye stabilizer

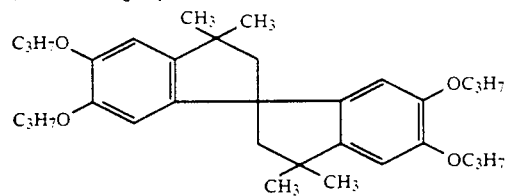

(ExKB-1) Color-mix inhibitor

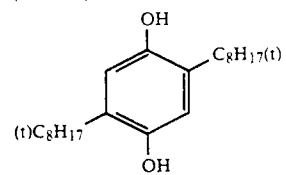

(ExGC-1) Development conditioner

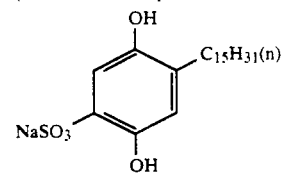

(ExA-1) Stabilizer
4-Hydroxy-5,6-trimethylene-1,3,3a,7-tetrazaindene (ExZS-1) Nucleation accelerator
2-(3-Dimethylaminopropylthio)-5-mercapto-1,3,4-thiadiazole hydrochloride (ExZK-1) Nucleating agent
6-Ethoxythiocarbonylamino-2-methyl-1-propargyl-quinolinium trifluoromethane sulfonate (ExGK-1) Gelatin hardener
1-Oxy-3,5-dichloro-S-triazine sodium salt

| Step | Processing procedure | |
|---|---|---|
| | Time (sec.) | Temperature (°C.) |
| Color developing | 80 | 38 |
| Bleach-fixing | 30 | 38 |
| Water washing ① | 30 | 38 |
| Water washing ② | 30 | 38 |

The washing steps with water were carried out by the so-called counter-current replenishing mode, in which replenisher is fed to the tank of water washing ②, and overflowed washing water from the tank of water washing ② is fed to the tank of water washing ①.

| | Mother liquid |
|---|---|
| Color-developing solution | |
| Diethylenetriamine heptaacetate | 0.5 g |
| 1-Hydroxyethylydene-1,1-diphosphonate | 0.5 g |
| Diethyleneglycol | 8.0 g |
| Benzyl alcohol | 10.0 g |
| Sodium bromide | 0.5 g |
| Sodium chloride | 0.7 g |
| Sodium sulfite | 2.0 g |
| N,N-diethylhydroxylamine | 3.5 g |
| 3-Methyl-4-amino-N-ethyl-N-(β-methanesulfonamidoethyl)-aniline | 6.0 g |
| Potassium carbonate | 30.0 g |
| Fluorescent brightener (stilbene system) | 1.0 g |
| Pure water to make | 1000 ml |
| pH (adjusted by potassium hydroxide or hydrochloric acid) | 10.50 |
| Bleach-fixing solution | |
| Ammonium thiosulfate | 110 g |
| Sodium hydrogenesulfite | 10 g |
| Ammonium iron (III) ethylenediamine-tetraacetate dihydrate | 40 g |
| Disodium ethylenediaminetetraacetate dihydrate | 5 g |
| 2-Mercapto-1,3,4-triazole | 0.5 g |
| Pure water to make | 1000 ml |
| pH (adjusted by aqueous ammonia or hydrochloric acid) | 7.0 |

Washing Water

Pure water (wherein pure water represents tap water from which all cations except hydrogen ions and all anions except hydroxyl ions are removed to 1 ppm or less, by an ion-exchange treatment)

Each of the thus-processed samples afforded a distinct magenta color image of high saturation. The magenta density of each processed sample was measured to obtain the sensitivity, gradation (γ), and maximum density. The results are shown in Table 7.

TABLE 7

| Sample | Sensitivity* | Gradation** | Max. Density |
|---|---|---|---|
| Comparative sample ① | 100 | 2.93 | 2.25 |
| Comparative sample ② | 97 | 2.87 | 2.21 |
| VII-A | 119 | 3.13 | 2.36 |
| VII-B | 118 | 3.12 | 2.32 |
| VII-C | 113 | 3.11 | 2.34 |
| VII-D | 110 | 3.13 | 2.33 |
| VII-E | 109 | 3.08 | 2.29 |
| VII-F | 106 | 3.10 | 2.28 |
| VII-G | 108 | 3.09 | 2.27 |

*The sensitivity shows the relative value of the sensitivity designated by a reciprocal of the amount of light exposure that gives a density of 0.8 with the value of the comparative sample ① assumed as 100.
**The gradation shows the gradient of the sensitometry from a density of 0.6 to a density of 2.5.

As is apparent from the results in Table 7, the samples of this invention are excellent in each of sensitivity, gradation, and color density.

EXAMPLE 8

A color photographic material was prepared by multi-coatings composed of the following for the first to the twelfth layers on a double-sided polyethylene-laminated paper base. A white pigment (titanium white) and small amount of bluish dye (ultramarine) were included in the polyethylene film laminated on the first layer side.

Composition of the Photosensitive Layers

In the following compositions, the coating amount of each ingredient is indicated in g/m², but the coating amount of the silver halide is indicated in terms of silver.

| First layer: Gelatin layer | |
|---|---|
| Gelatin | 1.30 |
| Second layer: Antihalation layer | |
| Black colloidal silver | 0.10 |
| Gelatin | 0.70 |
| Third layer: Red-sensitive emulsion (low sensitivity) layer | |
| Silver chloroiodobromide emulsion spectral-sensitized by red-sensitizing dye (ExS-1, -2, and -3) (silver chloride: 1 mol %, silver iodide: 4 mol %, average grain size: 0.3 μm, grain size distribution: 10%, cubic, core-shell type of iodide core) | 0.06 |
| Silver iodobromide emulsion spectral-sensitized by red-sensitizing dye (ExS-1, -2, and -3) (silver iodide: 5 mol %, average grain size: 0.45 μm, grain size distribution: 20%, tabular (aspect ratio: 5)) | 0.10 |
| Gelatin | 1.00 |
| Cyan coupler (ExC-1) | 0.14 |
| Cyan coupler (ExC-2) | 0.07 |
| Discoloration inhibitor (mixture of Cpd-2, -3, -4, and -9 in equal volume) | 0.12 |
| Coupler dispersion medium (Cpd-5) | 0.03 |
| Coupler solvent (Solv-1, -2, and -3) | 0.06 |
| Fourth layer: Red-sensitive emulsion (highly sensitive) layer | |
| Silver iodobromide emulsion spectral-sensitized by red-sensitizing dye (ExS-1, -2, and -3) (silver iodide: 6 mol %, average grain size: 0.75 μm, grain size distribution: 25%, tabular (aspect ratio: 8, iodide core) | 0.15 |
| Gelatin | 1.00 |
| Cyan coupler (ExC-1) | 0.20 |
| Cyan coupler (ExC-2) | 0.10 |
| Discoloration inhibitor (mixture of Cpd-2, -3, -4, and -9 in equal | 0.15 |

| | |
|---|---|
| volume) | |
| Coupler dispersion medium (Cpd-5) | 0.03 |
| Coupler solvent (Solv-1, -2, and -3) | 0.10 |
| Fifth layer: Intermediate layer | |
| Magenta colloidal silver | 0.02 |
| Gelatin | 1.00 |
| Color-mix inhibitor (Cpd-6, and -7) | 0.08 |
| Color-mix inhibitor solvent (Solv-4 and -5) | 0.16 |
| Polymer latex (Cpd-8) | 0.10 |
| Sixth layer: Green-sensitive emulsion (low sensitivity) layer | |
| Silver chloroiodobromide emulsion spectral-sensitized by green-sensitizing dye (ExS-3) (silver chloride: 1 mol %, silver iodide: 2.5 mol %, average grain size: 0.28 μm, grain size distribution: 12%, cubic, core-shell type of iodide core) | 0.04 |
| Silver iodobromide emulsion spectral-sensitized by green-sensitizing dye (ExS-3) (silver iodide: 2.8 mol %, average grain size: 0.45 μm, grain size distribution: 12%, tabular (aspect ratio: 5)) | 0.06 |
| Gelatin | 0.80 |
| Magenta coupler (ExM-1) | 0.10 |
| Stain inhibitor (Cpd-10) | 0.01 |
| Stain inhibitor (Cpd-11) | 0.001 |
| Stain inhibitor (Cpd-12) | 0.01 |
| Coupler dispersion medium (Cpd-5) | 0.05 |
| Coupler solvent (Solv-4 and -6) | 0.15 |
| Seventh layer: Green-sensitive emulsion (highly sensitive) layer | |
| Silver iodobromide emulsion spectral-sensitized by green-sensitizing dye (ExS-3) (silver iodide: 3.5 mol %, average grain size: 0.9 μm, grain size distribution: 23%, tabular (aspect ratio: 9, uniform iodide type)) | 0.10 |
| Gelatin | 0.80 |
| Magenta coupler (ExM-1) | 0.10 |
| Discoloration inhibitor (Cpd-9) | 0.10 |
| Stain inhibitor (Cpd-10) | 0.01 |
| Stain inhibitor (Cpd-11) | 0.001 |
| Stain inhibitor (Cpd-12) | 0.01 |
| Coupler dispersion medium (Cpd-5) | 0.05 |
| Coupler solvent (Solv-4 and -6) | 0.15 |
| Eighth layer: Yellow filter layer | |
| Yellow colloidal silver | 0.20 |
| Gelatin | 1.00 |
| Color-mix inhibitor (Cpd-7) | 0.06 |
| Color-mix inhibitor solvent (Solv-4 and -5) | 0.15 |
| Polymer latex (Cpd-8) | 0.10 |
| Ninth layer: Blue-sensitive emulsion (low sensitivity) layer | |
| Silver chloroiodobromide emulsion spectral-sensitized by blue-sensitizing dye (ExS-5 and -6) (silver chloride: 2 mol %, silver iodobromide: 2.5 mol %, average grain size: 0.35 μm, grain size distribution: 8%, cubic, core-shell type of iodide core) | 0.07 |
| Silver iodobromide emulsion spectral-sensitized by blue-sensitizing dye (ExS-5 and -6) (silver iodobromide: 2.5 mol %, average grain size: 0.45 μm, grain size distribution: 16%, tabular (aspect ratio: 6)) | 0.10 |
| Gelatin | 0.50 |
| Yellow coupler (ExY-1) | 0.20 |
| Stain inhibitor (Cpd-11) | 0.001 |
| Discoloration inhibitor | 0.10 |
| Coupler dispersion medium (Cpd-5) | 0.05 |
| Coupler solvent (Solv-2) | 0.05 |
| Tenth layer: Blue-sensitive emulsion (highly sensitive) layer | |
| Silver iodobromide emulsion spectral-sensitized by blue-sensitizing dye (ExS-5 and -6) (silver iodide: 2.5 mol %, average grain size: 1.2 μm, grain size distribution: 21%, tabular (aspect ratio: 14)) | 0.25 |
| Gelatin | 1.00 |
| Yellow coupler (ExY-1) | 0.40 |
| Stain inhibitor (Cpd-11) | 0.002 |
| Discoloration inhibitor (Cpd-6) | 0.10 |
| Coupler dispersion medium (Cpd-5) | 0.05 |
| Coupler solvent (Solv-2) | 0.10 |
| Eleventh layer: Ultraviolet-absorbing layer | |
| Gelatin | 1.50 |
| UV absorbent (Cpd-1, -3, and -13) | 1.00 |
| Color-mix inhibitor (Cpd-6 and -14) | 0.06 |
| UV-absorbent solvent (Solv-1 and -2) | 0.15 |
| Irradiation-preventing dye (Cpd-15 and -16) | 0.02 |
| Irradiation preventing dye (Cpd-17 and -18) | 0.02 |
| Twelfth layer: Protective layer | |
| Fine grain silver chlorobromide (silver chloride: 97 mol %, average grain size: 0.2 μm) | 0.07 |
| Modified PVA | 0.02 |
| Gelatin | 1.50 |
| Gelatin hardener (H-1) | 0.17 |

To each layer described above, Alkanol XC (made by Dupont) and sodium alkylbenzenesulfonate were added as emulsion dispersion aids, and succinic acid ester and Magefac F-120 (made by Dainippon Ink Co.) were added as coating aids. In the layers containing silver halide or colloidal silver, (Cpd-19), (Cpd-20), and (Cpd-21) were used as stabilizers. Compounds used in this Example are as follows:

ExS-1

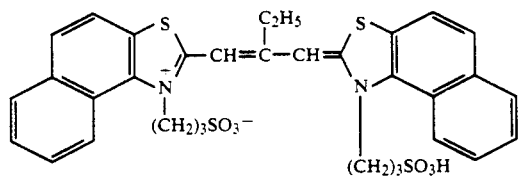

ExS-2

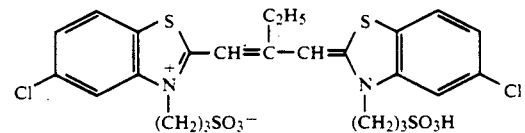

ExS-3

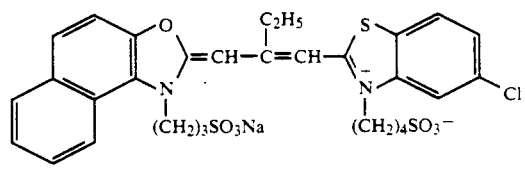

ExS-4
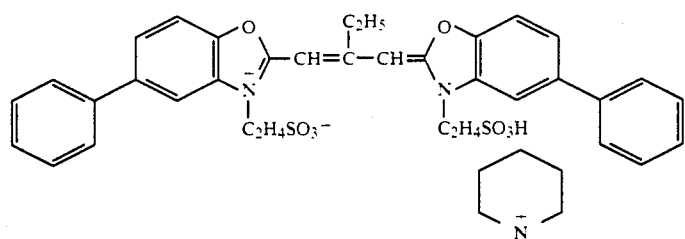
ExS-5
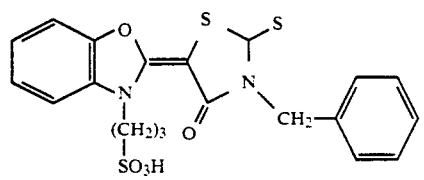
Cpd-1
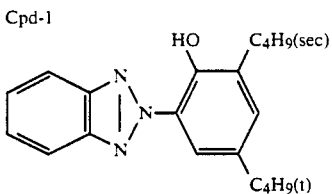
Cpd-2
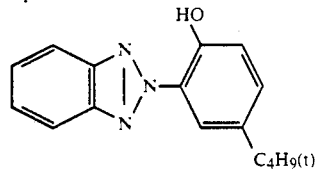
Cpd-3
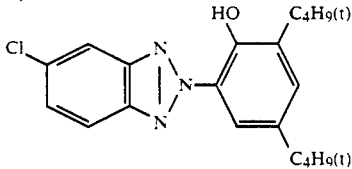
Cpd-4
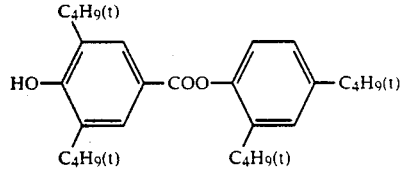
Cpd-5
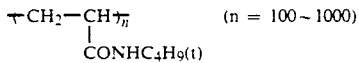
(n = 100~1000)
Cpd-6
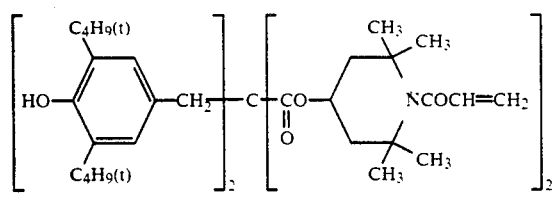
Cpd-7
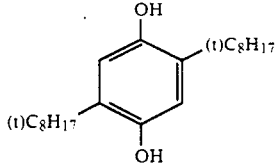
Cpd-8
Poly (ethyl acrylate)
Cpd-9
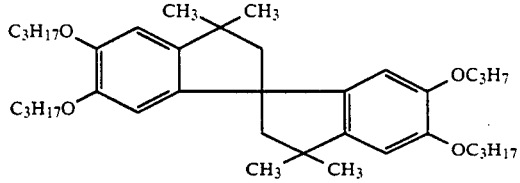
Cpd-10
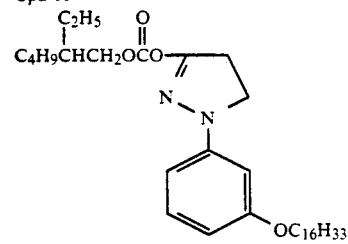
Cpd-11
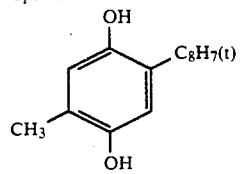
Cpd-12
Cpd-13

-continued
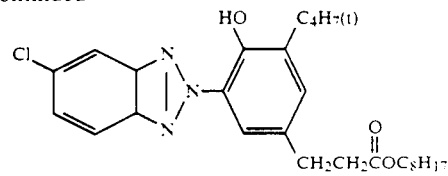
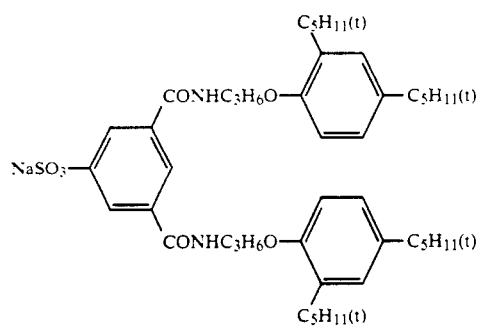
Cpd-14
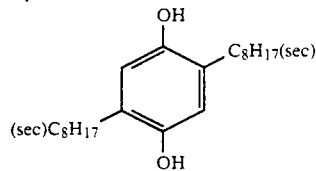
Cpd-15
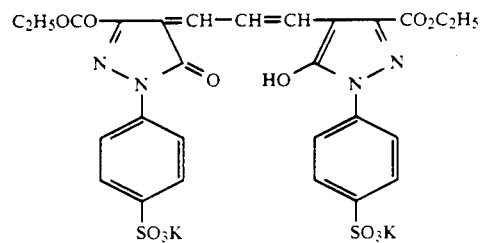
Cpd-16
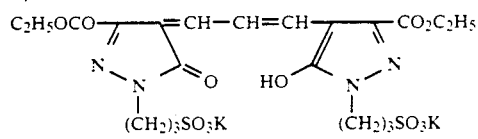
Cpd-17
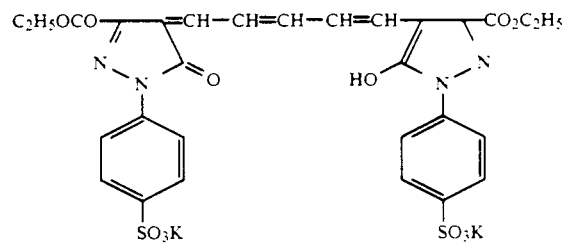
Cpd-18
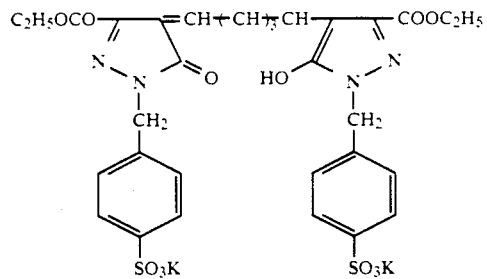
Cpd-19
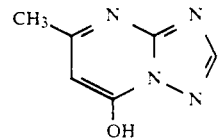
Cpd-20
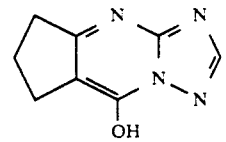
Cpd-21
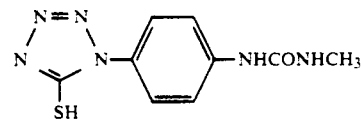
EXC-1
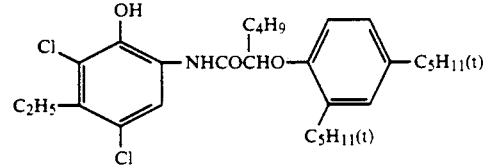
EXC-2
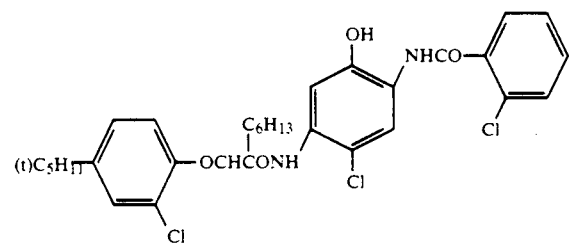

-continued

EXM-1 was selected from the group consisting of the following compounds:
Exemplified compound (5), (6), (7), (10), (12), (19), (20), (22), (23), and (26)

ExY-1

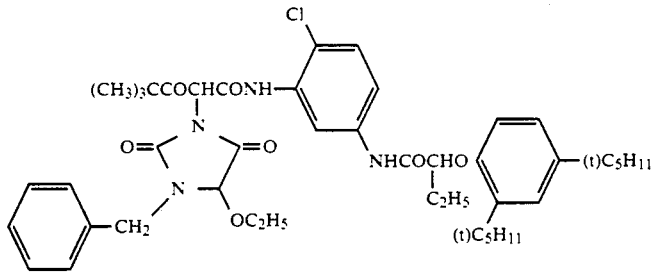

Solv-1 Di(2-ethylhexyl) phthalate
Solv-3 Di(3-methylhexyl) phthalate
Solv-5 Dibutyl phthalate
Solv-7 1,2-Bis(vinylsulfonylacetoamido) ethane Solv-2 Trinonyl phosphate
Solv-4 Tricresyl phosphate
Solv-6 Trioctyl phosphate Each sample was subjected to a conventional light exposure through an optical wedge, and to the same processing as in Example 3. The examples afforded the same color images excellent in gradation and maximum density as the sample of the present invention in Example 3.

Having described our invention as related to the embodiment, it is our intention that the invention is not limited by any of the details of the description, unless otherwise specified, but rather be construed broadly within its spirit and scope as set out in the accompanying claims.

What we claim is:

1. A magenta dye-forming coupler represented by formula (I) or (II):

Formula (I):

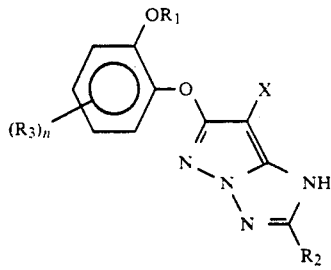

Formula (II):

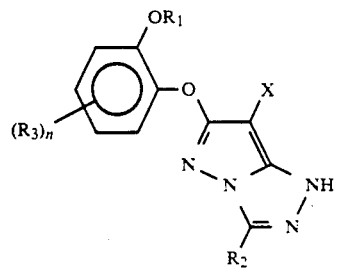

wherein:

$R_1$ represents a hydrogen atom, an alkyl group, or an aryl group;

$R_2$ represents an alkyl group, an aryl group, a heterocyclic group, a cyano group, an alkoxy group, an aryloxy group, an alkylthio group, an arylthio group, or a heterocyclic thio group;

$R_3$ represents a hydrogen atom, a halogen atom, an alkoxy group, an aryloxy group, an alkylamino group, an anilino group, an alkylthio group, an arylthio group;

X represents a hydrogen atom or a coupling split-off group;

n is an integer of 0 to 4;

$R_1$ and $R_3$ may bond together to form a ring.

2. The magenta dye-forming coupler as claimed in claim 1, wherein the alkyl group of $R_1$ is one having 1 to 18 carbon atoms.

3. The magenta dye-forming coupler as claimed in claim 1, wherein the aryl group of $R_1$ is one having 6 to 20 carbon atoms.

4. The magenta dye-forming coupler as claimed in claim 1, wherein the alkyl group of $R_1$ is selected from methyl, ethyl, isopropyl, t-butyl, phenylmethyl, methoxyethyl and 2-phenoxyethyl.

5. The magenta dye-forming coupler as claimed in claim 1, wherein the aryl group of $R_1$ is selected from phenyl, 4-methylphenyl, 4-t-butylphenyl, 4-halogenophenyl, and 4-alkoxyphenyl.

6. The magenta dye-forming coupler as claimed in claim 1, wherein $R_2$ represents a group selected from sulfonamidoalkyl, acylaminoalkyl, sulfonamidophenylalkyl, acylaminophenylalkyl, alkylsulfonylalkyl, phenylsulfonylalkyl and unsubstituted alkyl; sulfonamidophenyl, acylaminophenyl, alkoxyphenyl, aryloxyphenyl, substituted alkylphenyl, sulfonamidonaphthyl, acylaminonaphthyl, unsubstituted phenyl, and unsubstituted naphthyl; 2-furyl, 2-thienyl, 2-pyrimidinyl, and 2-benzothiazolyl; cyano; methoxy, ethoxy, 2-methoxyethoxy, 2-dodecylethoxy, 2-methanesulfonylethoxy, phenoxy, 2-methylphenoxy, and 4-t-butylphenoxy; methylthio, octylthio, tetradecylthio, 2-phenoxyethylthio, 3-phenoxypropylthio, and 3-(4-t-butylphenoxy)propylthio; phenylthio, 2-butoxy-5-t- octylphenylthio, 3-pentadecylphenylthio, 2-carboxyphenylthio, and 4-tetradecaneamidophenylthio; 2-benzothiazolylthio, 2,4-di-phenoxy-1,3,5-triazole-6-thio, and 2-pyridylthio.

7. The magenta dye-forming coupler as claimed in claim 1, wherein $R_3$ represents a group selected from hydrogen atom, fluorine, chlorine, and bromine; methoxy, ethoxy, 2-methoxyethoxy, 2-dodecylethoxy, and 2-methanesulfonylethoxy; phenoxy, 2-methylphenoxy, and 4-t-butylphenoxy; methylamino, ethylamino, decylamino, dimethylamino, and diethylamino; phenylamino, 2-chloroanilino, N-methylanilino, and 3-alkoxyanilino; methylthio, octylthio, tetradecylthio, 2-phenoxyethylthio, 3-phenoxypropylthio, and 3-(4-t-butylphenoxy)propylthio; and phenylthio, 2-butoxy-5-t-octylphenylthio, 3-pentadecylphenylthio, 2-carboxyphenylthio, and 4-tetradecaneamidophenylthio.

8. The magenta dye-forming coupler as claimed in claim 1, wherein X represents a coupling split-off group.

9. The magenta dye-forming coupler as claimed in claim 1, wherein X represents a hydrogen atom.

10. The magenta dye-forming coupler as claimed in claim 1, wherein the coupling split-off group is selected from a halogen atom, a carboxyl group, or a group that links via an oxygen atom, a nitrogen atom, or a sulfur atom.

11. The magenta dye-forming coupler as claimed in claim 1, wherein the coupling split-off group is selected from halogen atoms or groups that link via a sulfur atom.

12. The magenta dye-forming coupler as claimed in claim 1, wherein $R_2$ is an alkyl group having 5 to 60 carbon atoms, an aryl group having 6 to 80 carbon atoms, a heterocyclic group having 4 to 80 carbon atoms, an alkylthio group having 5 to 60 carbon atoms, an arylthio group having 6 to 80 carbon atoms, or a heterocyclic thio group having 4 to 80 carbon atoms.

13. The magenta dye-forming coupler as claimed in claim 1, wherein $R_3$ is an alkoxy group having 1 to 20 carbon atoms, an aryloxy group having 6 to 20 carbon atoms, an alkylamino group having 1 to 20 carbon atoms, an anilino group having 6 to 20 carbon atoms, an alkylthio group having 1 to 20 carbon atoms, or an arylthio group having 6 to 20 carbon atoms.

14. The magenta dye-forming coupler as claimed in claim 10, wherein the coupling split-off group is (i) a group that links via an oxygen atom which is selected from the group consisting of acetoxy, propanoyloxy, benzoyloxy, 2,4-dichlorobenzoyloxy, ethoxyloxaloyl, pyruvinyloxy, cinnamoyloxy, phenoxy, 4-cyanophenoxyl, 4-methanesulfonamidophenoxy, 4-methanesulfonylphenoxy, alpha-naphthoxy, 3-pentadecylphenoxy, benzyloxycarbonyloxy, ethoxy, 2-cyanoethoxy, benzyloxy, 2-phenetyloxy, 2-phenoxyethoxy, 5-phenyltetrazoyloxy, and 2-benzothiazolyloxy, (ii) a group that links via a nitrogen atom which is selected from the group consisting of benzenesulfonamido, N-ethyltoluenesulfonamido, heptafluorobutaneamido, 2,3,4,5,6-pentafluorobenzamido, octanesulfonamido, p-cyanophenylureido, N,N-diethylsulfamoylamino, 1-piperidyl, 5,5-dimethyl-2,4-dioxo-3-oxazolidinyl, 1-benzyl-ethoxy-3-hydantoinyl, 2N-1,1-dioxo-3(2H)-oxo-1,2-benzoisothiazolyl, 2-oxo-1,2-dihydro-1-pyridinyl, imidazolyl, pyrazolyl, 3,5-diethyl-1,2,4-triazol-1-yl, 5- or 6-bromo-benzotriazole-1-yl, 5-methyl-1,2,3,4-tetrazol-1-yl, and benzimidazolyl, or (iii) a group that links via a sulfur atom which is selected from the group consisting of phenylthio, 2-carboxyphenylthio, 2-methoxy-5-t-octylphenylthio, 4-methanesulfonylphenylthio, 4-octanesulfonamidophenylthio, benzylthio, 2-cyanoethylthio, 1-ethoxycarbonyltridecylthio, 5-phenyl-2,3,4,5-tetrazolythio, and 2-benzothiazolyl.

* * * * *